US006872525B2

(12) United States Patent
Ishibashi et al.

(10) Patent No.: US 6,872,525 B2
(45) Date of Patent: Mar. 29, 2005

(54) METHOD FOR SELECTIVELY SEPARATING LIVE CELLS EXPRESSING A SPECIFIC GENE

(75) Inventors: Kaname Ishibashi, Shizuoka (JP); Akihiko Tsuji, Shizuoka (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 147 days.

(21) Appl. No.: 09/775,818

(22) Filed: Feb. 5, 2001

(65) Prior Publication Data

US 2001/0044100 A1 Nov. 22, 2001

(30) Foreign Application Priority Data

Feb. 4, 2000 (JP) ...................................... P2000-028117
Apr. 28, 2000 (JP) ...................................... P2000-130793

(51) Int. Cl.[7] .......................... C12Q 1/68; C07H 21/02; C07H 21/04
(52) U.S. Cl. ......................... 435/6; 536/23.1; 536/24.3
(58) Field of Search ............................. 435/6; 536/23.1, 536/24.3; 935/76, 77, 78

(56) References Cited

U.S. PATENT DOCUMENTS

| | | | |
|---|---|---|---|
| 4,996,143 A | | 2/1991 | Heller et al. |
| 5,225,326 A | | 7/1993 | Bresser et al. |
| 5,629,147 A | * | 5/1997 | Asgari et al. |
| 5,728,527 A | | 3/1998 | Singer et al. |
| 5,776,782 A | * | 7/1998 | Tsuji |
| 5,985,549 A | | 11/1999 | Singer et al. |
| 6,228,592 B1 | * | 5/2001 | Tsuji et al. |
| 6,562,343 B1 | * | 5/2003 | Levinson |

FOREIGN PATENT DOCUMENTS

| | | |
|---|---|---|
| JP | 11-285386 | 10/1999 |
| WO | WO 93/23570 | 11/1993 |
| WO | WO98/13524 | 4/1998 |
| WO | WO98/33897 | 8/1998 |

OTHER PUBLICATIONS

Separation of Cells (1993) pp. 89–94, Ch. 8. Cell Sorting.
J. R. Lakowicz, "Principles of Fluorescence Spectroscopy", Chapter 10, pp. 303–339, (1983), Plenum Press, New York.

J. R. Lakowicz, "Principles of Fluorescence Spectroscopy", Plenum Press, New York, pp. 305–309 (1983).

Cardullo et al., "Detection of Nucleic Acid Hybridization by Nonradiative Fluorescence Resonance Energy Transfer", Proc. Natl. Acad. Sci. USA, vol. 85, pp. 8790–8794, 12/88.

Mergny et al., "Fluorescence Energy Transfer as a Probe for Nucleic Acid Structures and Sequences", Nucleic Acids Research, vol. 22, No. 6, pp. 920–928, 1994.

Sixou et al., "Intracellular Oligonucleotide Hybridization Detected by Fluorescence Resonance Energy Transfer (FRET)", Nucleic Acids Research, vol. 22, No. 4, pp. 662–668, 1994.

Leonetti et al., "Intracellular Distribution of Microinjected Antisense Oligonucleotides", Proc. Natl. Acad. Sci. USA, vol. 88, pp. 2702–2706, 4/91.

Fisher et al., "Intracellular Disposition and Metabolism of Fluorescently–Labeled Unmodified and Modified Oligonucleotides Microinjected into Mammalian Cells", Nucleic Acids Research, vol. 21, No. 16, pp. 3857–3865, 1993.

Sokol et al., "Real Time Detection of DNA–RNA Hybridization in Living Cells", Proc. Natl. Acad. Sci. USA, vol. 95, pp. 11538–11543, 9/98.

Zobel et al., "Cationic Polyhexylcyanoacrylate Nanoparticles as Carriers for Antisense Oligonucleotides", Antisense and Nucleic Acid Drug Development, 7:483–493 (1997).

* cited by examiner

*Primary Examiner*—Ethan Whisenant
(74) *Attorney, Agent, or Firm*—Leydig, Voit & Mayer, Ltd.

(57) ABSTRACT

The present invention provides a method for selectively separating live cells which have expressed a specific mRNA comprising: a first step of introducing a marker which label mRNA into cells in a live cell group containing live cells which have expressed a specific mRNA; a second step of labeling said mRNA with said marker to obtain a live cell group containing live cells having the labeled mRNA; and a third step of detecting said labeled mRNA to identify the live cells having the labeled mRNA and separating the identified live cells selectively from said live cell group obtained in said second step.

2 Claims, 67 Drawing Sheets

Fig.1

```
        10         20         30         40         50
AUCACUCUCUUUAAUCACUACUCACAGUAACCUCAACUCCUGCCACAAUGUACAGGAU 70         80         90        100        110
AACUCCUGUCUUGCAUUGCACUAAGUCUUGCACUUGUCACAAACAGUGCACCUACUUC
              ACGTGATTCAGAACG TGAACAGTGTTTGTC
                  77-91            92-106

130        140        150        160        170
GUUCUACAAAGAAAACACAGCUACAACUGGAGCAUUUACUGCUGGAUUUACAGAUGAU 190        200        210        220        230
UGAAUGGAAUUAAUAAUUACAAGAAUCCCAAACUCACCAGGAUGCUCACAUUUAAGUU
             ATGTTCTTAGGGTTT GAGTGGTCCTACGAG TGTAAATTCAA
                 198-212          213-227         228-242

250        260        270        280        290
ACAUGCCCAAGAAGGCCACAGAACUGAAACAUCUUCAGUGUCUAGAAGAAGAACUCA
TGTACGGGTTCTTCCGG                              TCTTCTTGAGTT
   243-257                                        287-301

310        320        330        340        350
CUCUGGAGGAAGUGCUAAAUUUAGCUCAAAGCAAAAACUUUCACUUAAGACCCAGGGA
GAGACCTCCTTCACGA                        GTGAATTCTGGGTCC CT
  302-316                                    342-356

370        380        390        400        410
UAAUCAGCAAUAUCAACGUAAUAGUUCUGGAACUAAAGGGAUCUGAAACAACAUUCAU
ATTAGTCGTTA
 357-371

430        440        450        460        470
GUGAAUAUGCUGAUGAGACAGCAACCAUUGUAGAAUUUCUGAACAGAUGGAUUACCUU 490        500        510        520        530
GUCAAAGCAUCAUCUCAACACUAACUUGAUAAUUAAGUGCUUCCCACUUAAAACAUAU 550        560        570        580        590        600
GGCCUUCUAUUUAUUUAAAUAUUUAAAUUUUAUAUUUAUUGUUGAAUGUAUGGUUUGCUA 610        620        630        640        650        66(
CCUAUUGUAACUAUUAUUCUUAAUCUUAAAACUAUAAAUAUGGAUCUUUUAUGAUUCUUU 670        680        690        700        710        72(
UUGUAAGCCCUAGGGCUCUAAAAUGGUUUCACUUAUUUAUCCCAAAAUAUUUAUUAUU 730        740        750        760        770        78
UGUUGAAUGUUAAAUAUAGUAUCUAUGUAGAUUGGUUAGUAAAACUAUUUAAUAAAUUU( 790        800
AUAAAUAUAAAAAAAAAAAAAC
```

Fig.2

```
         10        20        30        40        50        60
GAUCGUUAGCUUCUCCUGAUAAACUAAUUGCCUCACAUUGCACUGCAAAUCGACACCUA 70        80        90       100       110       120
UUAAUGGGUCUCACCUCCCAACUGCUUCCCCCUCUGUUCUUCCUGCUAGCAUGUGCCGGC
        |GAGTGGAGGGTTGAC|GAAGGGGGAGACAAG|                 |CG|
            70-84           85-99

130       140       150       160       170       180
AACUUUGUCCACGGACACAAGUGCGAUAUCACCUUACAGGAGAUCAUCAAAACUUUGAAC
|TTGAAACAGGTGC|CTGTGTTCACGCTAT|                          |ACTTG|
   119-133         134-148

190       200       210       220       230       240
AGCCUCACAGAGCAGAAGACUCUGUGCACCGAGUUGACCGUAACAGACAUCUUUGCUGCC
|TCGGAGTGTC|TCGTCTTCTGAGACA|
 176-190      191-205

250       260       270       280       290       300
UCCAAGAACACAACUGAGAAGGAAACCUUCUGCAGGGCUGCGACUGUGCUCCGGCAGUUC
                         |TGGAAGACGTCCCGA|CGCTGACACGAGGCC|
                             265-279         280-294

310       320       330       340       350       360
UACAGCCACCAUGAGAAGGACACUCGCUGCCUGGGUGCGACUGCACAGCAGUUCCACAGG 370       380       390       400       410       420
CACAAGCAGCUGAUCCGAUUCCUGAAACGGCUCGACAGGAACCUCUGGGGCCUGGCGGGC
            |GCTAAGGACTTTGCC|GAGCTGTCCTTGGAG|
                376-390          391-405

430       440       450       460       470       480
UUGAAUUCCUGUCCUGUGAAGGAAGCCAACCAGAGUACGUUGGAAAACUUCUUGGAAAGG 490       500       510       520       530       540
CUAAAGACGAUCAUGAGAGAGAAAUAUUCAAAGUGUUCGAGCUGAAUAUUUUAAUUUAUG 550       560       570       580       590       600
AGUUUUUGAUAGCUUUAUUUUUUAAGUAUUUAUAUAUUUAUAACUCAUCAUAAAAUAAAG

610
UAUAUAUAGAAUCUAAAA
```

IL-2 342-356

RATIO OF AREAS   79.7% : 22.8%

IL-2 357-371

RATIO OF AREAS   72.7% : 27.3%

| Culture time (h) [1] | 0 | 24 | 48 | 72 | 96 |
|---|---|---|---|---|---|
| IL-2 secretion [2] (pg/ml/10$^7$ cells) | <0.32 | 1032±25 | 2433±533 | 2688±194 | 2531±283 |
| IL-2 mRNA detection [3] | | | | | |
| (√4×10$^6$ cells) | | | | | |
| (√1×10$^6$ cells) | | | | | |
| (√2.5×10$^5$ cells) | | | | | |
| IL-2 molecules / cell [4] (×10$^4$/cell) | <0.29×10$^{-4}$ | 0.76±0.17 | 1.11±0.40 | 1.22±0.67 | 1.20±0.28 |

[1] Time after adding 10 nM PMA, 0.5 mg/ml anti-human CD3 antibody and anti-human CD28 antibody to cultured Jurkat E6-1 cells

[2] The concentration of IL-2 in the culture supernatants measured by ELISA using anti-human IL-2 antibody

[3], [4] Determination of cellular IL-2 expression level by dot blotting using RNA probe complementary to human IL-2 mRNA

Fig.21

| PROBE | IL-2 EXPRESSION | |
|---|---|---|
| | (+) | (−) |
| IL-2 228-242(D) | | |
| IL-2 243-257(A) | | |
| IL-2 198-212(D) | | |
| IL-2 213-227(A) | | |
| IL-2 77-91(D) | | |
| IL-2 92-106(A) | | |
| IL-2 287-301(D) | | |
| IL-2 302-316(A) | | |
| IL-2 342-356(D) | | |
| IL-2 357-371(A) | | |
| NONE | | |

Fig.86

IL-2 mRNA (+); 5/24

IL-4 mRNA (+); 3/43

Fig. 87

| IL-2 mRNA (+); 11/11 | γ-IF mRNA (+); 14/14 | TNF-β mRNA (+); 11/11 |
| --- | --- | --- |
| IL-4 mRNA (+); 0/10 | IL-5 mRNA (+); 0/11 | IL-10 mRNA (+); 0/9 |

Fig.88
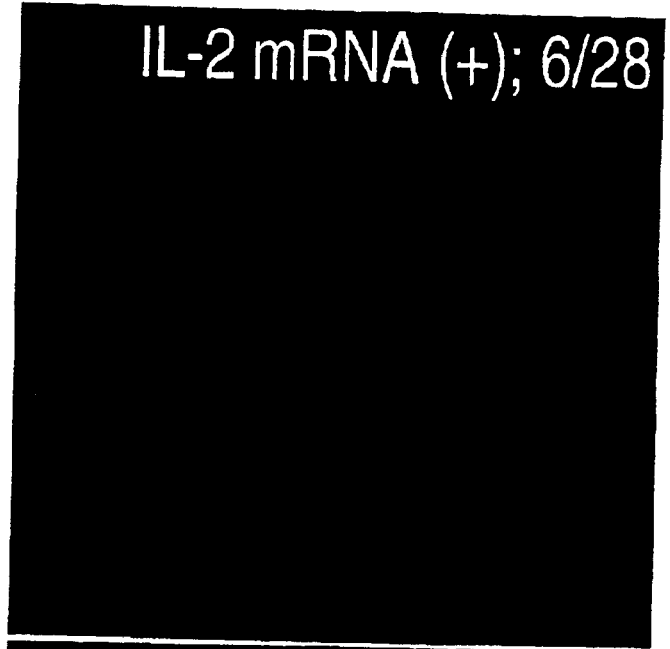
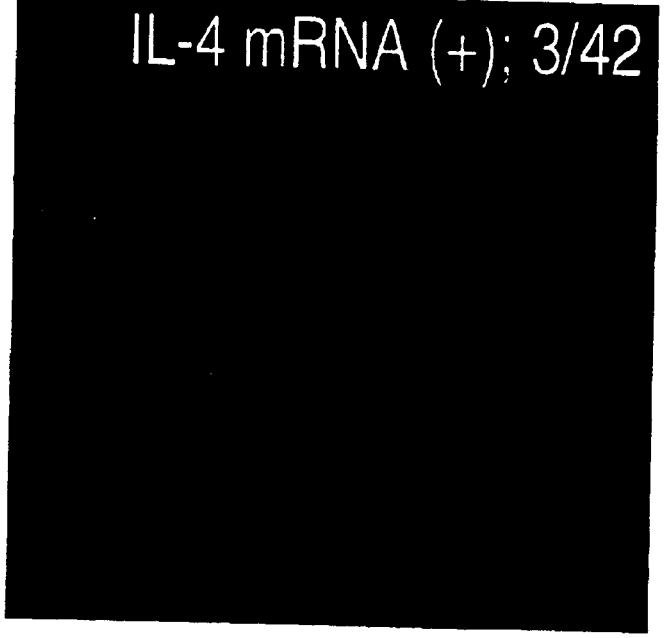

Fig. 91

| IL-2 mRNA (+); 10/10 | γ-IF mRNA (+); 9/9 | TNF-β mRNA (+); 9/9 |
| --- | --- | --- |
| IL-4 mRNA (+); 0/9 | IL-5 mRNA (+); 0/8 | IL-10 mRNA (+); 0/9 |

Fig. 93

| IL-2 mRNA (+); 0/7 | γ-IF mRNA (+); 0/8 | TNF-β mRNA (+); 0/8 |
| --- | --- | --- |
| IL-4 mRNA (+); 9/9 | IL-5 mRNA (+); 10/10 | IL-10 mRNA (+); 9/9 |

SEQUENCE LISTING

<160> NUMBER OF SEQ ID NOS: 20

<210> SEQ ID NO 1
<211> LENGTH: 15
<212> TYPE: DNA
<213> ORGANISM: Artificial Sequence
<220> FEATURE:
<223> OTHER INFORMATION: Probe

<400> SEQUENCE: 1
gtaaaactta aatgt                                                      15

<210> SEQ ID NO 2
<211> LENGTH: 15
<212> TYPE: DNA
<213> ORGANISM: Artificial Sequence
<220> FEATURE:
<223> OTHER INFORMATION: Probe

<400> SEQUENCE: 2
ggccttcttg ggcat                                                      15

<210> SEQ ID NO 3
<211> LENGTH: 15
<212> TYPE: DNA
<213> ORGANISM: Artificial Sequence
<220> FEATURE:
<223> OTHER INFORMATION: Probe

```
<400> SEQUENCE: 3
tttgggattc ttgta                                                    15

<210> SEQ ID NO 4
<211> LENGTH: 15
<212> TYPE: DNA
<213> ORGANISM: Artificial Sequence
<220> FEATURE:
<223> OTHER INFORMATION: Probe

<400> SEQUENCE: 4
gagcatcctg gtgag                                                    15

<210> SEQ ID NO 5
<211> LENGTH: 15
<212> TYPE: DNA
<213> ORGANISM: Artificial Sequence
<220> FEATURE:
<223> OTHER INFORMATION: Probe

<400> SEQUENCE: 5
gcaagactta gtgca                                                    15

<210> SEQ ID NO 6
<211> LENGTH: 15
<212> TYPE: DNA
<213> ORGANISM: Artificial Sequence
<220> FEATURE:
<223> OTHER INFORMATION: Probe

<400> SEQUENCE: 6
ctgtttgtga caagt                                                    15

<210> SEQ ID NO 7
<211> LENGTH: 15
<212> TYPE: DNA
<213> ORGANISM: Artificial Sequence
<220> FEATURE:
<223> OTHER INFORMATION: Probe

<400> SEQUENCE: 7
ggtttgagtt cttct                                                    15

<210> SEQ ID NO 8
<211> LENGTH: 15
<212> TYPE: DNA
<213> ORGANISM: Artificial Sequence
<220> FEATURE:
<223> OTHER INFORMATION: Probe

<400> SEQUENCE: 8
agcacttcct ccaga                                                    15

<210> SEQ ID NO 9
<211> LENGTH: 15
<212> TYPE: DNA
<213> ORGANISM: Artificial Sequence
<220> FEATURE:
<223> OTHER INFORMATION: Probe

<400> SEQUENCE: 9
cctgggtctt aagtg                                                    15

<210> SEQ ID NO 10
<211> LENGTH: 15
```

```
<212> TYPE: DNA
<213> ORGANISM: Artificial Sequence
<220> FEATURE:
<223> OTHER INFORMATION: Probe

<400> SEQUENCE: 10
attgctgatt aagtc                                                        15

<210> SEQ ID NO 11
<211> LENGTH: 15
<212> TYPE: DNA
<213> ORGANISM: Artificial Sequence
<220> FEATURE:
<223> OTHER INFORMATION: Probe

<400> SEQUENCE: 11
cagttgggag gtgag                                                        15

<210> SEQ ID NO 12
<211> LENGTH: 15
<212> TYPE: DNA
<213> ORGANISM: Artificial Sequence
<220> FEATURE:
<223> OTHER INFORMATION: Probe

<400> SEQUENCE: 12
gaacagaggg ggaag                                                        15

<210> SEQ ID NO 13
<211> LENGTH: 15
<212> TYPE: DNA
<213> ORGANISM: Artificial Sequence
<220> FEATURE:
<223> OTHER INFORMATION: Probe

<400> SEQUENCE: 13
cgtggacaaa gttgc                                                        15

<210> SEQ ID NO 14
<211> LENGTH: 15
<212> TYPE: DNA
<213> ORGANISM: Artificial Sequence
<220> FEATURE:
<223> OTHER INFORMATION: Probe

<400> SEQUENCE: 14
tatcgcactt gtgtc                                                        15

<210> SEQ ID NO 15
<211> LENGTH: 15
<212> TYPE: DNA
<213> ORGANISM: Artificial Sequence
<220> FEATURE:
<223> OTHER INFORMATION: Probe

<400> SEQUENCE: 15
ctgtgaggct gttca                                                        15

<210> SEQ ID NO 16
<211> LENGTH: 15
<212> TYPE: DNA
<213> ORGANISM: Artificial Sequence
<220> FEATURE:
<223> OTHER INFORMATION: Probe

<400> SEQUENCE: 16
```

```
acagagtctt ctgct                                                15

<210> SEQ ID NO 17
<211> LENGTH: 15
<212> TYPE: DNA
<213> ORGANISM: Artificial Sequence
<220> FEATURE:
<223> OTHER INFORMATION: Probe

<400> SEQUENCE: 17
agccctgcag aaggt                                                15

<210> SEQ ID NO 18
<211> LENGTH: 15
<212> TYPE: DNA
<213> ORGANISM: Artificial Sequence
<220> FEATURE:
<223> OTHER INFORMATION: Probe

<400> SEQUENCE: 18
ccggagcaca gtcgc                                                15

<210> SEQ ID NO 19
<211> LENGTH: 15
<212> TYPE: DNA
<213> ORGANISM: Artificial Sequence
<220> FEATURE:
<223> OTHER INFORMATION: Probe

<400> SEQUENCE: 19
ccgtttcagg aatcg                                                15

<210> SEQ ID NO 20
<211> LENGTH: 15
<212> TYPE: DNA
<213> ORGANISM: Artificial Sequence
<220> FEATURE:
<223> OTHER INFORMATION: Probe

<400> SEQUENCE: 20
gaggttcctg tcgag                                                15
```

METHOD FOR SELECTIVELY SEPARATING LIVE CELLS EXPRESSING A SPECIFIC GENE

BACKGROUND OF THE INVENTION

1. Field of the Invention

This invention relates to a method for selectively separating live cells which have expressed a specific gene.

2. Related Background Art

In the case that the translation products of a gene are cell surface molecules, a method for selectively separating cells which have expressed the specific gene, while being viable, is to make fluorescence labeled antibodies bind to the surface molecules for labeling the cells fluorescently, to identify fluorescing cells by flow cytometry, and to separate the identified cells with a cell sorter (Fluorescence Activated Cell Sorter, FACS). In addition, the panning method is also known wherein only the objective cells are absorbed on the bottom surface of a dish over which is covered with antibodies specifically binding to the cell surface molecules.

In the case that the translation products of a gene are not cell surface molecules but localize in the cells (in the cytoplasm or in organella), the method described above cannot be adopted. In this case, it is theoretically possible to fluorescently label the gene-expressing cells by introduction of fluorescence-labeled antibodies that are specific to the molecules localized in the cells into the cells, through microinjection and to separate the objective gene-expressing cells with the cell sorter described above based on the difference in fluorescence intensity of the cells with irradiation of laser beam or the like.

However, for the cell labeling method by microinjection described above, the method can not label many cells at once. The number of the cells to which the labeled antibodies can be introduced for one experiment is at most ten or less. In addition, it is not easy to introduce the solution of a polymer with the molecular weight greater than 120,000 like an antibody with high concentration into the cell because of its high viscosity. Therefore, microinjection is impractical to label the sufficient number of objective cells efficiently.

In the case that the translation products of the gene are not cell surface molecules, but molecules that are liberated into the extracellular fluid and that do not remain in the cell or near the cell membrane, it is very difficult to selectively trap the molecules to separate the cells expressing the specific gene, from other molecules with the approaches described above. This is because, during the process where polypeptide chains generated based on the genetic information are folded and secreted, their structure changes gradually and from time to time to prevent any known antibodies from binding to the polypeptide chains within or on the surfaces of live cells efficiently. Also, even in the case that the translation products are present on the surfaces of cells, it is difficult to selectively separate the cells unless the molecules are specifically present on the surfaces of particular cells.

A typical example, where the situation described above exists and when it is difficult to separate the objective live cells selectively, includes the case where cells secreting a specific cytokine are selectively separated using the cytokine as a selection marker.

When an antigen invades an organism, helper T cells (CD4+T cells) that recognize the antigen as a foreign matter are activated, and then they will be differentiated into TH1 and TH2, which have different immune functions from each other. TH1 (T Helper 1) which is responsible for cellular immune functions, e.g. activation of macrophages to remove foreign matters by phagocytosis; and TH2 (T Helper 2) which has humoral immune functions, e.g., activation of B cells to produce antibody molecules to neutralize foreign matters and (See FIG. 94). TH1 and TH2 produce cytokines, interleukin-2 (IL-2) and interleukin-4 (IL-4), respectively. In the healthy state, TH1 and TH2 control each other's functions and keep a balance. However, once this relationship is disrupted, it causes various infections or autoimmune disorders.

If TH1 or TH2 can be selectively separated and obtained, it will be medically important, because their application can be contemplated in supplementing immune functions or the like. Thus, a variety of attempts have been made to find molecules that are present on the surface of TH1 or TH2, that can be used for their separation and obtaining.

For example, it has been reported that the tissue infiltration which is dependent on adhesive molecules, P- and E-selectin, is observed specifically with human TH1 (Austrup, F. et al. Nature, 385, 81–83, 1997). This suggests that ligands adhering specifically to the selections are present on TH1 cell surfaces. However, when reactivity for P- and E-selectin is examined by flow cytometry, the results are TH1:TH2=131:52 for P-selectin, and TH1:TH2=668:88 for E-selectin; therefore, the specificity is not complete. These results can be interpreted as reflecting the fact that particularly notable P- and E-selection ligand expression is induced in TH1 under physiological conditions unique to inflamed tissues (such as skin and joints).

Receptors for CC-chemokine (CCR3), eotaxin, have also been reported to be present with approximate specificity on human TH2 cell surfaces (Sallusto, F. et al. Science, 277, 1997). However, since CCR3-negative T cell groups also include IL-4 producing TH2 cells in a proportion of 1.9%, the specificity is not complete. Furthermore, the presence of many more of the same receptors on eosinophil and basophil cell surfaces than on TH2 raises the risk of possible contamination by cells other than TH2 if CCR3+ cells are simply separated from T lymphocytes that have been crudely purified from blood.

The receptor CCR5 for other CC-chemokines such as MIP-1β and IP10 and the receptor CXCR3 for the CXC-chemokine SDF-1 have been reported to be present with approximate specificity on human TH1 cell surfaces (Loestscher, P. et al., Nature, 391, 344, 1998). However, since one of the nine TH2 clones obtained here was CCR5+, the specificity is not complete. Furthermore, while TH1 shows higher CXCR3 gene expression and CXC-chemokine dependent migration than TH2, CXCR3 gene expression was also confirmed in all of the TH2 clones examined, and therefore, the specificity is not complete. Moreover, CCR5 and CXCR3 are also present on neutrophil cell surfaces, and therefore the risk exists of possible contamination by neutrophils in CCR5+ or CXCR3+ cells separated from T lymphocytes that have been crudely purified from blood.

In addition, IL-12 (interleukin-12) receptor (IL-12R) has been reported to be present with approximate specificity on human TH1 cell surfaces (Rogge, L. et al., J. Exp. Med., 185, 825, 1997). However, while TH1 cell surfaces bear high affinity receptors (Kd value=27 pM) and low affinity receptors (Kd value=5 nM) for IL-12 at 140 molecules and 450 molecules per cell surface, respectively, similar low affinity receptors (Kd value=2 nM) are also present on TH2 cells at 200 molecules per cell surface. This means that IL-12R cannot be used as a definitive TH1 cell surface marker. Moreover, since IL-12R is also present on the cell surfaces of NK cells, the risk exists of possible contamination by NK cells in IL-12R positive cells separated from T lymphocytes that have been crudely purified from blood.

IL-18 (interleukin-18) receptor (IL-18R) is another receptor reported to be present specifically on the cell surface of a TH1 clone established from transgenic mice with T cell receptors for ovalbumin (Xu, D. et al., J. Exp. Med., 188, 1485, 1998). However, like IL-18R, the ST2L molecule belonging to the interleukin-1 receptor (IL-1R) family is also known to be present on TH2 cell surfaces. Because gene homology within the IL-1R family is particularly high in humans, IL-18R cannot be considered a definitive cell surface marker in humans and no reports have yet been published on their presence specifically on TH1 cell surfaces. Also, since IL-18R is much more abundantly present on monocyte, neutrophil and NK cell surfaces than on TH1, the risk exists of possible contamination by cells other than TH1 in IL-18R positive cells separated from T lymphocytes that have been crudely purified from blood.

The reports cited above suggested that receptors for cytokines, chemokines and the like present on TH1 or TH2 cell surfaces vary considerably in terms of amount (number of per cell surface) and quality (affinity of the receptors for their ligands or intracellular transduction of stimuli upon binding to ligands), and that the distribution of such receptors therefore highly favors either TH1 or TH2. The reason for the favorableness of cell surface molecules toward either TH1 or TH2 is believed to arise from the biological environment (physiological conditions) surrounding the helper T cells.

For example IL-12, which is one of the ligands for these cytokine receptors, is a cytokine secreted by macrophages, etc. upon initial infection (Walker, W. et al., J. Immunol., 162, 5894, 1999), and IL-18 is also known to be produced by activated macrophages and Kupffer cells (Yoshimoto, T. et al., J. Immunol., 161, 3400, 1998). Naturally, both of these cytokines have more connections with TH1 than with TH2, in light of the cellular immunity function of the former, and they are considered to be factors that perform transduction of physiological information from macrophages to TH1 (i.e., that activate TH1 in the body).

This suggests a connection between activation of macrophages by TH1 and reception of stimuli (IL-12 and IL-18) returned from macrophages, whereby macrophages activated by TH1 eliminate foreign matters in the body while also activating TH1. As this interdependent relationship is established at sites of inflammation in the body, it is fully expected for the number of receptors for IL-12 and IL-18 and the activity of the receptor molecules to increase significantly on TH1 cell surfaces. Further, since TH2 cells are not exposed to the same conditions in the body as TH1, it is surmised that they have no need to receive IL-12 or IL-18. However, as long as IL-12 or IL-18 receptors are detected even slightly on TH2 cell surfaces, it cannot be denied that TH2 also has the potential to respond to IL-12 or IL-18.

It is therefore inconceivable that these cytokine receptors are definitive markers that can distinguish TH1 from among TH1 and TH2. In addition, since these chemokine and cytokine receptors that are predominantly distributed on TH1 and TH2 cells are also found distributed among other cell types such as NK cells, they are considered impractical as markers for distinguishing TH1 or TH2 from each other in blood samples. For example, cell specimens containing CD4+ cells (helper T cells) that are separated and purified by common methods from blood samples taken from humans usually include contamination by monocytes and granulocytes, and these false positive cells may be expected to be mistaken for TH1 or TH2.

As stated above, it is, therefore, very difficult to selectively separate TH1 and TH2 cells based on surface molecules. Moreover, since the cytokines (IL-2 and IL-4) produced by TH1 and TH2 do not remain in the cell or near the cell membrane but are liberated into the extracellular fluid, it is difficult to selectively separate TH1 and TH2 using these cytokines.

SUMMARY OF THE INVENTION

The present invention has been made in consideration of the above-stated problems in the prior art. It is an object of the present invention to provide a separation method which allows one to selectively separate and obtain the objective cells, that is, the cells which have expressed a specific gene, when there are no cell surface molecules usable as markers in the cell, or when the cell surface molecules cannot be distinguished from each other even if they are present in the cell, or even when the molecules to be the markers are liberated into the extracellular fluid.

The present inventors have found that the problems in the prior art as described above result from the fact that the translation products of a specific gene (polypeptide) are used as targets (or markers) to separate gene-expressed cells. Based on this finding, the inventors pursued further research, and as a result, have found that if mRNA is used as a target (marker) which exists mainly on float in the cytoplasm and which is a transcriptional product of a gene instead of using the translation product (polypeptide) as a marker, it is possible to selectively separate the cells which have expressed a specific gene, while being viable, when there are no cell surface molecules usable as markers in the cell, or when the cell surface molecules are not ones which are strictly specific for the objective cells, or even when the molecules to be the markers are liberated into the extracellular fluid. The present invention has thus been accomplished.

Specifically, the present invention provides a method for selectively separating live cells which have expressed a specific gene comprising:

a first step of introducing a marker capable of labeling mRNA into cells in a live cell group containing live cells which have expressed a specific mRNA;

a second step of labeling the mRNA with the marker to obtain a live cell group containing live cells having the labeled mRNA; and a third step of detecting the labeled mRNA to identify the live cells having the labeled mRNA and separating the identified live cells selectively from the live cell group obtained in the second step.

In the method for selectively separating live cells which have expressed a specific gene according to the present invention, it is preferable that the marker in the first step is a probe which has a base sequence complementary to the mRNA and has been labeled with a fluorescent dye, the labeled mRNA in the second step is a hybrid of the probe and the mRNA, and the selective separation in the third step is performed by irradiating light to the live cell group containing live cells having the hybrid, identifying live cells which cause a change in fluorescence of said fluorescent dye based on formation of the hybrid, and separating the identified live cells from the live cell group.

It is also preferable that the probe comprises a first probe and a second probe, the first probe and the second probe have base sequences capable of hybridizing to the mRNA adjacently, the first probe is labeled with an energy donor fluorescent dye and the second probe is labeled with an energy acceptor fluorescence dye, and the change in fluorescence is caused by fluorescence resonance energy transfer (FRET) from the energy donor fluorescence dye of the first probe to the energy acceptor fluorescence dye of the second probe.

In addition, in the method for selectively separating live cells which have expressed a specific gene according to the present invention, it is preferable that the selective separation in the third step of the live cells based on the changes in fluorescence is performed by a cell sorter (FACS).

It is also preferable that the mRNA is an mRNA encoding a cytokine. It is more preferable that the mRNA is an mRNA encoding interleukin-2 (IL-2) and the first probe is a probe having a base sequence set forth in SEQ ID NO: 9 in the Sequence Listing and further that the second probe is a probe having a base sequence set forth in SEQ ID NO: 10 in the Sequence Listing.

It is also preferable that the mRNA is an mRNA encoding interleukin-4 (IL-4) and the first probe is a probe having a base sequence set forth in SEQ ID NO: 17 in the Sequence Listing and further that the second probe is a probe having a base sequence set forth in SEQ ID NO: 18 in the Sequence Listing.

In the present invention, it is preferable that the live cells selectively separated in the third step are T Helper 1 (TH1) or T Helper 2 (TH2) cells.

As stated above, according to the present invention it will become possible to provide a separation method which allows one to selectively separate and obtain the objective cells, that is, the cells which have expressed a specific gene, when there are no cell surface molecules usable as markers in the cell, or when the cell surface molecules 11, or even when the molecules to be the markers are liberated into the extracellular fluid.

The present invention will become more fully understood from the detailed description given hereinbelow and the accompanying graphs which are given by way of illustration only, and thus are not to be considered as limiting the present invention. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The file of this patent contains at least one drawing executed in color. Copies of this patent with color drawings (s) will be provided by the Patent and Trademark Office upon request and payment of the necessary fee.

FIG. 1 is a listing of the entire base sequence of IL-2 mRNA and the base sequences of oligo DNA probes.

FIG. 2 is a listing of the entire base sequence of IL-4 mRNA and the base sequences of oligo DNA probes.

FIG. 19 is a graph showing the amount of IL-2 secreted by Jurkat E6-1 cells associated with the expression induction treatment of IL-2, fluorescence micrographs obtained when IL-2 mRNA in the cell extract was fluorescently detected, and the number of molecules of the intracellular IL-2 mRNA.

FIG. 21 is a set of fluorescence micrographs obtained when hybrids were formed between IL-2 mRNA in the IL-2 expression-induced cells or IL-2 expression-uninduced cells in the fixed state and various probes (non-fluorescent markers), and the hybrids were fluorescently detected.

FIG. 86 is a set of fluorescence micrographs obtained when the cell group of CD4+ cells (helper T cells) of FIG. 60 before flow cytometry thereof was fixed to the bottom of a cover glass chamber, hybrids were formed between the IL-2 mRNA or IL-4 mRNA of the fixed cells and RNA probe for IL-2 RNA s or IL-4 RNA probes, respectively, and the hybrids were fluorescently detected.

FIG. 87 is a set of fluorescence micrographs obtained when the cell group of cells selectively separated with the cell sorter in FIG. 61 was fixed to the bottom of a cover glass chamber, hybrids were formed between the IL-2, γ-IF, TNF-β, IL-4, IL-5 or IL-10 mRNA of the fixed cells and IL-2, γ-IF, TNF-β, IL-4, IL-5 or IL-10 RNA probe, respectively, and the hybrids were fluorescently detected.

FIG. 88 is a set of fluorescence micrographs obtained when the cell group of CD4+ cells (helper T cells) of FIG. 68 before flow cytometry thereof was fixed to the bottom of a cover glass chamber, hybrids were formed between the IL-2 mRNA or IL-4 mRNA of the fixed cells and RNA probe for IL-2 RNA s or IL-4 RNA probes, respectively, and the hybrids were fluorescently detected.

FIG. 91 is a set of fluorescence micrographs obtained when the cell group of cells selectively separated with the cell sorter in FIG. 75 was fixed to the bottom of a cover glass chamber, hybrids were formed between the IL-2, γ-IF, TNF-β, IL-4, IL-5 or IL-10 mRNA of the fixed cells and IL-2, γ-IF, TNF-β, IL-4, IL-5 or IL-10 RNA probes, respectively, and the hybrids were fluorescently detected.

FIG. 93 is a set of fluorescence micrographs obtained when the cell group of cells selectively separated with the cell sorter in FIG. 81 was fixed to the bottom of a cover glass chamber, hybrids were formed between the IL-2, γ-IF, TNF-β, IL-4, IL-5 or IL-10 mRNA of the fixed cells and IL-2, γ-IF, TNF-β, IL-4, IL-5 or IL-10 RNA probes, respectively, and the hybrids were fluorescently detected.

DESCRIPTION OF THE PREFERRED EMBODIMENTS

Figure 3:
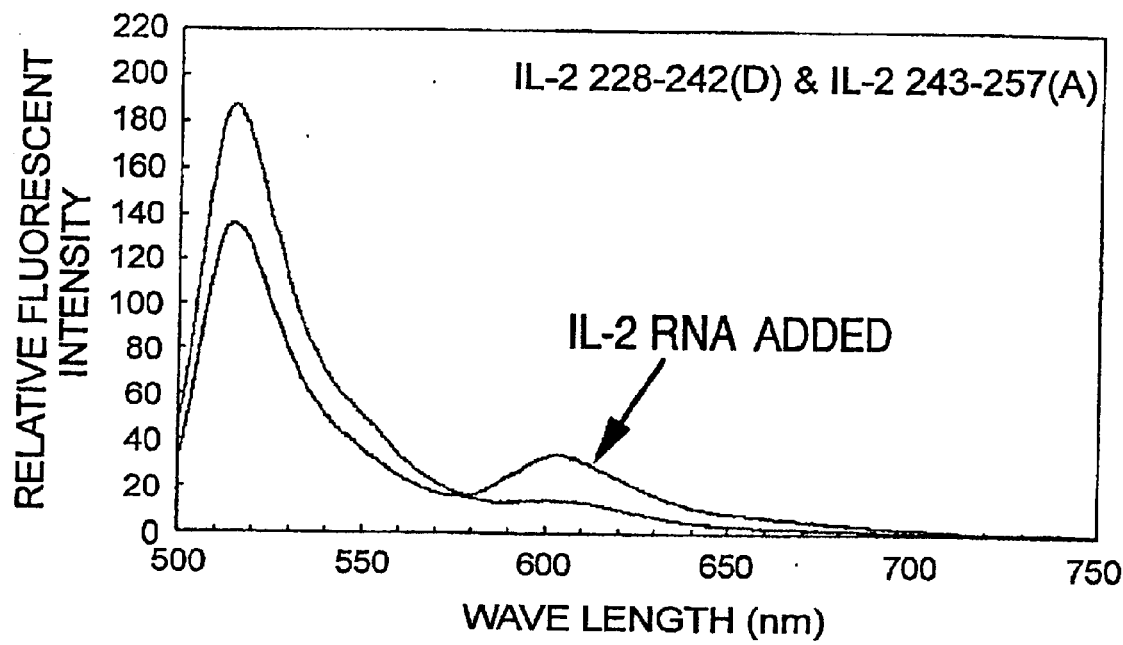
FIG. 3 is a graph of a fluorescence spectrum of a hybrid formed by the donor probe 228–242(D) and the acceptor probe 243–257(A) being adjacently hybridized to IL-2 RNA.
Figure 4:
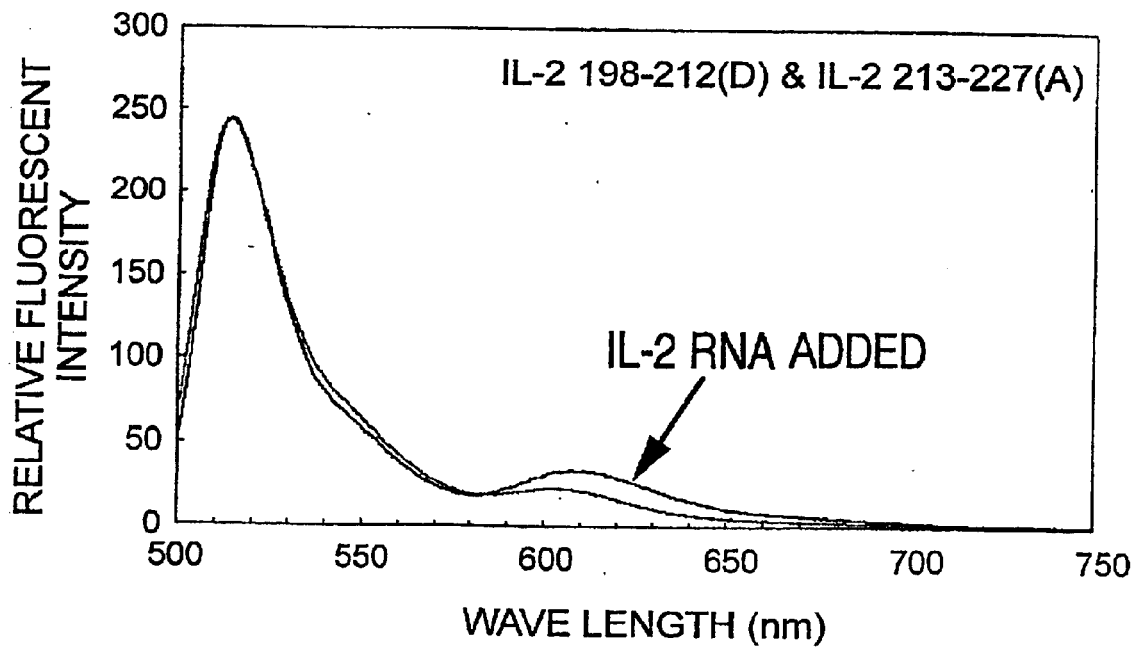
FIG. 4 is a graph of a fluorescence spectrum of a hybrid formed by the donor probe IL-2 198–212(D) and the acceptor probe IL-2 213–227(A) being adjacently hybridized to IL-2 RNA.
Figure 5:
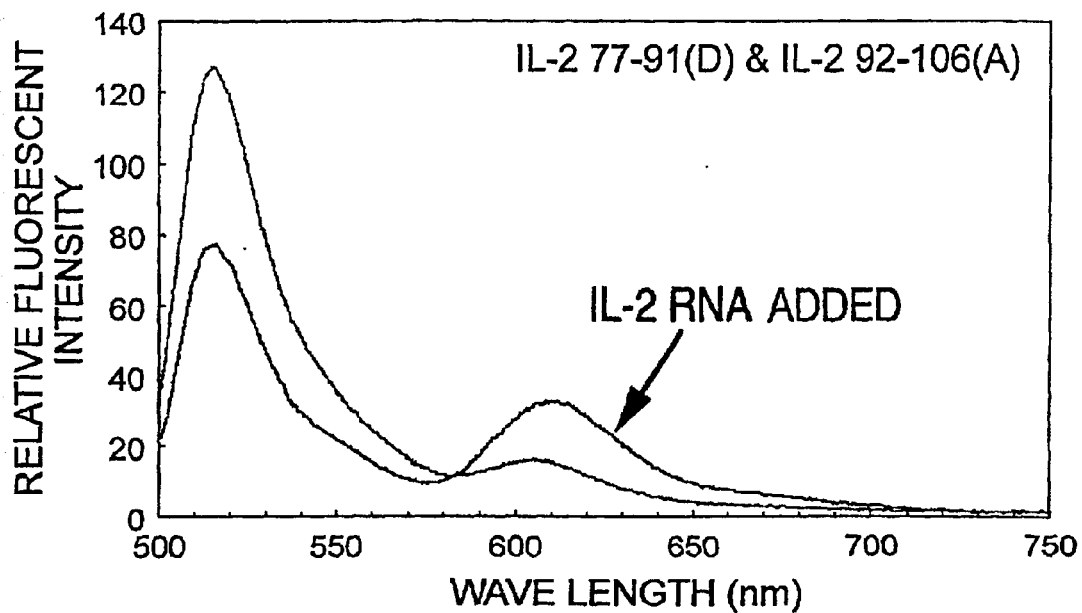
FIG. 5 is a graph of a fluorescence spectrum of a hybrid formed by the donor probe IL-2 77–91(D) and the acceptor probe IL-2 92–106(A) being adjacently hybridized to IL-2 RNA.
Figure 6:
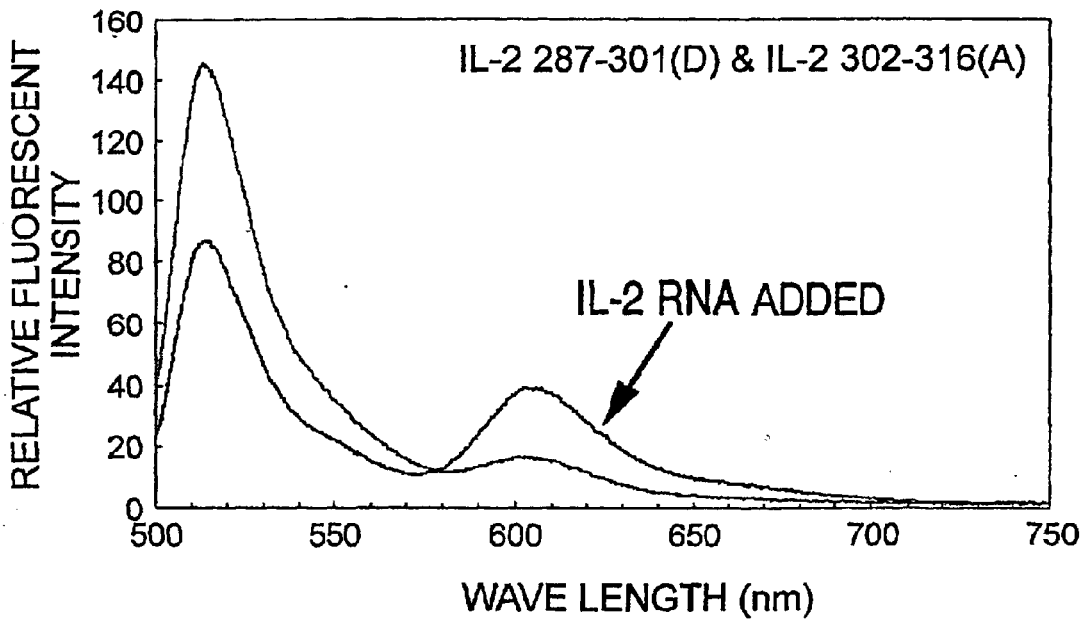
FIG. 6 is a graph of a fluorescence spectrum of a hybrid formed by the donor probe IL-2 287–301(D) and the acceptor probe IL-2 302–316(A) be adjacently hybridized to IL-2 RNA.
Figure 7:
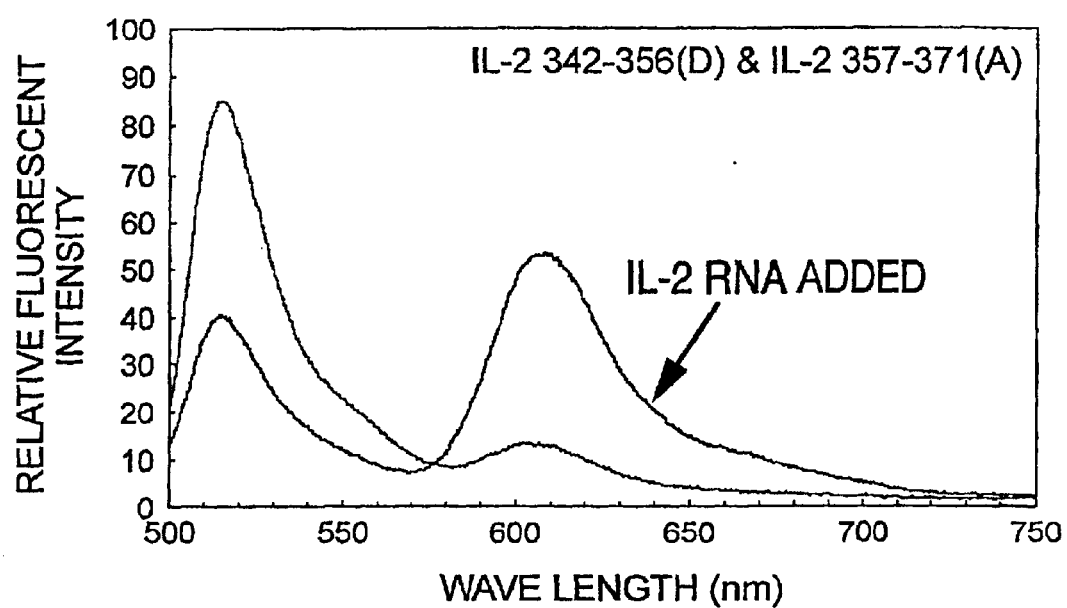
FIG. 7 is a graph of a fluorescence spectrum of a hybrid formed by the donor probe IL-2 342–356(D) and the acceptor probe IL-2 357–371(A) being adjacently hybridized to IL-2 RNA.
Figure 8:
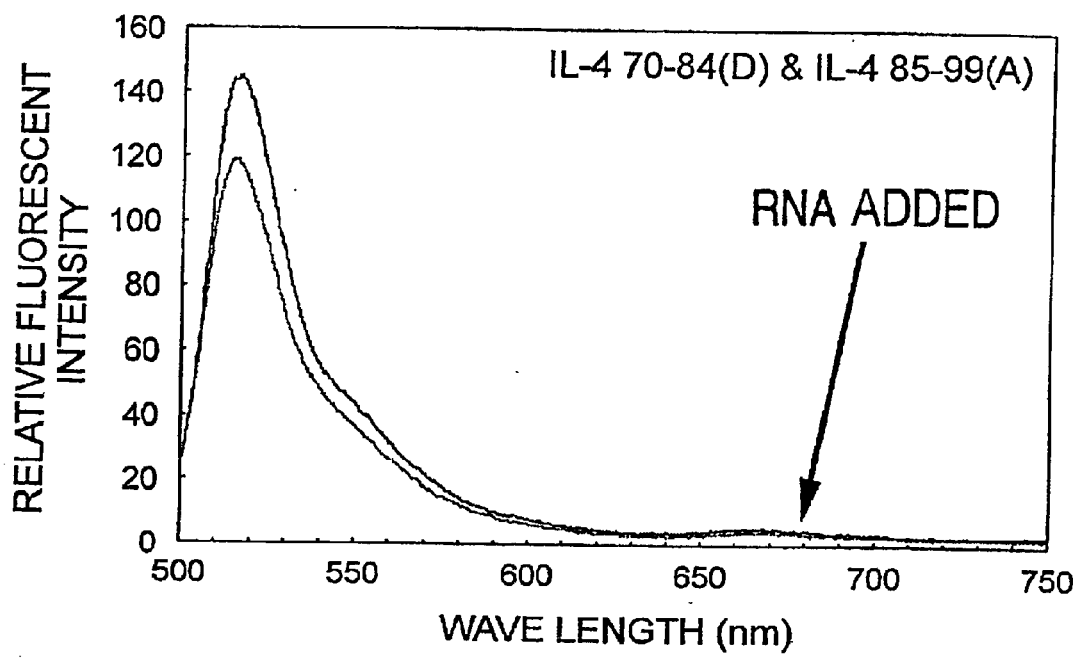
FIG. 8 is a graph of a fluorescence spectrum of a hybrid formed by the donor probe IL-4 70–84(D) and the acceptor probe IL-4 85–99(A) being adjacently hybridized to IL-4 RNA.

The method for selectively separating live cells which have expressed a specific gene according to the present invention comprises:

a first step of introducing a marker capable of labeling mRNA into cells in a live cell group containing live cells which have expressed a specific gene;

a second step of labeling said mRNA with said marker to obtain a live cell group containing live cells having the labeled mRNA; and a third step of detecting said labeled mRNA to identify the live cells having the labeled mRNA and separating the identified live cells selectively from the said live cell group obtained in the said second step.

Markers to be introduced into the cells in the present invention may be those which can label mRNA and are not particularly limited. The marker produces labeled mRNA when it binds to mRNA in the cell. When mRNA does not exist in the cell, or when the marker is excessively introduced even when mRNA is present, the marker which does not involve a bond with mRNA may remain in the cell. Then, the markers are preferably detectable only when they have been bound to mRNA, or are those which can be detected to determine whether they have bound to mRNA or not.

In the present invention, probes which have base sequences complementary to mRNA and which are labeled with a fluorescent dye (hereinafter called "fluorescence-labeled probe" in some cases) are preferably used as markers. These probes form hybrid with the mRNA in the cell. However, there are some probes which do not form hybrids in the cell, and it is necessary to detect the probes forming hybrids selectively as described above. Then, it is preferable to use, as the present probes, those which cause fluorescence changes based on the formation of hybrids.

For these probes described above, two kinds of probes labeled with different fluorescent dyes from each other are used as a pair. In other words, it is preferred to use a probe comprising a first probe and a second probe: the first probe and the second probe have base sequences hybridizable with the mRNA adjacently; the first probe is labeled with an energy donor fluorescent dye, and the second probe is labeled with an energy acceptor fluorescent dye.

When the energy donor fluorescent dye which labels the first probe and the energy acceptor fluorescent dye which labels the second probe are brought close to each other at a proper distance (for example, less than 8 nm), fluorescence resonance energy transfer (FRET) will be possible. Therefore, two fluorescent dyes in probe should be preferably placed at a distance which allows FRET to occur between the energy donor fluorescent dye and the energy acceptor fluorescent dyes when the three molecules, the first probe, the second probe and the mRNA form a hybrid. The preferable distance between two types of fluorescent dye in the formed hybrid depends on the kinds of fluorescent dye and sites of hybridization on mRNA. However, the distance between the two fluorescent dyes is preferably within 20 bases or less, more preferably within 2–4 bases. When probes which can generate FRET are designed, for example, Lakowicz, J. R. "Principles of Fluorescence spectroscopy" (1983), Plenum press, New York may be referred to.

Energy donor fluorescent dyes which may be used in the present invention include 4,4-difluoro-1,3,5,7-tetramethyl-4-bora-3a,4a-diaza-s-indacene-8-propionic acid and derivatives thereof (for example, Bodipy 493/503 or Bodipy FL available from Molecular Probes); tetramethylrhodamine-5-(and-6)isothiocyanate) (TRITC) and derivatives thereof (available from Molecular Probes).

Energy acceptor fluorescent dyes which may be used in the present invention include 1,1'-bis($\epsilon$-carboxypentyl)-3,3,31,3'-tetramethyl indodicarbocyanine-5,5'-disulfonate potassium salt and derivatives thereof (for example, Cy3 or Cy5, available from Amersham Pharmacia BioTech). X-rhodamine-5-(and-6)-isothiocyanate (XRITC) and derivatives thereof (available from Molecular Probes); 6-(((4,4-difluoro-5-(2-thienyl)-4-bora-3a,4a-diaza-s-indacene-3-yl)styryloxy)acetyl)aminohexanoic acid and derivatives thereof (for example, Bodipy 630/650 or Bodipy 650/665, available from Molecular Probes).

In the present invention, it is preferable to use Bodipy 493/503 as an energy donor fluorescent dye, and Cy5 or XRITC as an energy acceptor fluorescent dye.

In the present invention, the number of bases of oligonucleotide to form a probe is not strictly limited. When the number of bases is extremely small, e.g., less than 10, it will, however, likely be difficult to form a fully stable hybrid. When the number of bases in a probe is large exceeding 50, not only the synthesis of the probe is difficult, but also the stability of the probe is degraded; and it can take a longer time to form a hybrid.

The number of bases in a probe for hybridization is determined under the consideration of the conditions of hybridization, such as the concentration of target mRNA in a live cell to be used and the temperature in hybridization. Generally, the melting point of a hybrid formed with a probe and mRNA is elevated with the increased number of bases in a probe. For example, if the number of bases in a probe is 15 or so, a hybrid is likely to be formed at room temperature with adequately high efficiency, but at 37° C., the hybrid is not to be formed with high efficiency. In order to detect a hybrid at 37° C., it is desirable to use probes with the length of 15 bases or more, preferably 20 bases or more.

On the other hand, the ratio of hybrid formation decreases as the number of bases increases when the number of bases of a probe is in the range of 15–20. For example, at room temperature, the time necessary to complete the hybridization between a probe of 20 bases and mRNA is several times longer than the time required for a probe of 15 bases.

Taken these requirements together, it is further preferable that the number of bases in a probe is 10–50, more preferably 15–20.

When the probes are designed, it is also important what site in the mRNA probes hybridize to, as well as the number of bases in a as described above. That is, mRNA itself is a molecule with complicated secondary and tertiary structure. Thus, even if the probe to be used has a base sequence complementary to a particular site of the mRNA, an obstruction for the probe to hybridize to the site often occurs in the secondary and tertiary structure when the site interacts with other sites of the mRNA. In the present invention, therefore, the sites where the probes hybridize to have to be selected.

The sites for hybridization are determined, for example, by approaches described below. First, base sequences of the objective mRNA are obtained from a database. If databases are not available, the base sequences of the mRNA may be determined by well-known methods. According to the information, a secondary structure of the mRNA is simulated. For this simulation, it is possible to use commercially available computer programs for predicting the secondary structure of RNA, such as DNAs is (Hitachi Software Engineering Inc.). Using the obtained secondary structure, a site with appropriate number of bases, which include the base sequences in the site free from obstruction for hybridization, is selected; an oligonucleotide having a base sequence complementary to the selected base sequence is synthesized; the synthesized oligonucleotide is fluorescently labeled; and the oligonucleotide is used as a probe.

After several objective sites having 30–40 bases for hybridization are selected, it is preferable that each site is subdivided into two parts (each 15–20 bases). Oligonucleotides having base sequences respectively complementary to the subdivided parts are synthesized, and then fluorescently labeled to prepare the first probe and the second probe for use.

In order to select a desirable set of probes from several sets of probes selected and synthesized as above, the following method can be used: the first probe and the second probe are mixed and the fluorescence spectra is measured; then, the objective mRNA is added to the mixed solution to observe any changes in the fluorescence spectra. When the first probe, the second probe and mRNA is formed into a hybrid, FRET occurs between two types of fluorescent dyes; as a result, the fluorescence intensity of the energy donor dye decreases, while a fluorescence spectrum is obtained where the fluorescence intensity of the energy acceptor dye is increased. The aforementioned operation is carried out on several sets of first and second probes; the changes in fluorescence spectra are compared; and a set of probes with a greater change is selected. The objective mRNA used for these methods can be synthesized by in vitro transcription reaction using a recombinant plasmid DNA which includes cDNA corresponding to the mRNA.

Then, hybrids and free probes are separated from each other using high performance liquid chromatography (HPLC) or the like to correctly evaluate the efficiency of each probe to hybridize to the objective mRNA, each probe and each objective RNA are mixed and reacted in an aqueous solution.

The method to design the desirable fluorescence-labeled probes adopted in the present invention is described above in detail. Such fluorescence-labeled probe is one of the preferable forms of markers to be used in the present invention. In the present invention, after markers have been prepared, they may be introduced into the live cells which have expressed a specific mRNA. As there are no limitations to the methods for introducing markers into the live cells, well-known methods are available, including microinjection, electroporation, and lipofection methods. In the present invention, the electroporation method is preferable, because the method can introduce markers into more than 10,000,000 of live cells in a short time at once.

After the markers have been introduced into the live cells, mRNA is labeled with the markers in the cells. Fluorescence-labeled probes are used as markers, which specifically hybridize to the corresponding mRNA. The conditions for hybridization are not limited specifically, but, for example, live cells which have been introduced fluorescent labeled probes, may be retained at room temperature at least for a few minutes.

After the cellular mRNA is labeled, live cells containing the labeled mRNA are identified by detecting the labeled mRNA, and the identified cells are selectively separated. In the present invention, there are no limitations to the method to detect the labeled mRNA. All of the live cell groups of which markers have been introduced do not always express the objective mRNA. In addition, when the marker has been introduced excessively in amount into the cells expressing the mRNA, the marker which does not bind to the mRNA will remain in the cell. Therefore, it is necessary to detect the labeled mRNA, i.e., markers bound to the mRNA, specifically among the unbound and free markers.

As a method for easily and highly sensitively detecting labeled mRNA in the presence of markers unbound to the mRNA, the first probe labeled with an energy donor dye and the second probe labeled with an energy acceptor dyes are preferably used together. These probes are introduced into the live cells to keep the live cells under the conditions where the probes and the mRNA can hybridize, the excitation light of the energy donor fluorescent dye of the first probe is irradiated to the live cell group, whereby the fluorescence from the energy acceptor fluorescent dye of the second probe is observed based on FRET, and finally the fluorescent labeled mRNA is detected specifically.

Although irradiation of excitation light excites the energy donor dye of the first probe whether the probe hybridizes to the objective mRNA or not, only when the both of the first and second probes hybridize adjacently to the same mRNA, FRET occurs, resulting in emission of fluorescence from the energy acceptor fluorescent dye. That is, the FRET-fluorescence from the acceptor fluorescent dye indicates that the first probe and the second probe are adjacent on the objective mRNA, showing that the objective genes are expressed in the cells.

The live cells which have expressed specific genes detected in this way are selectively separated, but there are no limitations for this separating method. In the present invention, when fluorescence-labeled probes are used, it is preferable to use a cell sorter (Fluorescence Activated Cell Sorter, FACS) to detect live cells, which express specific genes, and then to selectively separate them.

In general, an apparatus consisting of a flow cytometer and a cell dispenser is called a cell sorter. Individual cells, which have been stained with fluorescence-labeled probes, are exposed to laser beam on the way of a flow path, resulting in the light scattering and fluorescence from the cell. The intensity of light scattering (forward scattering light or side scattering light) and fluorescence are measured for each cell and the results for a number of cells are displayed, for example, as a frequency distribution diagram (dot plot). Then, the cells emitting fluorescence with the desired extent are collected by gating. The method as mentioned above is called flow cytometry.

In the present invention, when live cells which have expressed a specific gene are selectively separated with the cell sorter using fluorescent labeled probes which can cause FRET, the following method can be applied. In the cell sorter, laser exciting energy donor is irradiated to each cell, and fluorescence intensities of energy donor fluorescent dyes (for example, Bodipy 493/503) as well as on relative fluorescence intensities of energy acceptor dyes (for example, Cy5) are obtained. Each cell is represented as a dot according to the intensity of the donor and acceptor fluorescence, in a diagram where the horizontal and vertical axis represents intensity of donor and acceptor fluorescence, respectively. Then, in the dot-plotted diagram, the cells emitting relatively high fluorescence intensity on the vertical axis are selected and these cells are designated as a region in the diagram, R2. Next, obtaining the intensity of forward scattering light (FSC), and side scattering light (SSC) representing the size of live cells to be measured, and the complexities of cellular infrastructures, respectively, each cell is represented as a dot in a diagram according to the value of FSC and SSC, on the horizontal and vertical axis, respectively. In the dot-plotted diagram, a region representing the cells emitting FSC as well as SSC with the desirable extent, is selected and designated as R1. After a cell sorter is set so that only live cells suitable for both conditions of R1 and R2 are collected, the cells expressing specific mRNA are selectively separated.

By using the methods as described, various types of live cells as well as various type of mRNA are objectives of selective separation. TH1 and TH2 derived from helper T cells which have been activated by recognizing antigens as foreign do not have any crucial cell surface antigens (markers) to be distinguished from each other. Further, cytokines produced by TH1 and TH2, IL-2 and IL-4, respectively, do not remain in the cell or near the cell membrane and are liberated to the extracellular fluid. Thus, TH1 or TH2 is an ideal objective to which the selective separation of the present invention is applied. That is, the selective separation method according to the present invention is preferably used for live cell groups containing live cells having mRNA encoding cytokines.

Especially, it is preferable that live cell groups containing live cells having mRNA encoding interleukin-2 (IL-2) are applied to this method of the present invention. To separate live cells expressing IL-2 mRNA, the first probe labeled with the energy donor fluorescent dye having a base sequence set forth in SEQ ID NO: 9 in the Sequence Listing and the second probe labeled with the energy acceptor fluorescent dye having a base sequence set forth in SEQ ID NO: 10 in the Sequence Listing are used, and FRET generated by these probes is utilized as an index for selective separation.

The base sequence set forth in SEQ ID NO: 9 in the Sequence Listing is complementary to the base sequence, 342–356 in the base sequence of mRNA encoding IL-2, while the base sequences set forth in SEQ ID NO: 10 in the Sequence Listing is complementary to the base sequence, 357–371 in the base sequence of mRNA encoding IL-2. When the first probe labeled with the energy donor fluorescent dye are made adjacent to the second probe labeled with the energy acceptor fluorescent dye at the positions indicated above of the same mRNA molecule, the detection of the FRET-fluorescence can be carried out with high sensitivity.

Furthermore, it is preferable that live cell groups containing live cells having mRNA encoding interleukin-4 (IL-4) are are applied to this method of the present invention. To separate live cells expressing IL-4 mRNA, the first probe labeled with the energy donor fluorescent dye having a base sequence set forth in SEQ ID NO: 17 in the Sequence Listing and the second probe labeled with the energy acceptor fluorescent dye having a base sequence set forth in SEQ ID NO: 18 in the Sequence Listing are used, and FRET generated by these probes is utilized as an index for separation.

The base sequence set forth in SEQ ID NO: 17 in the Sequence Listing is complementary to the base sequence, 265–279 in the base sequence of mRNA encoding IL-4, while the base sequences set forth in SEQ ID NO: 18 in the Sequence Listing is complementary to the base sequence, 280–294 in the base sequence of mRNA encoding IL-4. When the first probe labeled with the energy donor fluorescent dye are made adjacent to the second probe labeled with the energy acceptor fluorescent dye at the positions indicated above of the same mRNA molecule, the detection of the FRET-fluorescence can be carried out with high sensitivity.

EXAMPLES

The present invention will be explained in greater detail by way of preferred examples hereinbelow. However, the present invention should not be limited to these examples.
(1) Preparation of Fluorescent Labeled Markers of Oligonucleotides Complementary to IL-2 mRNA and IL-4 mRNAP Five sites, 30 bases each, were selected on the base sequences of IL-2 or IL-4 mRNA. Each 30 bases-site was divided into two halves (15 bases-site). An oligonucleotide complementary to each 15 bases-site was designed as a DNA probe for each site and labeled with a fluorescent dye, Bodipy493/503, Cy5, or XRITC.

The DNA probe was synthesized using a DNA/RNA synthesizer (Perkin Elmer: Model 394 or Perceptive: Model 18909), by β-cyanoethylamidethod. The entire base sequence of IL-2 mRNA and base sequences of the oligo DNA probes are shown in FIG. 1, and the entire base sequence of IL-4 mRNA and base sequences of the oligo DNA probes are shown in FIG. 2. The base sequences of the designed 10 types of oligo DNA probes for IL-2 mRNA (SEQ ID NOs: 1–10) and the base numbers (hybridized positions) on IL-2 mRNA to which the oligo DNA probes hybridize are shown in Table 1. The base sequences of 10 types of oligo DNA probes for IL-4 mRNA (SEQ ID NOs: 11–20) and the base numbers (hybridized positions) on IL-4 mRNA to which the oligo DNA probes hybridize are shown in Table 2.

TABLE 1

| SEQ ID NO: | Base Sequence | Hybridized Position* |
| --- | --- | --- |
| SEQ ID NO: 1 | 5'-GTAAAACTTAAATGT-3' | 228–242 |
| SEQ ID NO: 2 | 5'-GGCCTTCTTGGGCAT-3' | 243–257 |
| SEQ ID NO: 3 | 5'-TTTGGGATTCTTGTA-3' | 198–212 |
| SEQ ID NO: 4 | 5'-GAGCATCCTGGTGAG-3' | 213–227 |
| SEQ ID NO: 5 | 5'-GCAAGACTTAGTGCA-3' | 77–91 |
| SEQ ID NO: 6 | 5'-CTGTTTGTGACAAGT-3' | 92–106 |
| SEQ ID NO: 7 | 5'-GGTTTGAGTTCTTCT-3' | 287–301 |
| SEQ ID NO: 8 | 5'-AGCACTTCCTCCAGA-3' | 302–316 |
| SEQ ID NO: 9 | 5'-CCTGGGTCTTAAGTG-3' | 342–356 |
| SEQ ID NO: 10 | 5'-ATTGCTGATTAAGTC-3' | 357–371 |

*Base number of IL-2 mRNA to which each probe hybridizes.

TABLE 2

| SEQ ID NO: | Base Sequence | Hybridized Position* |
| --- | --- | --- |
| SEQ ID NO: 11 | 5'-CAGTTGGGAGGTGAG-3' | 70–84 |
| SEQ ID NO: 12 | 5'-GAACAGAGGGGGAAG-3' | 85–99 |
| SEQ ID NO: 13 | 5'-CGTGGACAAAGTTGC-3' | 119–133 |
| SEQ ID NO: 14 | 5'-TATCGCACTTGTGTC-3' | 134–148 |
| SEQ ID NO: 15 | 5'-CTGTGAGGCTGTTCA-3' | 176–190 |
| SEQ ID NO: 16 | 5'-ACAGAGTCTTCTGCT-3' | 191–205 |
| SEQ ID NO: 17 | 5'-AGCCCTGCAGAAGGT-3' | 265–279 |
| SEQ ID NO: 18 | 5'-CCGGAGCACAGTCGC-3' | 280–294 |
| SEQ ID NO: 19 | 5'-CCGTTTCAGGAATCG-3' | 376–390 |
| SEQ ID NO: 20 | 5'-GAGGTTCCTGTCGAG-3' | 391–405 |

*Base number of IL-4 mRNA to which each probe hybridizes.

In (4A) described below, oligo DNAs corresponding SEQ ID NOs: 1–10 were labeled with Bodipy493/503 at the 5' end, and were used as probes. In (8), unlabeled oligo DNAs corresponding SEQ ID NOs: 1–10 were used as probes. In (9), oligo DNAs corresponding SEQ ID NOs: 1, 3, 6, 7, or 9 were labeled with Bodipy493/503 at the 5' end, and oligo DNAs corresponding SEQ ID NOs: 2, 4, 6, 8, or 10 were labeled with XRITC at the linkage between the 4th nucleotide and the 5th from the 3' end and were used as probes. In (11), oligo DNAs corresponding SEQ ID NOs: 1, 3, 5, 7, or 9 were labeled with Bodipy493/503 at the 5' end, and oligo DNAs corresponding SEQ ID NOs: 2, 4, 6, 8, or 10 were labeled with Cy5 at the linkage between the 4th nucleotide and the 5th from the 3' end and were used as probes. The labeling of oligo DNAs with Bodipy493/503, XRITC, or Cy5 were performed as described in (a)–(c).

In the present invention, the oligo DNA probes, which are labeled with energy donor fluorescent dyes, are sometimes abbreviated as donor probes, while oligo DNA probes, which are labeled with energy acceptor fluorescent dyes are sometimes abbreviated as acceptor probes. The probe, corresponding SEQ ID NO: 1 was labeled with an energy donor fluorescent dye, is complementary to the sequence, 228–242 of IL-2 mRNA. Thus, the probe may sometimes be referred to as IL-2 228–242(D) (D means a donor). The probe, corresponding SEQ ID NO: 2 was labeled with an energy acceptor fluorescent dye, is complementary to the sequence, 243–257 of IL-2 mRNA. Thus, the probe may be sometimes referred to as IL-2 243–257(A) (A means an acceptor). In addition, when the probe is not labeled with a fluorescent dye, it is simply referred to as IL-2 228–242. Thus, the probes used in (9) and (11) may be represented by the names of probes shown in Table 2 hereunder.

TABLE 3

| SEQ ID NO: | Base Sequence | Name of Probes |
| --- | --- | --- |
| SEQ ID NO: 1 | 5'-GTAAAACTTAAATGT-3' | IL-2 228–242(D) |
| SEQ ID NO: 2 | 5'-GGCCTTCTTGGGCAT-3' | IL-2 248–257(A) |
| SEQ ID NO: 3 | 5'-TTTGGGATTCTTGTA-3' | IL-2 198–212(D) |
| SEQ ID NO: 4 | 5'-GAGCATCCTGGTGAG-3' | IL-2 213–227(A) |
| SEQ ID NO: 5 | 5'-GCAAGACTTAGTGCA-3' | IL-2 77–91(D) |
| SEQ ID NO: 6 | 5'-CTGTTTGTGACAAGT-3' | IL-2 92–106(A) |
| SEQ ID NO: 7 | 5'-GGTTTGAGTTCTTCT-3' | IL-2 287–301(D) |
| SEQ ID NO: 8 | 5'-AGCACTTCCTCCAGA-3' | IL-2 302–316(A) |
| SEQ ID NO: 9 | 5'-CCTGGGTCTTAAGTG-3' | IL-2 342–356(D) |
| SEQ ID NO: 10 | 5'-ATTGCTGATTAAGTC-3' | IL-2 367–371(A) |

IL-4 probes are sometimes represented in the same manner as above. For example, the probes used in (3B) as described below may be represented by the names of probes shown in Table 4 hereunder.

TABLE 4

| SEQ ID NO: | Base Sequence | Name of Probes |
| --- | --- | --- |
| SEQ ID NO: 11 | 5'-CAGTTGGGAGGTGAG-3' | IL-4 70–84(D) |
| SEQ ID NO: 12 | 5'-GAACAGAGGGGGAAG-3' | IL-4 85–99(A) |
| SEQ ID NO: 13 | 5'-CGTGGACAAAGTTGC-3' | IL-4 119–133(D) |
| SEQ ID NO: 14 | 5'-TATCGCACTTGTGTC-3' | IL-4 134–148(A) |
| SEQ ID NO: 15 | 5'-CTGTGAGGCTGTTCA-3' | IL-4 176–190(D) |
| SEQ ID NO: 16 | 5'-ACAGAGTCTTCTGCT-3' | IL-4 191–205(A) |
| SEQ ID NO: 17 | 5'-AGCCCTGCAGAAGGT-3' | IL-4 265–279(D) |
| SEQ ID NO: 18 | 5'-CCGGAGCACAGTCGC-3' | IL-4 280–294(A) |
| SEQ ID NO: 19 | 5'-CCGTTTCAGGAATCG-3' | IL-4 376–390(D) |
| SEQ ID NO: 20 | 5'-GAGGTTCCTGTCGAG-3' | IL-4 391–405(A) |

(a) Preparation of Donor Probes (Bodipy 493/503-Labled)

2.5 mg of NHSS (N-Hydroxysulfosuccinimide sodium salt) in 30 µl of sterilized water, 5 mg of EDAC [1-ethyl-3-(3-dimethylaminopropyl)carbodiimide] in 50 µl of sterilized water, and 1 mg of Bodipy493/503 propionic acid dissolved in 50 µl of DMF were mixed and reacted with at room temperature for 30 minutes.

An oligo DNA with the base sequence described above (lyophilized product), which a hexylamino group was introduced to the 5' end using 6-(trifluoroacetylamino)hexyl-(2-cyanoethyl)-(N,N-di-isopropyl)-phosphoroamidite, a 5' end aminating agent, was dissolved in 200 µl of 0.5M of $Na_2HCO_3/NaH_2CO_3$ buffer solution (pH 9.3). These were mixed and reacted overnight in the dark.

After the reacted solution was gel filtrated to remove unreacted dyes, the reaction solution was subjected to reversed phase high performance liquid chromatography (HPLC) with CAPCELL PACK18 (Shiseido Inc., Column size: 6 mm in inner diameter×250 mm in length), and the fractions with absorption at 260 nm and 493 nm were recovered and lyophilized. HPLC was performed under the following condition, flow rate; 1 ml/minute, temperature; 40° C., the mobile phase was the mixture of solution A (5% $CH_3CN$ containing 5 mM of TEAA) and solution B (40% $CH_3CN$) and the concentration gradient of $CH_3CN$ was generated by increasing the concentration of solution B from 30% to 80 in 20 minutes.

(b) Preparation of Acceptor Probes (Cy5-Labeled)

Cy5 dye in one tube (Amersham, Fluorolink Cat.No.PA25001) was dissolved in 100 µl of sterilized water. An oligo DNA with the base sequence described above (lyophilized product) which a hexylamino group was introduced into the linkage between the 4th nucleotide and the 5th from the 3' end using a Uni-Link AminoModifier (Clontech Inc.), was dissolved in 200 µl of $Na_2HCO_3/NaH_2CO_3$ buffer solution (0.5M, pH 9.3). These were mixed in the dark, and reacted overnight.

After the reacted solution was gel filtrated to remove unreacted dyes, the reaction solution was subjected to reversed phase high performance liquid chromatography (HPLC) with CAPCELL PACK18 (Shiseido Inc., Column size: 6 mm in inner diameter×250 mm in length), and the fractions with absorption at 260 nm were recovered. HPLC was performed under the following condition, flow rate; 1 ml/minute, temperature; 40° C., the mobile phase was the mixture of solution A (5% $CH_3CN$ containing 5 mM of TEAA) and solution B (40% $CH_3CN$) and the concentration gradient of $CH_3CN$ was generated by increasing the concentration of solution B from 15% to 60 in 20 minutes. When the absorption spectra of the recovered fractions was measured in the range of 220–700 nm, the maximum absorption was observed between 650–700 nm, indicating a typical property of Cy5. And then the fractions were lyophilized.

(c) Preparation of Acceptor Probes (XRITC-Labeld)

One hundred microliters of XRITC dye solution (Solvent: 100% DMSO, Perkin Elmer, ROX-NHS) was reacted with an oligo DNA having the base sequence described above where a hexylamino group was introduced as described in (B). The reaction product was applied to reversed phase high performance liquid chromatography; a fraction with an absorption band at 260 nm was recovered; the absorption spectrum was measured in the range between 220–650 nm; after the maximum absorption of XRITC was observed in the range between 550–600 nm, the recovered fraction was lyophilized.

(2A) In Vitro Synthesis of Human IL-2 RNA

In order to obtain human IL-2 RNA having a base sequence equivalent to human IL-2 mRNA, an IL-2 cDNA fragment was cleaved out with restriction enzyme pst I from pTCGF-II (ATCC#39673), a plasmid containing a human IL-2 cDNA and was linked to the pst I site of pBluescript KS(+) a plasmid vector for RNA synthesis using Ligation kit version 2 (Takara) so that the cDNA would be located in the downstream of T3 promoter. The obtained recombinant plasmid was introduced into competent cells of E. coli JM109 strain (Takara Co.), and the transformants of the E. coli obtained were cultured, 46.2 µg of the plasmid DNA was extracted and purified from 100 ml of the bacterial culture using a Plasmid Midi Kit (QIAGEN).

The recombinant plasmid was linearized by restriction enzyme Sma I digestion to prepare the template for the synthesis of human IL-2 RNA. The enzyme proteins in the plasmid solution was degraded with proteinase K and denatured/removed with phenol/chloroform. The RNA synthesis was performed using 0.66 µg of the purified template with the base composition, A (adenine):C (cytosine):G (guanine):U (uracil), 35:18:14:32%. A, C, G and U were added to the template at the final concentrations of 105, 54, 42 and 96 mM, respectively together with T3 RNA polymerase according to the aid of an in vitro transcription kit (Megascript T3 Kits, Ambion). Polymerase reaction was carried out at 37° C. for 6 hours to synthesize human IL-2 RNA. After the reaction was over, the RNA was purified as follows. The template DNA was decomposed with DNase I (Megascript T3 Kits, Ambion Inc.), the enzyme proteins in the transcription reaction solution was denatured/removed with phenol/chloroform. To the obtained RNA solution was added an equal volume of isopropanol, and human IL-2 RNA was recovered as a precipitate by centrifugation (14 krpm, for 7 minutes), while the respective nucleotides which were unreacted enzyme substrates were removed. The human IL-2 RNA precipitate (139 µg) rinsed once with 70% ethanol was dissolved in RNase-free water (Megascript T3 Kits, Ambion) so that 5 µg/µl of human IL-2 RNA solution was prepared to use for the subsequent hybridization experiments.

(2B) In Vitro Synthesis of Human IL-4 RNA

Next, in order to obtain human IL-4 RNA a having base sequence equivalent to human IL-4 mRNA, human IL-4 cDNA fragment was cleaved out with restriction enzymes BamHI and Xho I from pcD-hIL-4 (ATCC#57593), a plasmid DNA containing human IL-4 cDNA. The cDNA fragment was linked to the BamHI and Xho I sites of a pBluescript KS(+), a plasmid vector for RNA synthesis using Ligation kit version 2 (Takara) so that the cDNA would be located in the downstream of T3 promoter. The obtained recombinant plasmid was introduced into competent cells of E. coli JM109 strain (Takara Co.); the transformants of the E. coli obtained were cultured; and 152 µg of plasmid DNA was extracted and purified from 100 ml of the bacterial culture using a Plasmid Midi Kit (QIAGEN).

The recombinant plasmid was linearized by digestion with restriction enzyme Sma I to prepare the template for the synthesis of human IL-4 RNA. The enzyme proteins in the plasmid solution was degraded with proteinase K and denatured/removed with phenol/chloroform. The RNA synthesis was performed using 0.46 μg of the purified template with the base composition, A: C: G: U, 29:24:21:26%. A, C, G and U were added to the template at the final concentrations of 87, 72, 63 and 78 mM, respectively together with T7 RNA polymerase according to the aid of an in vitro transcription kit (Megascript T7 Kits, Ambion). Polymerase reaction was carried out at 37° C. for 6 hours to synthesize human IL-4 RNA. After the reaction was over, the RNA was purified as follows. The template DNA was decomposed with DNase I (Megascript T7 Kits, Ambion Inc.), the enzyme proteins in the transcription reaction solution was denatured/removed with phenol/chloroform. To the obtained RNA solution was added an equal volume of isopropanol, and human IL-4 RNA was recovered as a precipitate by centrifugation (14 krpm, for 7 minutes), while the free nucleotides, unreacted enzyme substrates, were removed. The human IL-4 RNA precipitate (139 μg) rinsed once with 70% ethanol was dissolved in RNase-free water (Megascript T7 Kits, Ambion) so that 5 μg/μl of human IL-4 RNA solution was prepared to use for the subsequent hybridization experiments.

(3A) Changes in Fluorescence Spectra by Hybridization of Fluorescent Labeled Probes to Human IL-2 RNA In order to measure changes in fluorescence spectra due to fluorescence resonance energy transfer (FRET) caused by hybridization of donor probes and acceptor probes to adjacent sites on IL-2 RNA, a pair of 300 nM (final concentration) of Bodipy 493/503-labeled donor probes and XRITC-labeled acceptor probes, and human IL-2 RNA were mixed in 100 μl of 1×SSC solution (150 mM sodium chloride, 17 mM citric acid, pH 7.0), and allowed to stand at room temperature for 15 minutes, and then fluorescence spectra were measured. As combinations of donor probes and acceptor probes, IL-2 228–242(D) and IL-2 243–257(A), IL-2 198–212(D) and IL-2 213–227(A), IL-2 77–91(D) and IL-2 92–106(A), IL-2 287–301(D) and IL-2 302–316(A), and IL-2 342–356(D) and IL-2 357–371(A), were used. As a control, the fluorescence spectrum of 300 nM of the probe alone was also measured. The conditions for fluorescence spectrum measurement were as follows:

Fluorospectrophotometer: F4500 (Hitachi) 108 Excitation wavelength: 480 nm
Fluorescence-measurement Wavelength: 500–750 nm
Temperature: room temperature.

For all the combinations examined, changes in fluorescence spectra were observed, i.e., the intensity of donor fluorescence decreased while acceptor fluorescence (580–650 nm) increased with donor excitation due to the addition of human IL-2 RNA to the probe solution. See FIGS. 3–7. FIGS. 3, 4, 5, and 6 show fluorescence spectra when the combinations of IL-2 228–242 (D) and IL-2 243–257(A), IL-2 198–212(D) and IL-2 213–227(A), IL-2 77–91(D) and IL-2 92–106(A), IL-2 287–301(D) and IL-2 302–316(A), and IL-2 342–356(D) and IL-2 357–371(A) were used. As seen from the comparison among FIGS. 2–6, the extent of changes in fluorescence spectra was different from each other among the combinations of probes, the most remarkable change occurred when the combination of IL-2 342–356(D) and IL-2 357–371(A) was used.

(3B) Changes in Fluorescence Spectra by Hybridization of Fluorescent Labeled Probes to Human IL-4 RNA In order to measure changes in fluorescence spectra due to fluorescence resonance energy transfer (FRET) caused by hybridization of donor probes and acceptor probes to adjacent sites on IL-4 RNA, a pair of 300 nM (final concentration) of Bodipy 493/503-labed donor probes and Cy5-labeled acceptor probe, and human IL-4 RNA were mixed in 100 μl of 1×SSC solution (150 mM sodium chloride, 17 mM citric acid, pH 7.0), and allowed to stand at room temperature for 15 minutes, and then fluorescence spectra were measured. As combinations of donor probes and acceptor probes, IL-4 70–84(D) and IL-4 85–99(A), IL-4 119–133(D) and IL-4 134–148(A), IL-4 176–190(D) and IL-4 191–205(A), IL-4 265–279(D) and IL-4 280–294 (A), and IL-4 376–390(D) and IL-4 391–405(A), were used. As a control, the fluorescence spectrum of 300 nM of the probe described above alone was also measured. The conditions for measurement were as follows:

Fluorospectrophotometer: F4500 (Hitachi)
Excitation wavelength: 480 nm
Fluorescence-measurement Wavelength: 500–750 nm
Temperature: room temperature.

For all the combinations examined, changes in fluorescence spectra were observed, i.e., the intensity of donor fluorescence decreased while acceptor fluorescence (650–700 nm) increased with donor excitation due to the addition of human IL-4 RNA to the probe solution. See FIGS. 8–12. FIGS. 8, 9, 10, 11 and 12 show fluorescence spectra when the combinations of IL-4 70–84 (D) and IL-4 85–99(A), IL-4 119–133(D) and IL-4 134–148(A), IL-4 176–190(D) and IL-4 191–205(A), IL-4 265–279(D) and IL-4 280–294(A), and IL-4 376–390(D) and IL-4 391–405 (A) were used. As seen from the comparison among FIGS. 8–12, the extent of changes in fluorescence spectra was different from each other among the combinations of probes, the most remarkable change occurred when the combination of IL-4 265–279(D) and IL-4 280–294(A) was used. The results of the measurements are shown as the relative fluorescence intensity of Cy5 to Bodipy493-503 by excitation of Bodipy493-503 (Cy5 fluorescence intensity/Bodipy493-503 fluorescence intensity) in Table 5.

TABLE 5

| Probe Combination | Ratio of Fluorescence Intensities |
|---|---|
| IL-4 70–84 (D) and IL-4 85–99 (A) | 1.3% |
| IL-4 119–133 (D) and IL-4 134–148 (A) | 2.5% |
| IL-4 176–190 (D) and IL-4 191–205 (A) | 22.4% |
| IL-4 265–279 (D) and IL-4 280–294 (A) | 14.5% |
| IL-4 376–390 (D) and IL-4 391–405 (A) | 1.5% |

(4A) Measurement of Hybridization Efficiency of Probes to Human IL-2 RNA by HPLC Each donor probe (3 pmol) wherein an oligo DNA corresponding SEQ ID NO: 1–10 was labeled with Bodipy493/503 was mixed with an equimolar amount of human IL-2 RNA synthesized in (2A) in 10 μl of 1×SSC solution (150 mM sodium chloride, 17 mM sodium citrate, pH 7.0), and the mixture was allowed to stand at room temperature for 15 minutes. Subsequently, hybrids consisting of human IL-2 RNA and probes were separated from free probes by high performance liquid chromatography (HPLC) using differences in retention time under the following conditions, i.e., retention time is about 4–5 minutes and 7.5 minutes for free probes and hybrids, respectively.

Column: TSKgel DRAE-NPR (Toso Inc., 4.6 mm in inner Diameter×35 mm in total length)
Flow Rate: 1 ml/minute
Temperature: 25° C.
Mobile phase: Solution A: 20 mM Tris-HCl (pH 9.0),
Solution B: 0.5 mM NaCl, 20 mM Tris-HCl (pH 9.0)

HPLC was performed in the concentration gradient manner. The mobile phase was the mixture of solution A and solution B and the concentration gradient of NaCl was generated by increasing the concentration of solution B from 25% to 100% so that the concentration of NaCl changed from 0.125M to 0.5M in 10 minutes. Absorbance at 260 nm for nucleic acids and fluorescence intensity at 515 nm with the excitation at 475 nm for Bodipy493/503 were monitored simultaneously on eluted fractions. The fractions with the absorbance at 260 nm as well as the fluorescence at 515 nm were regarded as the ones of hybrids. The relative fluorescence intensity of the hybrid fractions to all the fractions in the fluorescence chromatogram was estimated and used as an index for the efficiency of hybridization.

Figure 13:
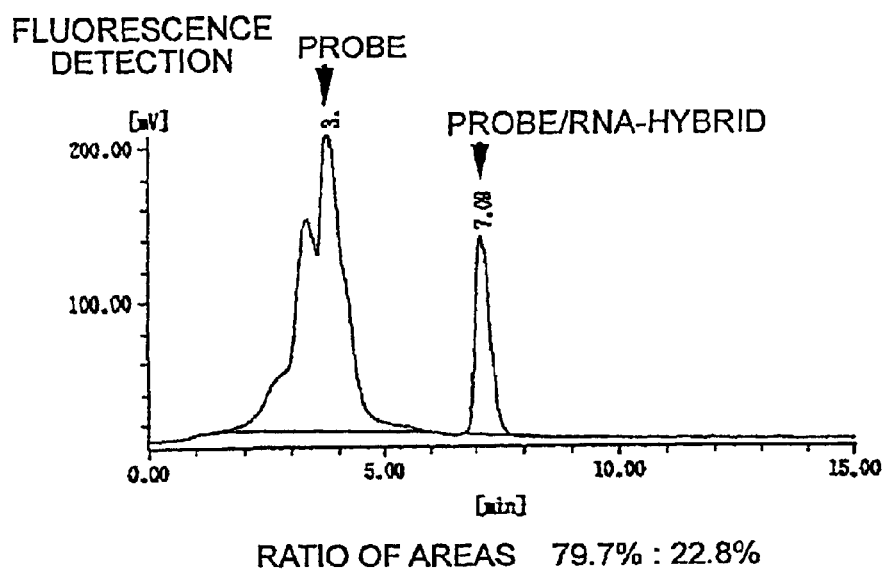
FIG. 13 is a chromatogram of HPLC obtained when a mixture solution of the donor probe IL-2 342–356(D) and IL-2 RNA was separated by HPLC.
Figure 14:
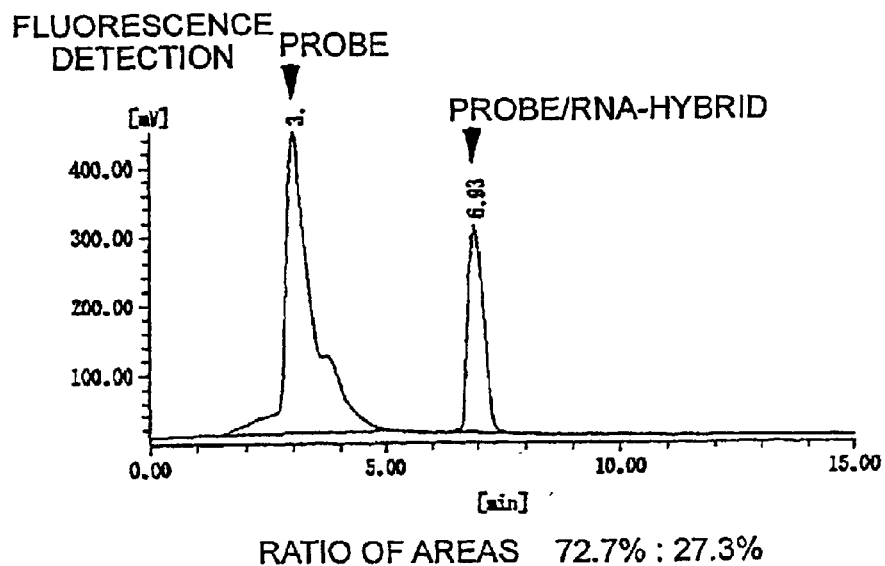
FIG. 14 is a chromatogram of HPLC obtained when a mixture solution of the acceptor probe IL-2 357–371(A) and IL-2 RNA was separated by HPLC.
Figure 15:
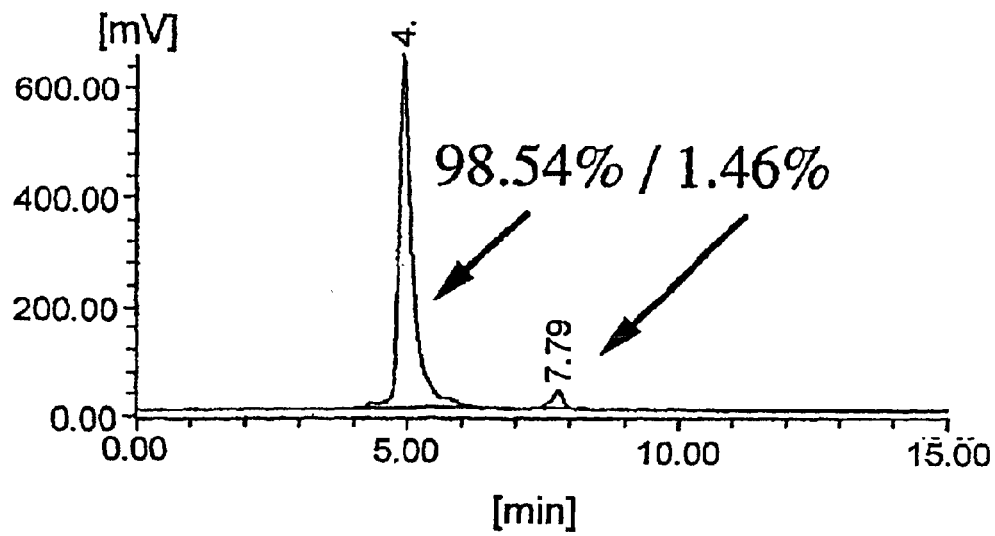
FIG. 15 is a chromatogram of HPLC obtained when a mixture of the donor probe IL-4 119–133(D) and IL-4 RNA was separated by HPLC.
Figure 16:
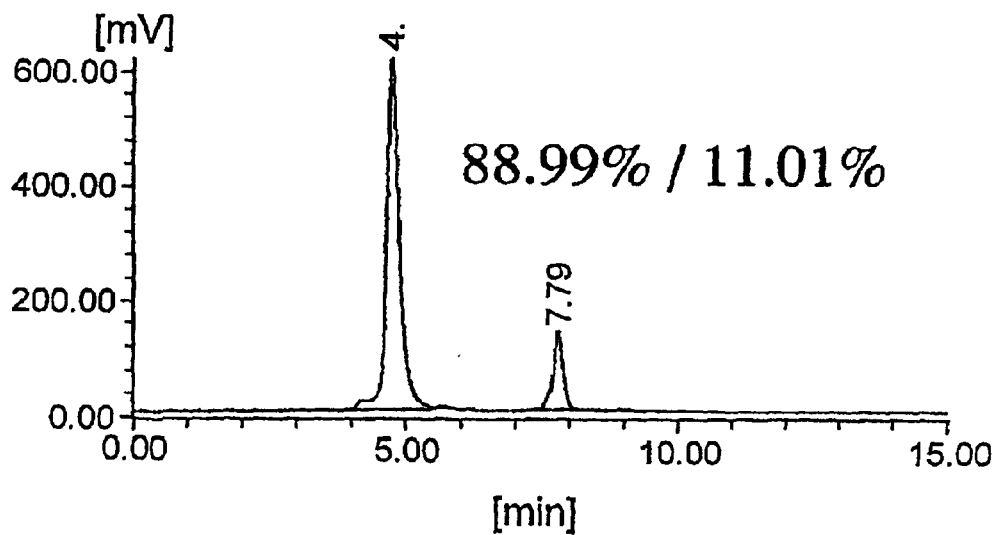
FIG. 16 is a chromatogram of HPLC obtained when a mixture of the acceptor probe IL-4 134–148(A) and IL-4 RNA was separated by HPLC.
Figure 17:
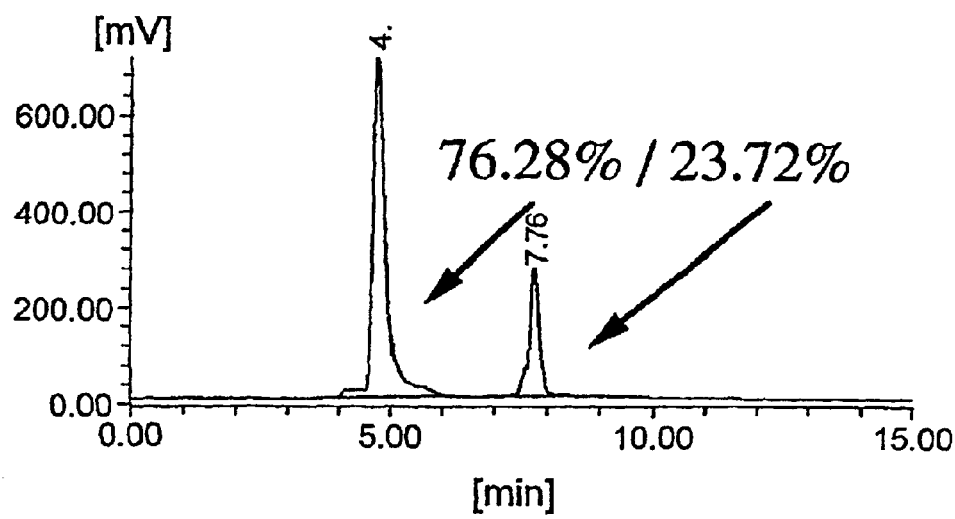
FIG. 17 is a chromatogram of HPLC obtained when a mixture of the donor probe IL-4 265–279(D) and IL-4 RNA was separated by HPLC.
Figure 18:
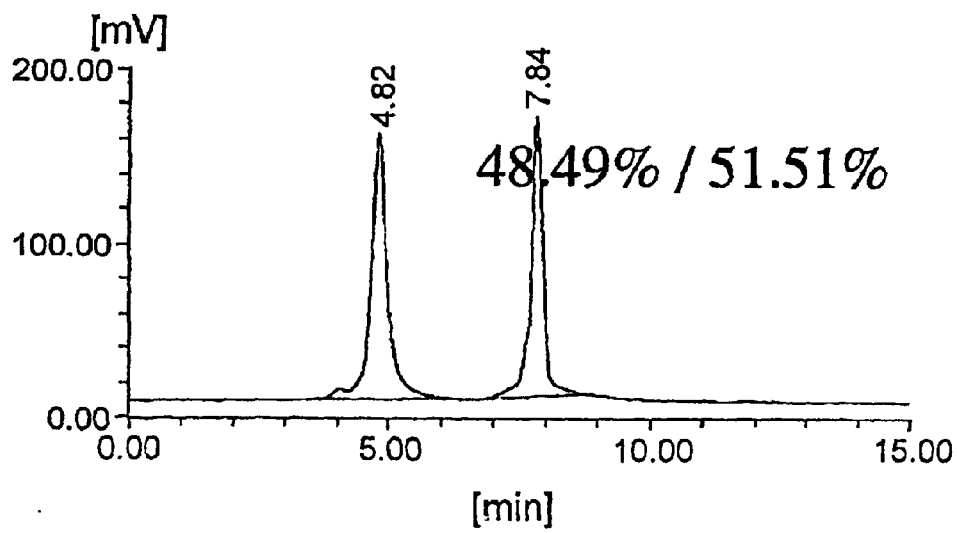
FIG. 18 is a chromatogram of HPLC obtained when a mixture of the acceptor probe IL-4 280–294(A) and IL-4 RNA was separated by HPLC.

FIG. 13 shows a HPLC chromatogram when IL-2 342–356 (D) was mixed with IL-2 RNA. FIG. 14 shows a HPLC chromatogram when IL-2 357–371(D) was mixed with IL-2 RNA. Ratios of the peak areas of hybrids to all the peak areas in the fluorescence chromatogram, estimated for each probe, were summarized and shown in Table 6.

TABLE 6

| Name of Probe | Base Sequence | Ratio of Hybrid (%) |
|---|---|---|
| IL-2 228–242 (D) | 5'-GTAAAACTTAAATGT-3' | 0.1 |
| IL-2 243–257 (D) | 5'-GGCCTTCTTGGGCAT-3' | 17.5 |
| IL-2 198–212 (D) | 5'-TTTGGGATTCTTGTA-3' | 15.7 |
| IL-2 213–227 (D) | 5'-GAGCATCCTGGTGAG-3' | 25.2 |
| IL-2 77–91 (D) | 5'-GCAAGACTTAGTGCA-3' | 0.5 |
| IL-2 92–106 (D) | 5'-CTGTTTGTGACAAGT-3' | 18.3 |
| IL-2 287–301 (D) | 5'-GGTTTGAGTTCTTCT-3' | 13.3 |
| IL-2 302–316 (D) | 5'-AGCACTTCCTCCAGA-3' | 6.2 |
| IL-2 342–356 (D) | 5'-CCTGGGTCTTAAGTG-3' | 22.8 |
| IL-2 357–371 (D) | 5'-ATTGCTGATTAAGTC-3' | 27.3 |

From the results shown in Table 6, it was found that IL-2 213–227(D), IL-2 342–356(D), and IL-2 357–371(D) were hybridized to the target RNA with relatively high efficiency. In the results of (3A), the combination of IL-2 342–356(D) and IL-2 357–371(A) caused the largest changes in fluorescence spectra as a pair of a donor probe and an acceptor probe when the probes were mixed with IL-2 RNA. Therefore, the results of (4A) are well consistent with those of (3A).

(4B) Measurement of Hybridization Efficiency of Probes to Human IL-4 RNA by HPLC Each donor probe (3 pmol) wherein an oligo DNA corresponding SEQ ID NO: 11–20 was labeled with Bodipy493/503 was mixed with an equimolar amount of human IL-4 RNA, synthesized in (2B) in 10 μl of 1×SSC solution (150 mM sodium chloride, 17 mM sodium citrate, pH 7.0) and the mixture was allowed to stand at room temperature for 15 minutes. Then, hybrids consisting of human IL-4 RNA and probes were separated from free probes by high performance liquid chromatography (HPLC) using differences in retention time under the following conditions: retention time is about 4–5 minutes for free probe and about 7.5 minutes for hybrid in the HPLC condition below. The conditions for separation and the method for determining hybridization efficiency are the same as those described in (4A).

FIGS. 15, 16, 17 and 18 show HPLC chromatograms when IL-4 119–133 (D), IL-4 134–148(D), IL-4 134–148 (D), IL-4 265–279(D), and IL-4 280–294(D) were mixed with IL-4 RNA, respectively. Ratios based on the peak areas of hybrids to all the peak areas in the fluorescence chromatogram, estimated for each probe, were summarized and shown in Table 7.

TABLE 7

| Hybridized Probe | Base Sequence | Ratio of Hybrid (%) |
|---|---|---|
| IL-4 70–84 (D) | 5'-CAGTTGGGAGGTGAG-3' | 68.6 |
| IL-4 85–99 (D) | 5'-GAACAGAGGGGGAAG-3' | 53.5 |
| IL-4 119–133 (D) | 5'-CGTGGACAAAGTTGC-3' | 4.2 |
| IL-4 134–148 (D) | 5'-TATCGCACTTGTGTC-3' | 22.6 |
| IL-4 176–190 (D) | 5'-CTGTGAGGCTGTTCA-3' | 23.7 |
| IL-4 191–205 (D) | 5'-ACAGAGTCTTCTGCT-3' | 1.5 |
| IL-4 265–279 (D) | 5'-AGCCCTGCAGAAGGT-3' | 15.6 |
| IL-4 280–294 (D) | 5'-CCGGAGCACAGTCGC-3' | 46.6 |
| IL-4 376–390 (D) | 5'-CCGTTTCAGGAATCG-3' | 23.1 |
| IL-4 391–405 (D) | 5'-GAGGTTCCTGTCGAG-3' | 4.0 |

From the results shown in Table 7, it was found that IL-4 265–279(D) and IL-4 280–294(D) were hybridized to the target RNA with relatively high efficiency. In the results of (3B), the combination of IL-4 265–279(D) and IL-4 280–294(A) caused the largest changes in fluorescence spectra as a pair of a donor probe and an acceptor probe when the probes were mixed with IL-4 RNA. Therefore, the results of (4B) are well consistent with those of (3B).

(5) Induction of IL-2 Gene Expression in Human T-Cell Leukemia Strain Cells Jurkat E6-1

To Jurkat E6-1 cells with a cell density of $1 \times 10^6$/ml was added 0.5 mg/ml (final concentration) of anti-CD3 antibody (Immunotech Inc.), 0.5 mg/ml anti-CD28 antibody (Immunotech Inc.), and 10 nM PMA (Sigma Inc.), and they were cultured for 3 days (24 hours) at 37° C. in the presence of 5% $CO_2$.

(6) Measurement of the Production Amount of IL-2 Protein Molecules

If a large amount of IL-2 molecules is produced and liberated into culture supernatant in response to the induction of IL-2 gene expression in (5), it is plausible that IL-2 mRNA is actively synthesized in the cells. Thus, in order to confirm IL-2 gene expression, culture supernatant of Jurkat E6-1 cells treated with IL-2 expression-inducing agents (in some cases, hereinafter called IL-2 expression-induced cells) which had been treated as described in (5) was collected; the amount of IL-2 (pg/ml/$10^7$ cells) in the supernatant was determined by the ELISA sandwich method (which will be described below) using Human interleukin-2 measurement kit (Japan Immunoresearch Laboratories Co., Ltd.) and the amounts of IL-2 in the supernatant of the treated cells were compared with those for untreated cells (in some cases, hereinafter called IL-2 expression-uninduced cells).

Wells in a 96-well plate (antibody plate) on which anti-human IL-2 monoclonal antibodies were immobilized were washed with washing solution twice, and 150 μl of buffer solution was added to each well to be used. To each well was added 50 μl of the supernatant of culture medium or purified IL-2 (0–1,600 pg/ml, standard human IL-2 protein in Human IL-2 measurement kit), they were incubated at 37° C. overnight. The reaction solution in each well was removed, and the well was washed with washing solution three times. The first antibody (anti-human IL-2 rabbit serum) solution was added at 100 μl/well, and incubated at room temperature for 2 hours. The antibody solution in each well was removed, followed by washing with the washing solution three times.

The second antibody (peroxidase labeled anti-rabbit IgG antibodies) solution was added at 100 μl/well, and incubated at room temperature for 2 hours. The antibody solution in each well was removed. After the well was washed with washing solution three times, and fully dried. A peroxidase substrate solution, o-phenylenediamine dissolved in 0.015% hydrogen peroxide was added at 100 μl/well, and was allowed to react at room temperature for 10–20 minutes. 100 μl of 1N $H_2SO_4$ was added to each well to stop the reaction. Absorbance at 492 nm in each well was measured using a microplate reader. IL-2 in the culture supernatant was quantified based on the calibration curve created from the values of absorbance of standard IL-2.

6157±168 (pg/ml/$10^7$ cells) of IL-2 were detected in the culture medium of IL-2 expression-induced cells, while the amount of IL-2 was less than the detectable range for IL-2 expression-uninduced cells (<0.1 pg/ml/$10^7$ cells).

(7) Measurement of Amounts of IL-2 Gene Expression

For experimental materials, this experiment required purified IL-2 RNA as a reference sample, the total RNA extracted from Jurkat B6–1 cells as a measurement sample, and ribonucleic acid probe of IL-2 (RNA probe for IL-2) labeled with digoxigenin for the detection of IL-2 RNA or IL-2 mRNA. They were obtained using the methods in the following (a)–(c).

(a) Standard IL-2 RNA

Human IL-2 RNA (1 μg/μl) synthesized in (2) was diluted by $10^4$, $10^5$, $10^6$, and $10^7$ times with 1×dilution buffer (RNase-free sterile distilled water: 20×SSC: formamide=5:3:1). The diluted RNA solutions were heated at 68° C. for 10 minutes, then quenched on ice, and then used for blotting.

(b) Total RNA of Jurkat E6-1 Cells

Total RNA of Jurkat E6-1 cell was extracted using an RNeasy kit (QIAGEN Inc.). Under the conditions shown in (5), cells treated with the IL-2 expression-inducing agent for 0, 24, 48, 72, and 96 hours (0.8–1.2×$10^7$ cells) were recovered as precipitates by centrifugation at 1,500 rpm for 5 minutes. The cells were suspended in 1,000 μl of homogenization buffer containing 10 μl of β-mercaptethanol and were denatured sufficiently by repeating a manipulation of suction/emission with a syringe in 18-gauges. To the homogenate was added 1,000 μl of 70% ethanol, then it was applied to a column for RNA absorption, centrifuged at 4,000×g for 5 minutes, and then the column was washed once by centrifugation after the addition of washing buffer.

RNase-free sterile distilled water was added to the column to elute the absorbed RNA. To the eluted RNA solution was added 0.1 times volume of 4M sodium acetate and an equal volume of isopropanol. Then RNA was recovered as a precipitate by centrifugation at 15,000×g for 15 minutes and. After the RNA was dissolved in the RNase-free sterile distilled water, it was diluted with an equal volume of 2×dilution buffer (RNase-free sterile distilled water: 20×SSC: formamide=1:6:2), heated at 68° C. for 10 minutes and then quenched quickly.

(c) Digoxigenin (DIG)-Labeled RNA Probe for IL-2 RNA

DIG-labeled RNA probe for IL-2 RNA was synthesized using a DIG RNA Labeling kit (Boehringer Mannheim Inc.). 10 μg of human IL-2 cDNA recombinant plasmid DNA (pTCGF#2), linearized by EcoRI digestion, was purified by ethanol precipitation. After removing the enzyme protein denatured with phenol/chloroform, the purified DNA was used as a template for RNA probe synthesis. The template DNA (5 μg) and 1.8 mM ATP, 0.9 mM CTP, 0.7 mM GTP, 1.1 mM UTP, and 0.58 mM UTP (DIG-labeled) were mixed in the presence of T7 RNA polymerase. The mixture was incubated at 37° C. for 2 hours. Then, DNase I solution was added and reacted for 10 minutes to degrade the template DNA. To the reaction solution were added 0.1 times volume of 5M sodium acetate and an equal volume of isopropanol, and the synthesized RNA was recovered by centrifugation at 15,000×g for 15 minuts. The RNA was then dissolved in RNase-free sterile distilled water.

(d) Measurement of Amounts of IL-2 Gene Expression

Using the materials obtained from (a)–(c), the amount of IL-2 gene expression was measured. The cellular total RNA solution and standard IL-2 RNA solution were dotted to a nylon membrane, and washed with 5×SSC twice. Then, the RNA on the nylon membrane was fixed using a UV-Crosslinker (Biorad Inc.). The nylon membrane, prehybridization buffer (5×SSC, 5% SDS, 50 mM sodium phosphate (pH 7.0), 50% formamide, 2% Blocking Reagent (Boehringer Mannheim Inc.), and 1% N-lauryl sarcosinate were enclosed into a HybriBag (Iuchi Inc., Hot water resistant bag: L) and incubated at 68° C. for one hour.

DIG-labeled probe for IL-2 RNA was diluted with a prehybridization buffer to give a final concentration of 100 ng/ml, boiled for 10 minutes and then quenched to prepare hybridization solution. Prehybridization solution in HybriBag was replaced with the hybridization solution, and hybridization was carried out at 68° C. overnight. The nylon membrane was washed with 2×Washing solution (2×SSC, 0.1% SDS) twice for 5 minutes each, and with 0.2×Washing solution (0.2×SSC, 0.1% SDS) at 68° C. for 15 minutes each. After washing the nylon membrane with Buffer I (100 mM maleic acid, 150 M NaCl (pH 7.5)) for one minute, the nylon membrane was incubated with Buffer II (Blocking Reagent (Boehringer Mannheim Inc.) was diluted to 1% with buffer 1).

The amounts of hybrid formed with DIG-labeled probes and IL-2 RNA, were estimated by chemiluminescence emitted from the hybrids using DIG Luminescent Detection kit (Boehringer Mannheim Inc.) as follows. The nylon membrane was treated with alkalinephosphatase-labeled anti-DIG antibodies (150 mU/ml in Buffer II solution), at room temperature for 1 hour. Then the nylon membrane was washed with Buffer I twice for 15 minutes each, and packed into a bag (LIFETECHNOLOGIES Inc., Photogene development folder) with 250 μM of substrate solution which had been obtained by diluting CSPD (disodium 3-(4-methoxyspiro[1,2-dioxetane-3,2'-(5'-chloro)tricyclo [3.3.1.13,7]decan]-4-yl) phenylphosphate) with Buffer III (0.1M Tris, pH 9,7, 0,1M NaCl, 0.05 $MgCl_2$). The number of photons emitted from the enzymatically degraded substrate was counted with ARGUS 50 (Hamamatsu Photonics). A calibration curve indicating the relation between the number of photon and the amount of standard IL-2 RNA was created. Based on the curve, the amount of IL-2 mRNA out of total cellular RNA in the cell was determined. From the amount of IL-2 mRNA (mol) obtained and the number of cells used for extraction of the total cellular RNA, the number of IL-2 mRNA molecules per single cell was determined (FIG. 19).

Figure 9:
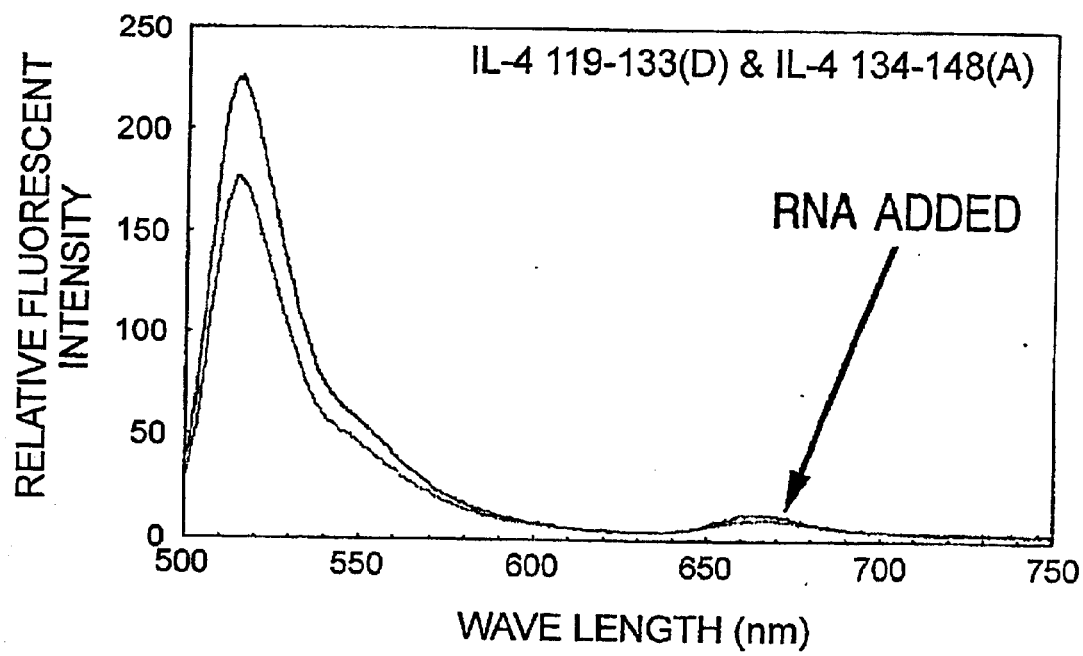
FIG. 9 is a graph of a fluorescence spectrum of a hybrid formed by the donor probe IL-4 119–133(D) and the acceptor probe IL-4 134–148(A) being adjacently hybridized to IL-4 RNA.
Figure 10:
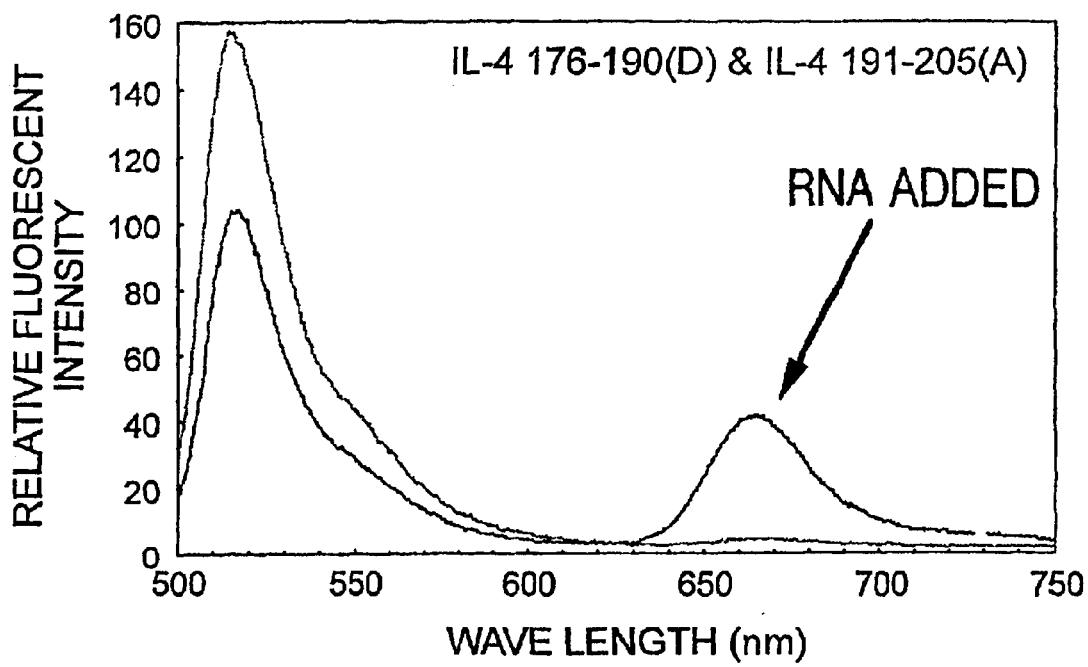
FIG. 10 is a graph of a fluorescence spectrum of a hybrid formed by the donor probe IL-4 176–190(D) and the acceptor probe IL-4 191–205(A) being adjacently hybridized to IL-4 RNA.
Figure 11:
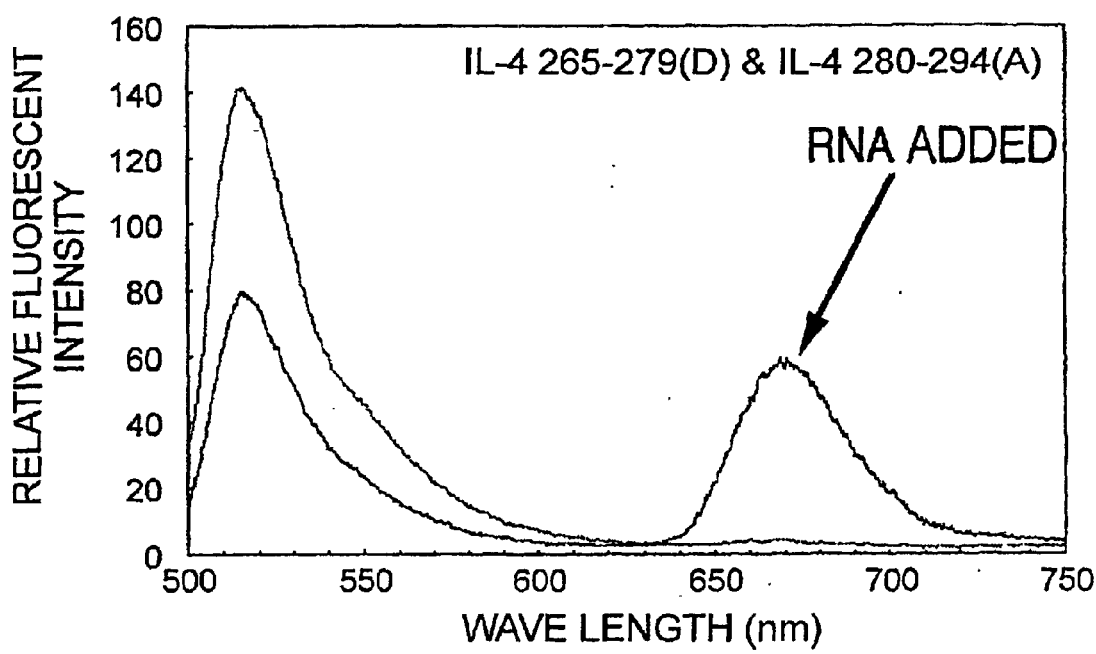
FIG. 11 is a graph of a fluorescence spectrum of a hybrid formed by the donor probe IL-4 265–279(D) and the acceptor probe IL-4 280–294(A) being adjacently hybridized to IL-4 RNA.
Figure 12:
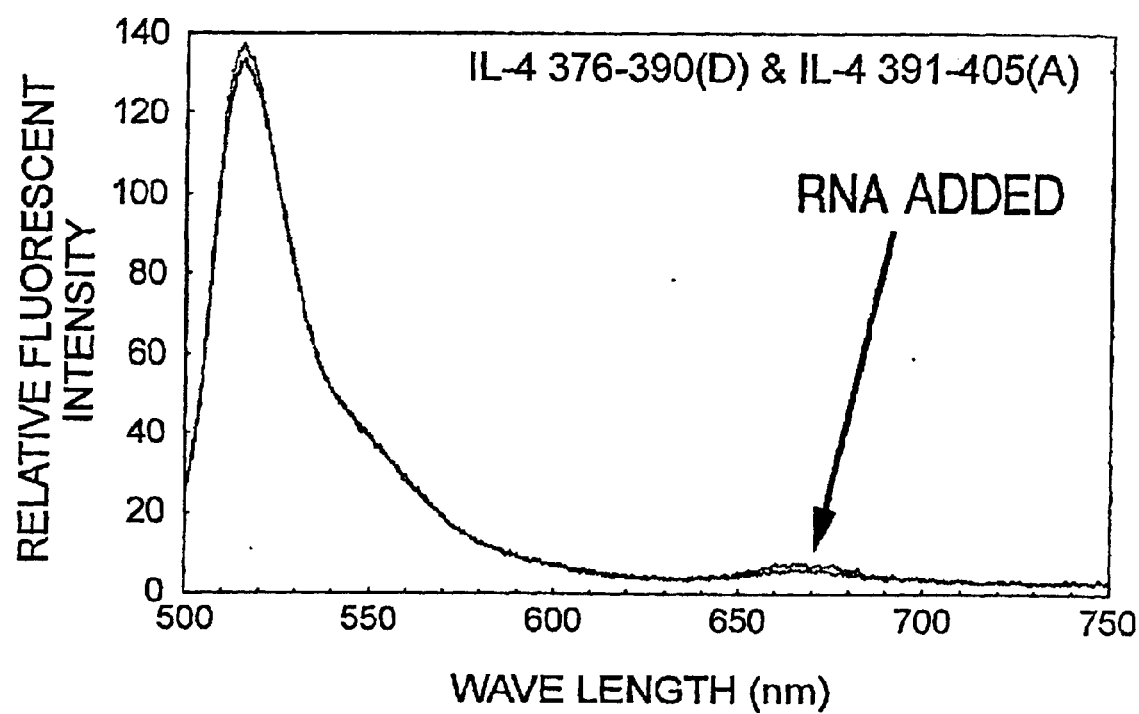
FIG. 12 is a graph of a fluorescence spectrum of a hybrid formed by the donor probe IL-4 376–390(D) and the acceptor probe IL-4 391–405(A) adjacently hybridized to IL-4 RNA.

As shown in FIG. 9, the numbers of IL-2 mRNA molecules in the single cell where the cells were treated for inducing IL-2 expression for 0, 24, 48, 72, and 96 hours were <0.29, $(0.76\pm0.17)\times10^4$, $(1.11\pm0.40)\times10^4$, $(1.22\pm0.67)\times10^4$, and $(1.20\pm0.28)\times10^4$, respectively. The cells treated for 72 hours (3 days) were found to contain the maximum number of IL-2 mRNA. In addition, the contents of extracellular IL-2 ($pg/ml/10^7$ cells) of the cells treated for the above described periods were <0.32, $1,032\pm25$, $2,433\pm533$, $2,688\pm194$, and $2,531\pm283$, respectively. Therefore, it was suggested that more IL-2 molecules had been secreted from the cells with higher efficiency in IL-2 gene expression.

(8) Intracellular Hybridization Between Each Probe and IL-2 mRNA in Human T-Cell Leukemia Strain Jurkat E6-1 Cells Induced the Expression of IL-2 Gene For IL-2 expression-induced cells the IL-2 gene expression of which was induced by treatment with anti-CD3 antibodies, anti-CD28 antibodies, and PMA for 3 days as described in (5), detection of the hybridization between intracellular IL-2 mRNA and each IL-2 probe was performed by IST (In Situ Transcription) as follows.

The IL-2 expression-induced and -uninduced Jurkat E6-1 cells ($5\times10^5$ cells/ml) were washed with PBS(-) three times, and suspended with 1 ml of PBS(-), and the suspension was mounted on 12 mm of a cover glass (poly-L-lysine was coated on the bottom) to prepare a monolayer of cells. The cells were exposed to 0.5% Triton-X100 solution for 90 seconds at room temperature to permeabilize the cells. After the permeabilized cells were quickly washed with PBS(-), 10 $\mu$M (final concentration) of probes corresponding to SEQ ID NO: 1–10 in Table 1 (unlabeled with dye), oligo dA (deoxythymidine oligonucleotide, unlabeled with dye) or oligo dA (deoxyadenine oligonucleotide, unlabeled with dye) were added, and incubated for one hour at room temperature. The cells were washed with PBS(-) quickly, and fixed with 4% paraformaldehyde solution at room temperature for 15 minutes.

The cells were washed with 1×SSC three times; 1 mM deoxyribonucleotide solution (Boehringer Mannheim Inc.) containing 0.35 mM of DIG (digoxigenin)-labeled dUTP and 1 $\mu$l reverse transcriptase (Toyobo, Inc.) were added to the cells; and they were incubated for 2 hours at 30° C. The cells were washed with 1×SSC three times, and treated with Blocking buffer [Blocking Reagent (Boehringer Mannheim Inc.) dissolved in maleic acid buffer solution so that its ratio would be equal to 1 (w/v) %]. The cells were washed with maleic acid buffer solution three times. FITC (Fluorescein-isothiocyanate) labeled anti-DIG antibody (which was diluted with Blocking buffer up to 1 $\mu$g/ml) was added to the cells and then the cells were incubated for 30 minutes at room temperature. The cover glass was washed with PBS(-) three times, observed under a fluorescence microscope, and the total fluorescence intensity in the visual field (relative value) was measured.

Figure 20:
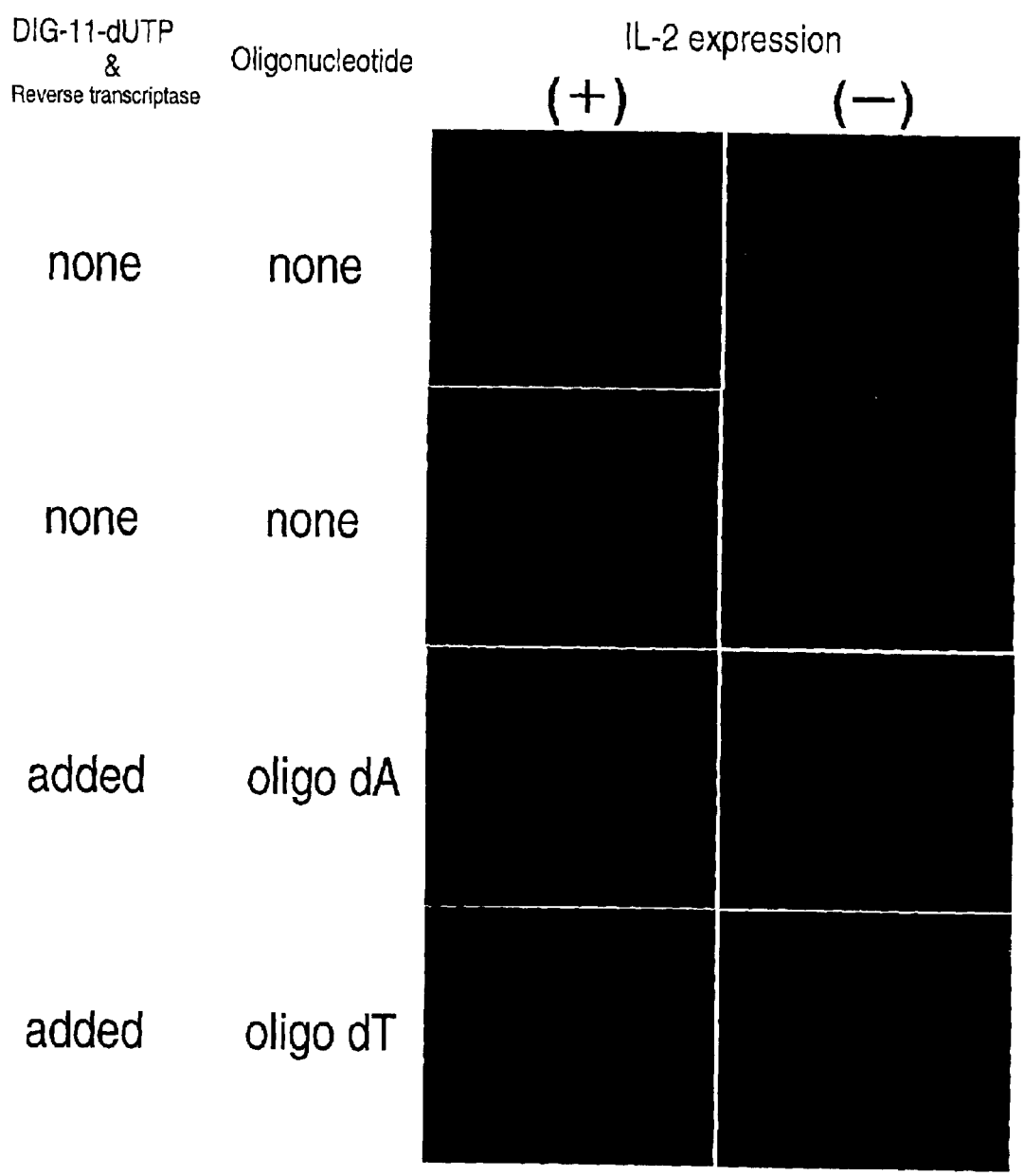
FIG. 20 is a set of fluorescence micrographs obtained for those to which DIG-labeled dUTP and reverse transcriptase were added after oligonucleotides (oligo dT or oligo dA) had been introduced to IL-2 expression-induced cells or IL-2 expression-uninduced cells in the fixed state, those to which the oligonucleotides were not introduced thereafter, and those to which neither of them was introduced nor was added.
Figure 22:
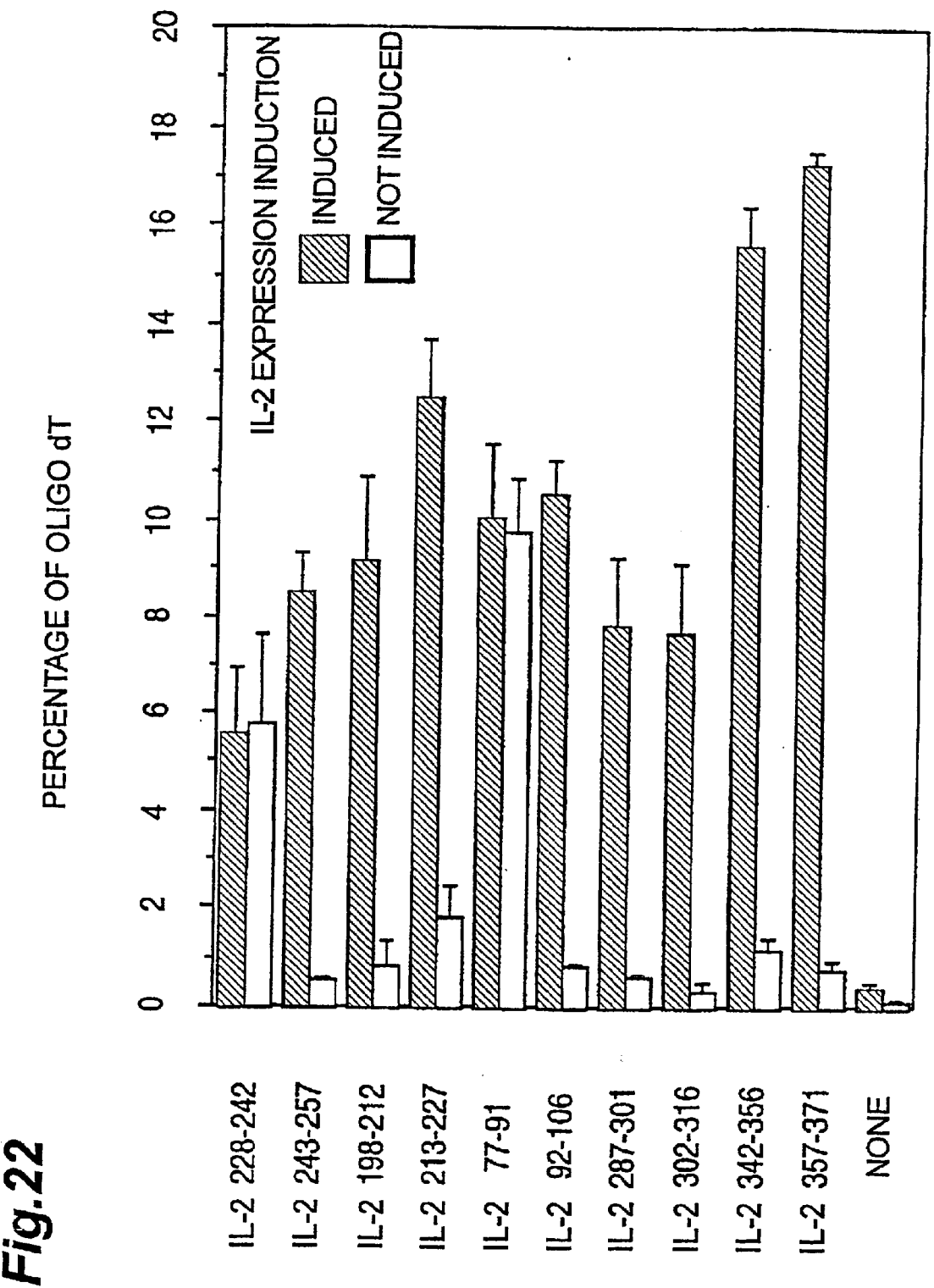
FIG. 22 is a graph showing the results obtained when hybrids were formed between IL-2 mRNA in the IL-2 expression-induced cells or IL-2 expression-uninduced cells in the fixed state and various probes (non-fluorescent markers) were fluorescently detected, and the fluorescence intensities were normalized based on the values of fluorescence intensity emitted from the fluorescent labeled compounds formed between total mRNA in said cells and oligo dT.

FIGS. 20 and 21 show the fluorescence micrographs obtained. FIG. 20 shows a fluorescence micrographs where the hybrids formed between all of the cellular mRNA and oligo dT were fluorescently detected in the fixed IL-2 expression-induced cells and -uninduced cells. FIG. 20 also shows the control experiments in cases where oligo dA was added instead of oligo dT, or where both DIG-labeled dUTP and reverse transcriptase required for fluorescent labeled complex were not added. FIG. 21 shows fluorescence micrographs in which hybrids, formed between IL-2 mRNA and each probe (fluorescently unlabeled), were fluorescently labeled in the fixed IL-2 expression-induced and -uninduced. In FIG. 21, two fluorescence images for each probe are shown for IL-2 expression-induced and -uninduced cells. FIG. 22 shows the normalized intensity (%) of each probe out of the fluorescence intensity obtained from the addition of oligo dT to the cells, the relative fluorescent intensity per cell was worked out from the fluorescence intensities (mean value±SE) divided by the number of cells in the corresponding phase contrast micrograph.

IL-2 342–356 and IL-2 357–371 were shown to hybridize with intracellular IL-2 mRNA most efficiently. As these two probes are complementary to an adjacent site on IL-2 mRNA, if one of the two probes is labeled with an fluorescent energy donor dye and the other is labeled with an fluorescent energy acceptor dye, FRET fluorescence caused by intracellular hybridization could be detected specifically.

(9) Intracellular Hybridization (ISH) of Donor Probes and Acceptor Probes With IL-2 mRNA in IL-2 Expression-Induced Cells In the experimental results by IST in (8), the probes were introduced into almost all the cells uniformly in a visual field of a fluorescence microscope. The method for introducing probes in (8) was also used when fluorescent labeled probes of donors and acceptors were introduced into cells. Hybridization between these probes and intracellular IL-2 mRNA was detected as FRET fluorescence. Various sets of probes were examined. Since this method modifies the IST method, it is called ISH (In Situ Hybridization).

Figure 23:
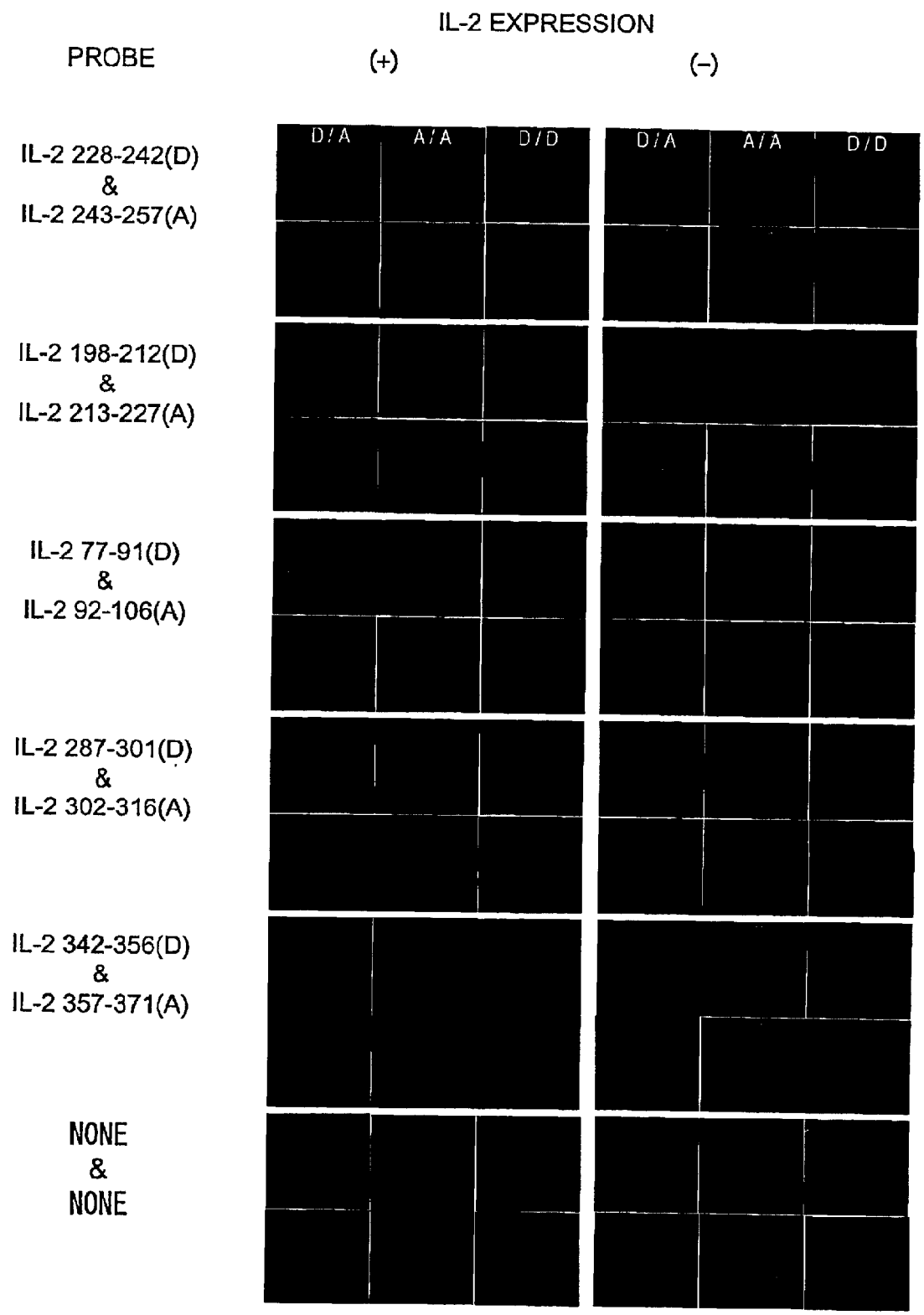
FIG. 23 is a set of fluorescence micrographs showing D/A, D/D and A/A images of hybrids formed by the three components, IL-2 mRNA in IL-2 expression-induced cells or IL-2 expression-uninduced cells in the fixed state, respective donor probes and respective acceptor probes upon excitation of the donor fluorescent dyes of the hybrids.

A solution of 2 $\mu$M (final concentration) of a donor probe labeled with Bodipy 493/503 and an acceptor probe labeled with XRITC was added to IL-2 expression-induced cells as well as to IL-2 expression-uninduced cells, both of which were provided with material permeability in the cellular transmembranes as described in (8), and they were incubated for one hour at room temperature. As sets of donor probes and acceptor probes, IL-2 228–242(D) and IL-2 243–257 (A), IL-2 198–212(D) and IL-2 213–227(A), IL-2 77–91(D) and IL-2 92–106(A), IL-2 287–301(D) and IL-2 302–316 (A), and IL-2 342–356(D) and IL-2 357–371(A) were used. After the cells were washed with PBS(-), the cells were fixed with 4% paraformaldehyde solution for 15 minutes at room temperature. The cover glass was washed with PBS(-) three times before fluorescence microscopy. Three kinds of fluorescence images were obtained as follows. These are the fluorescence of A emitted from the cells when the excitation light of A (energy acceptor dye) was irradiated to the cells (in some cases, hereinafter called A/A image), the fluorescence of D emitted from the cells when the excitation light of D (energy donor dye) was irradiated to the cells (hereinafter, sometimes called D/D image), and the fluorescence of A emitted from the cells when the excitation light of D was irradiated to the cells (in some cases, hereinafter called D/A image). The D/A image represents fluorescence caused by FRET. The maximum intensity of FRET fluorescence was obtained when IL-2 342–356(D) and was used as a donor probe and IL-2 357–371(A) as an acceptor probe. These fluorescence micrographs are shown in FIG. 23. In FIG. 23, two sets of D/A, A/A, and D/D images for each pair of probes are shown for IL-2 expression-induced and -uninduced cells. In this figure, the images in which probes were not introduced are also shown as a control experiment.

Figure 24:
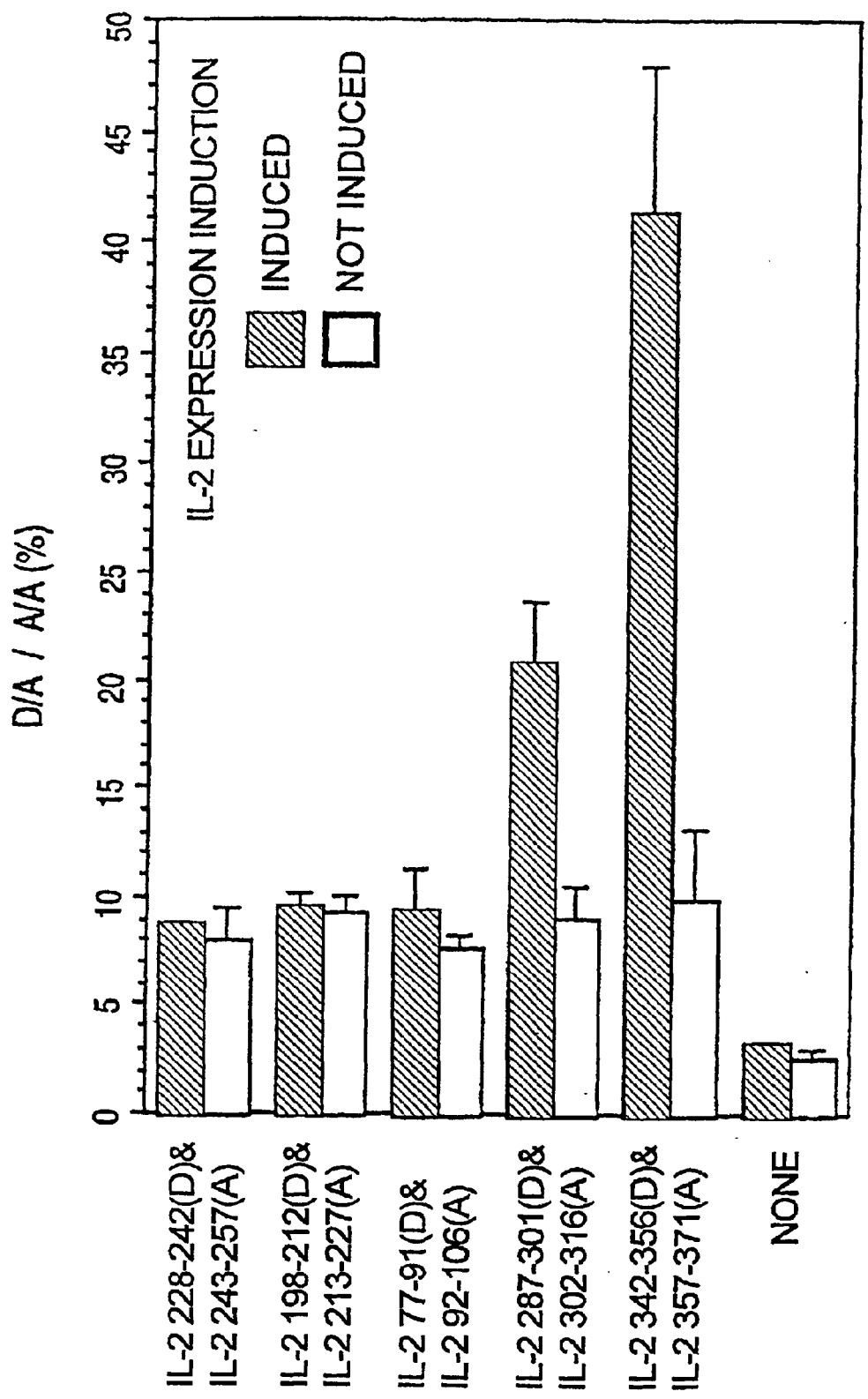
FIG. 24 is a graph showing the results obtained when the fluorescence of the acceptor fluorescence dyes was measured upon excitation of the donor fluorescent dyes of the hybrids formed by the three molecules, IL-2 mRNA in IL-2 expression-induced cells or IL-2 expression-uninduced cells in the fixed state, respective donor probes and respective acceptor probes, and the measured fluorescence was standardized based the measured values of fluorescence of the acceptor fluorescent dyes upon excitation of the acceptor fluorescent dyes representing all the acceptor probes in said cells.

The total fluorescence intensity in a D/A image, acceptor fluorescence of FRET with donor excitation, and a A/A image, acceptor fluorescence with acceptor excitation, were obtained. Then, the average fluorescence intensity value per cell in a D/A and A/A image was estimated as the total fluorescence intensity divided by the number of cells in a corresponding image. In order to evaluate the intracellular hybridization efficiency, the average D/A value per cell/the average A/A value per cell, representing the ratio of the hybridized acceptor probes to IL-2 mRNA to the total probes, were obtained. The value of (D/A)/(A/A) (%) for each pair of probes is shown in FIG. 24. From the results in (8) and (9), it is suggested that IL-2 342–356(D) and IL-2 357–371(A) hybridize to the target mRNA in the cells individually as well as adjacently.

(10) Intracellular Hybridization When Donor Probes and Acceptor Probes Were Introduced Into Live IL-2 Expression-Induced Cells Throughout the results of (3A)-(9), IL-2 342–356(D) and IL-2 357–371(A) were selected as probes to detect IL-2 mRNA in live cells. These fluorescently labeled probes were introduced into live cells expressing IL-2 genes; and the hybridization was specifically measured based on the changes in FRET fluorescence.

As described in (5), IL-2 expression-induced cells which were prepared by the treatment with anti-CD3 antibodies, anti-CD28 antibodies and PMA for three days, and -uninduced cells, were washed with ice-cold PBS(-) twice, and suspended in PBS(-) to $1 \times 10^7$ cells/ml. Then, 0.9 ml of the cell suspension was transferred into a cuvette for electroporation; and 5.4 nmol (final concentration; 6.0 $\mu$M) of Bodipy493/503-labeled donor probe IL-2 342–356(D) and 5.3 nmol (final concentration; 5.86 $\mu$M) of XRITC-labeled acceptor probe I1-2 357–371(A) were added; and the cells were pulsed at 250 V, 975 $\mu$F. After the cell suspension was filtered through 70 $\mu$m of Cell Strainer (Falcon) and centrifuged mildly, the cells were resuspended with PBS(-). Further the suspended solution was filtered through 40 $\mu$m of Cell Strainer (Falcon); the re-passed solution was centrifuged and resuspended to remove debris including dead cells as much as possible; and the suspended solution was observed under a fluorescence microscope.

Figure 25:
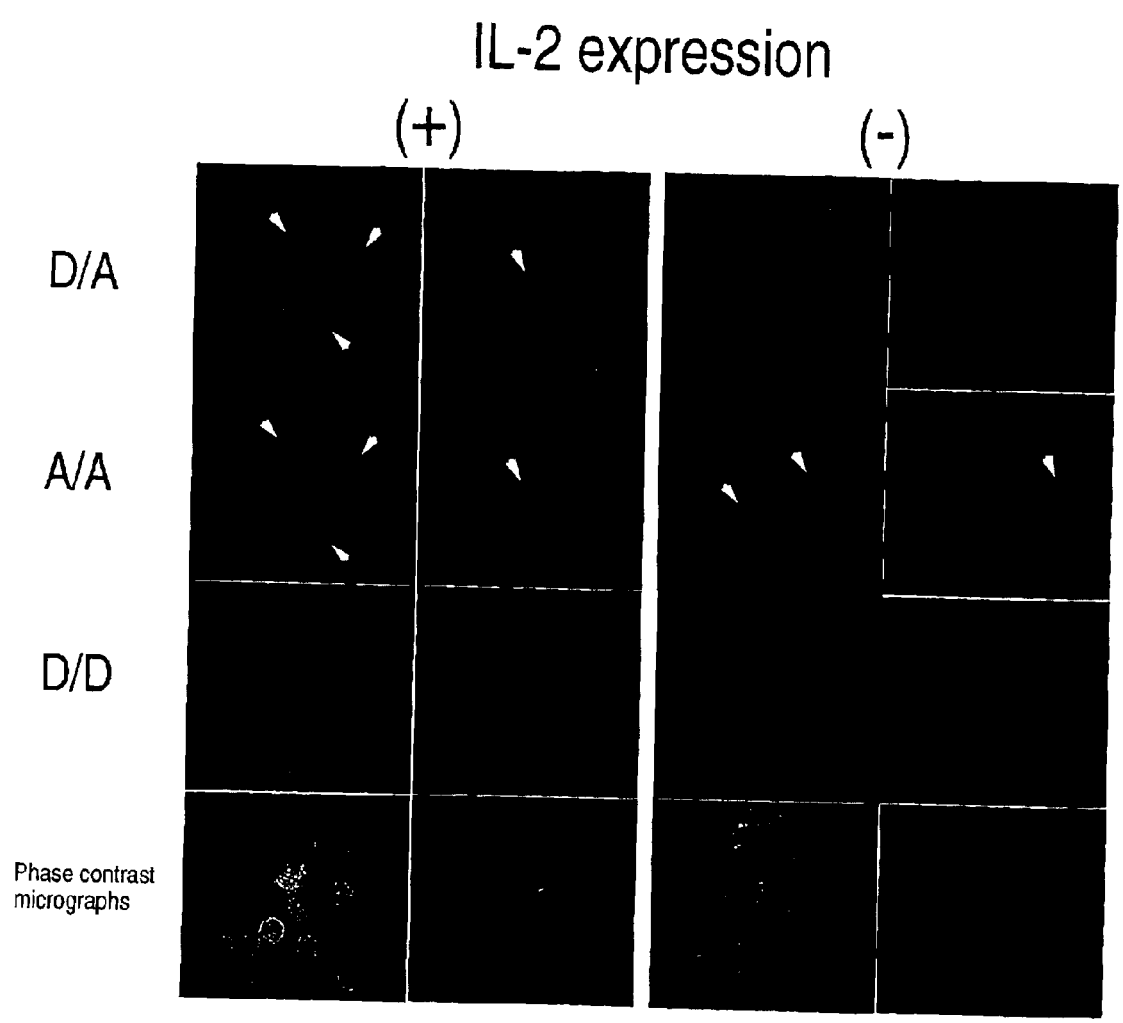
FIG. 25 is a set of fluorescence micrographs of D/A, D/D and A/A images of a hybrid formed by the three molecules, IL-2 mRNA in IL-2 expression-induced cells or IL-2 expression-uninduced cells in the living state, IL-2 342–356 (D) and IL-2 357–371(A), and the corresponding phase contrast micrograph.

The results were shown in FIG. 25. FIG. 25 shows A/A, D/D, and D/A images, and the corresponding phase contrast image of IL-2 expression-induced and -uninduced cells. In FIG. 25, two sets of A/A, D/D, D/A images, and the corresponding phase contrast images for each pair of probes were shown. One to three cells out of 20–22 cells were D/A-positive cells in the visual field for IL-2 expression-induced cells, suggesting that the donor probe and the acceptor probe adjacently hybridize to IL-2 mRNA. On the other hand, no D/A-positive cells were observed for IL-2 expression-uninduced cells.

(11) Selective Separation of Cells Which Have Expressed IL-2 Genes by Flow Cytometry Utilizing the differenciated intensities of FRET-fluorescence between IL-2 expression-induced and -uninduced cells based on the specific hybrid formation among the donor probe, the acceptor probe, and IL-2 mRNA, it was attempted to separate IL-2 expressing cells from non-expressing cells as follows.

The cell suspensions of IL-2 expression-induced cells prepared as described in (9) and those of -uninduced cells were mixed with the ratios of 100:0, 0:100, 50:50, and 20:80, respectively. Then, 0.9 ml of the mixture was put into a cuvette; 16.2 nM (final concentration; 18.0 $\mu$M) of Bodipy493/503-labeled donor probe IL-2 342–356(D) and 14.7 nmol (final concentration; 16.4 $\mu$M) of Cy5-labeled acceptor probe IL-2 357–371(A) were added. The mixture with the probes was pulsed as described in (9). Live cells were collected and were applied to a flow cytometer, an experimental device for flow cytometry (FACSCalibur, BECTON DICKINSON Inc.).

At a position in flow path, the excitation light for an energy donor fluorescence dye (Bodipy493/503) was irradiated to the cells. Relative fluorescence intensity emitted from acceptor fluorescence dye (Cy5), representing FRET fluorescence based on the hybridization was measured together with relative intensity of Bodipy493/503. Each cell was plotted as a dot in a diagram with the X-axis, the intensity of Bodipy493/503 (FL1-Height) and Y-axis, that of Cy5 (FL3-Height). Among these plots, a group of dots with the highest value of FL3-Height representing a group of fluorescing cells based on hybridization, was designated as R2. On the other hand, a group of dots, representing the cell size (FSC-Height; forward-scattering light) as well as the complexity in the infrastructure (SSC-Height; side-scattering light) as typical human lymphoid cells was designated as R1 according to the reference value (FACSCalibur Training Manual, BECTON DICKINSON).

Figure 26:
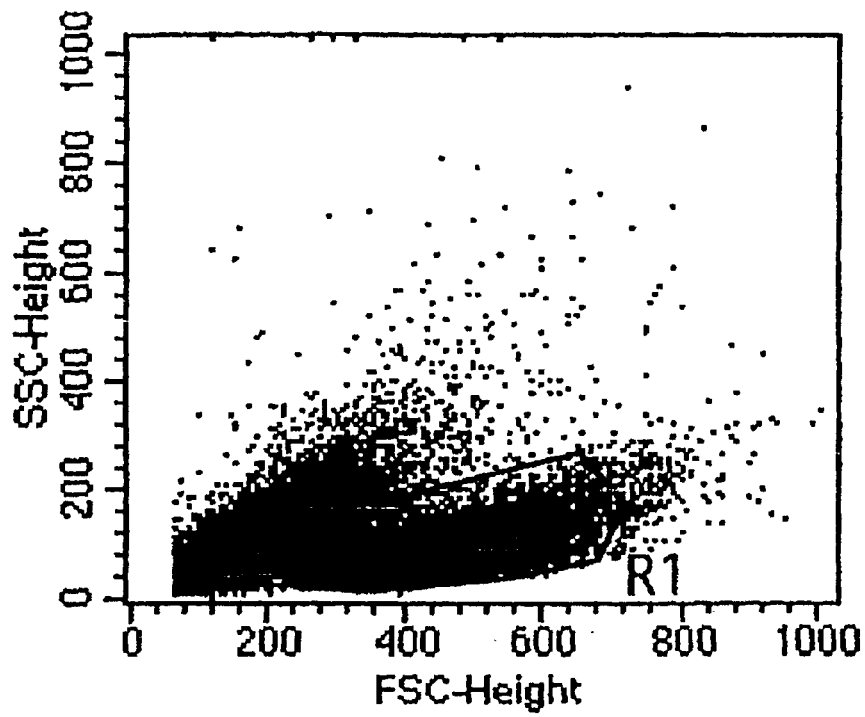
FIG. 26 is a dot plot of the results based on forward scattering light and side scattering light for a cell group where the mixing ratio of the IL-2 expression-induced cells to the IL-2 expression-uninduced cells was 100:0 when subjected to flow cytometry (R1 is the region selected for live cells to be measured).
Figure 27:
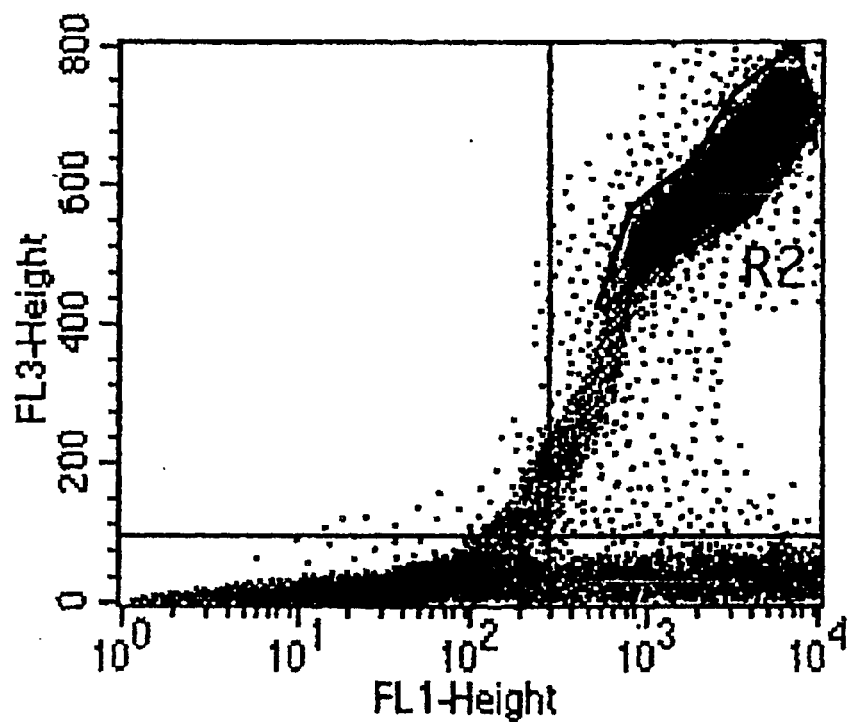
FIG. 27 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 100:0 when subjected to flow cytometry (R2 is the region selected for fluorescing cells due to FRET).
Figure 28:
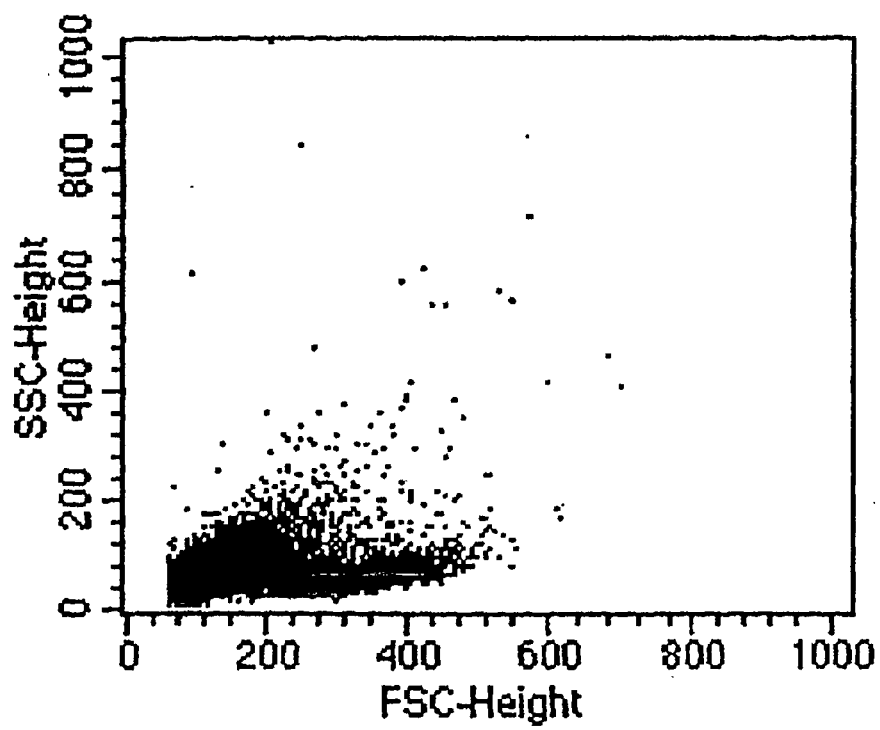
FIG. 28 is a dot plot of the results based on forward scattering light and side scattering light for a cell group where the mixing ratio of the IL-2 expression-induced cells to the IL-2 expression-uninduced cells was 0:100 when subjected to flow cytometry.
Figure 29:
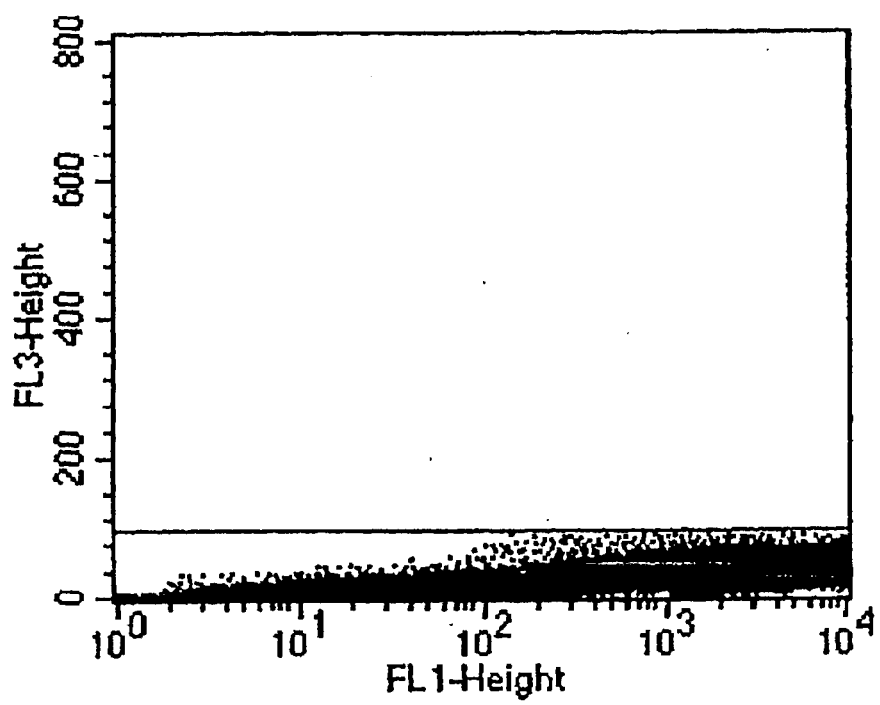
FIG. 29 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 0:100 when subjected to flow cytometry.
Figure 30:
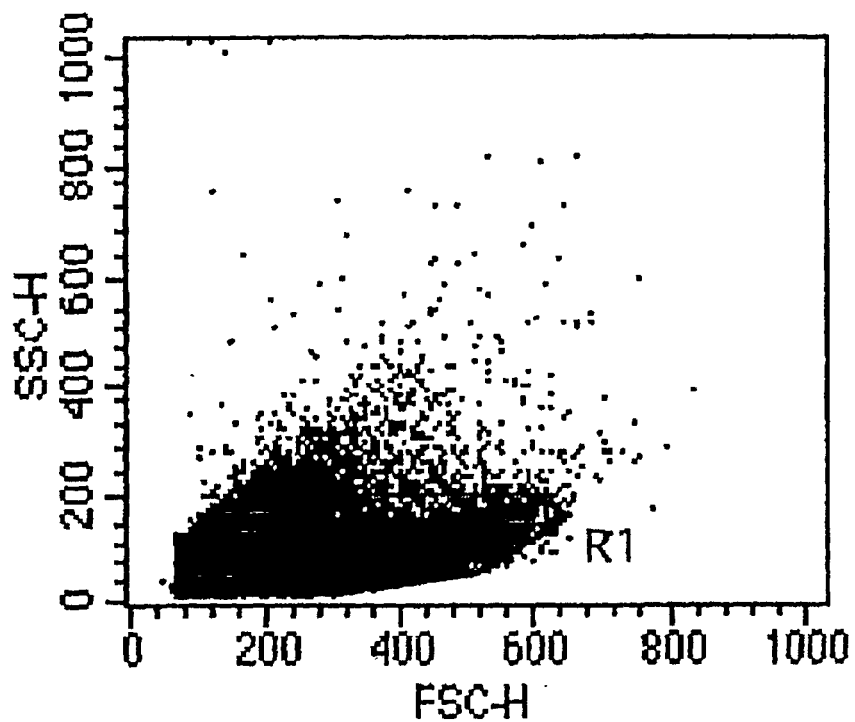
FIG. 30 is a dot plot of the results based on forward scattering light and side scattering light for a cell group where the mixing ratio of the IL-2 expression-induced cells to the IL-2 expression-uninduced cells was 50:50 when subjected to flow cytometry (R1 is the region selected for live cells to be measured).
Figure 31:
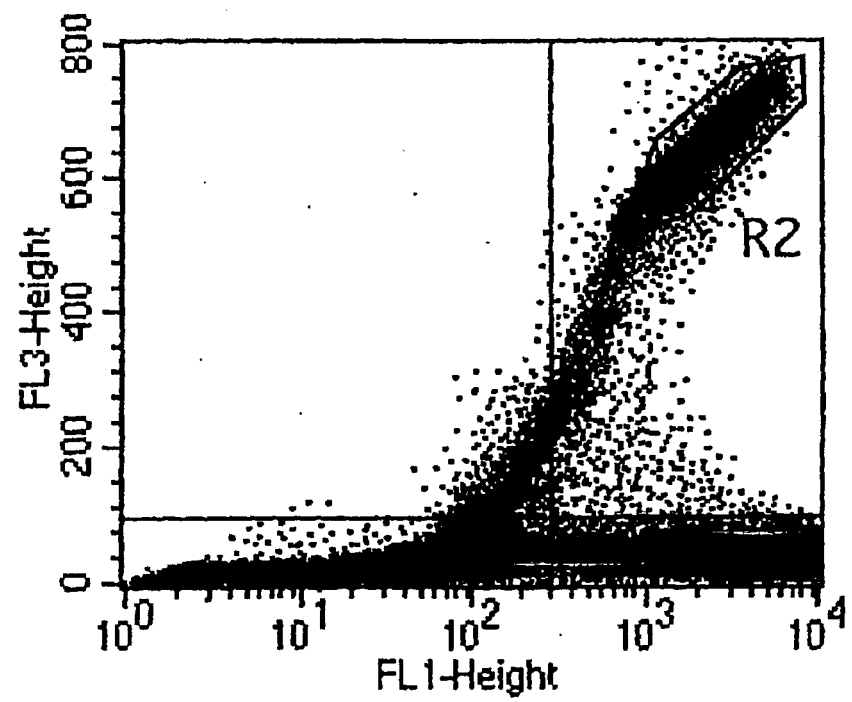
FIG. 31 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 50:50 when subjected to flow cytometry (R2 is the region selected for fluorescing cells due to FRET).
Figure 32:
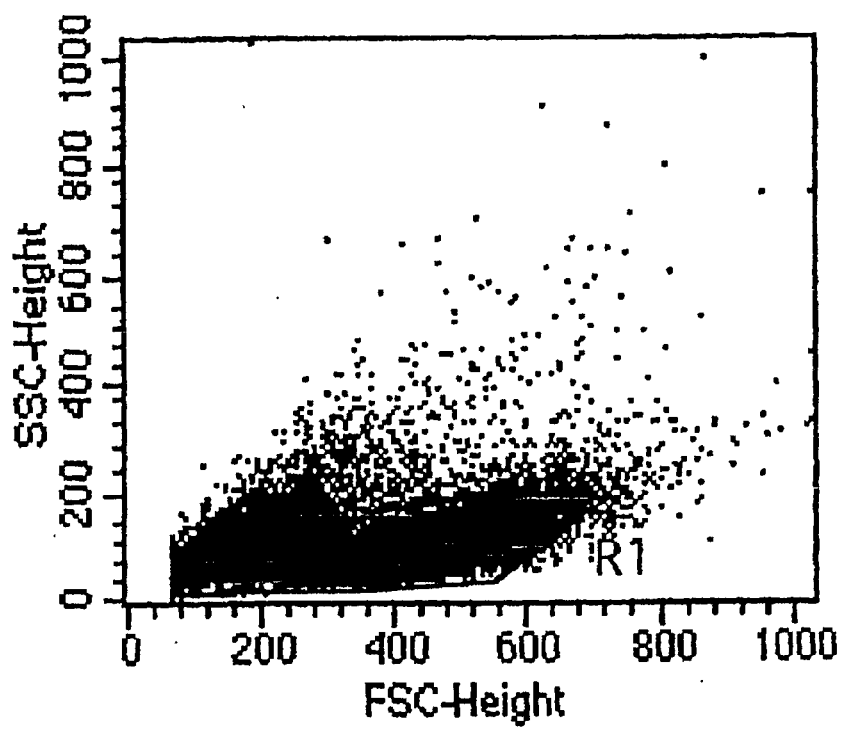
FIG. 32 is a dot plot of the results based on forward scattering light and side scattering light for a cell group where the mixing ratio of the IL-2 expression-induced cells to the IL-2 expression-uninduced cells was 20:80 when subjected to flow cytometry (R1 is the region selected for live cells to be measured).
Figure 33:
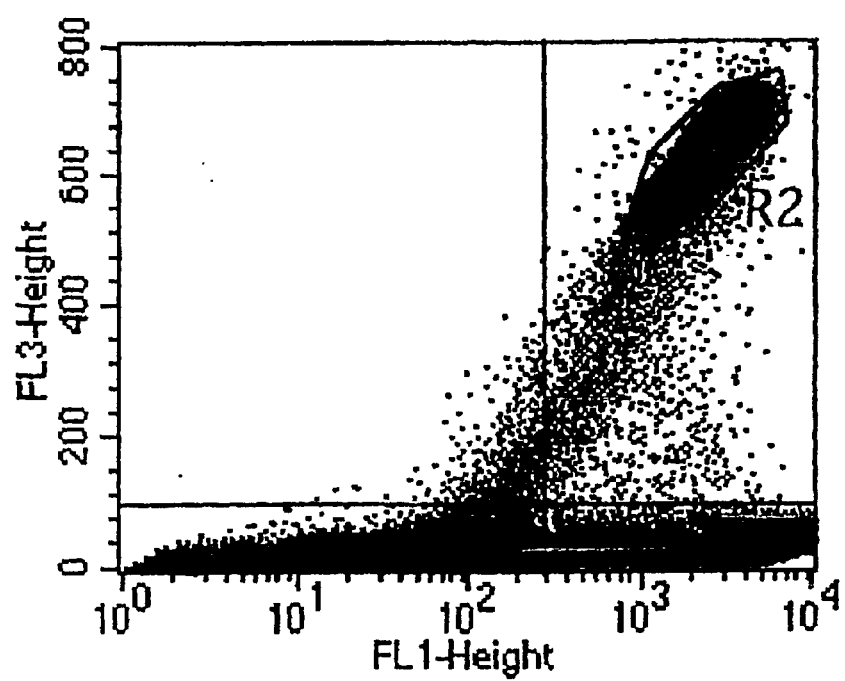
FIG. 33 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 20:80 when subjected to flow cytometry (R2 is the region selected for fluorescing cells due to FRET).

The obtained dot-plots were shown in FIGS. 26–33. FIG. 26 shows a dot plot for FSC-Height and SSC-Height when the mixing ratio of IL-2 expression-induced cells to -uninduced cells was 100 to 0. FIG. 27 shows a dot plot of the cells with the same mixing ratio based on FL1-Height and FL3-Height as in FIG. 26. FIG. 28 shows a dot plot of the cells based on FSC-Height and SSC-Height when the mixing ratio of IL-2 expression-induced cells to -uninduced cells was 0 to 100. FIG. 29 shows a dot plot of the cells based on the FL1-Height and FL3-Height with the same mixing ratio as in FIG. 28. FIG. 30 shows a dot plot of the cells based on FSC-Height and SSC-Height when the mixing ratio of IL-2 expression-induced cells to -uninduced cells was 50 to 50. FIG. 31 shows a dot plot of the cells based on FL1-Height and FL3-Height with the same ratio as in FIG. 30. FIG. 32 shows a dot plot of the cells based on FSC-Height and SSC-Height when the mixing ratio of IL-2 expression-induced cells to -uninduced cells was 20 to 80. FIG. 33 shows a dot plot of the cells based on FL1-Height and FL3-Height with the same mixing ratio as in FIG. 32.

Figure 34:
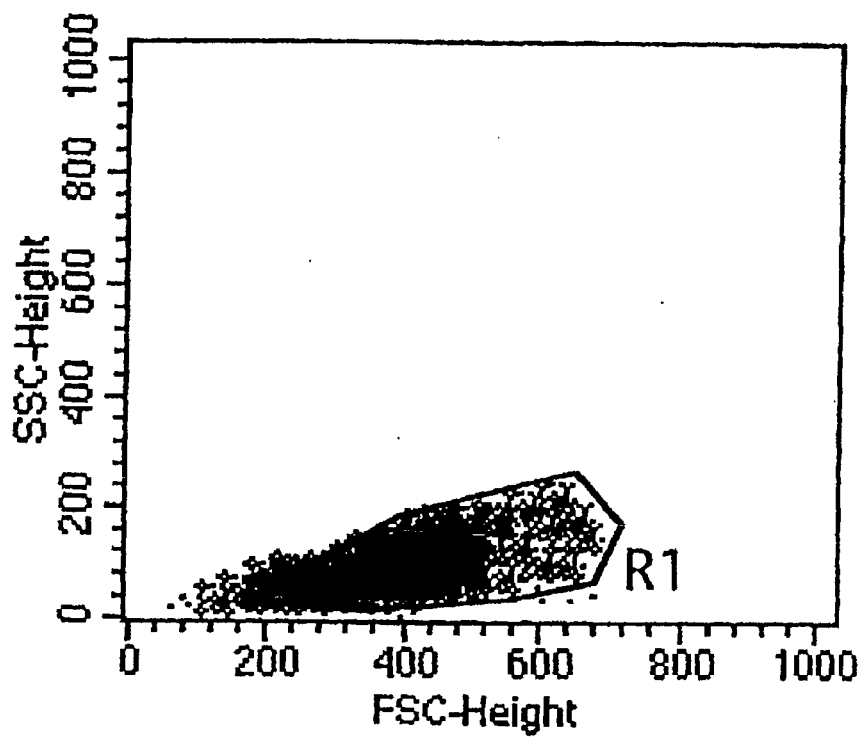
FIG. 34 is a dot plot of the results based on forward scattering light and side scattering light for the cell group where the mixing ratio of the IL-2 expression-induced cells to the IL-2 expression-uninduced cells 100:0 when the selective separation was conducted according to flow cytometry by gating with the R1 gate of FIG. 26 and the R2 gate of FIG. 27, and the resulting cell group was again subjected to flow cytometry.
Figure 35:
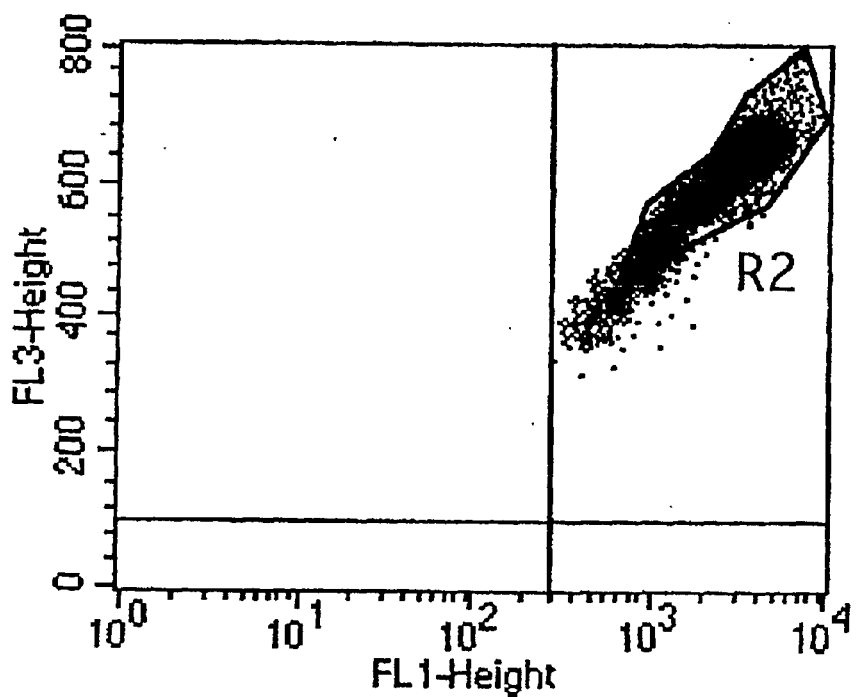
FIG. 35 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 100:0 when the selective separation was conducted according to flow cytometry by gating with the R1 gate of FIG. 26 and the R2 gate of FIG. 27, and the resulting cell group was again subjected to flow cytometry.
Figure 36:
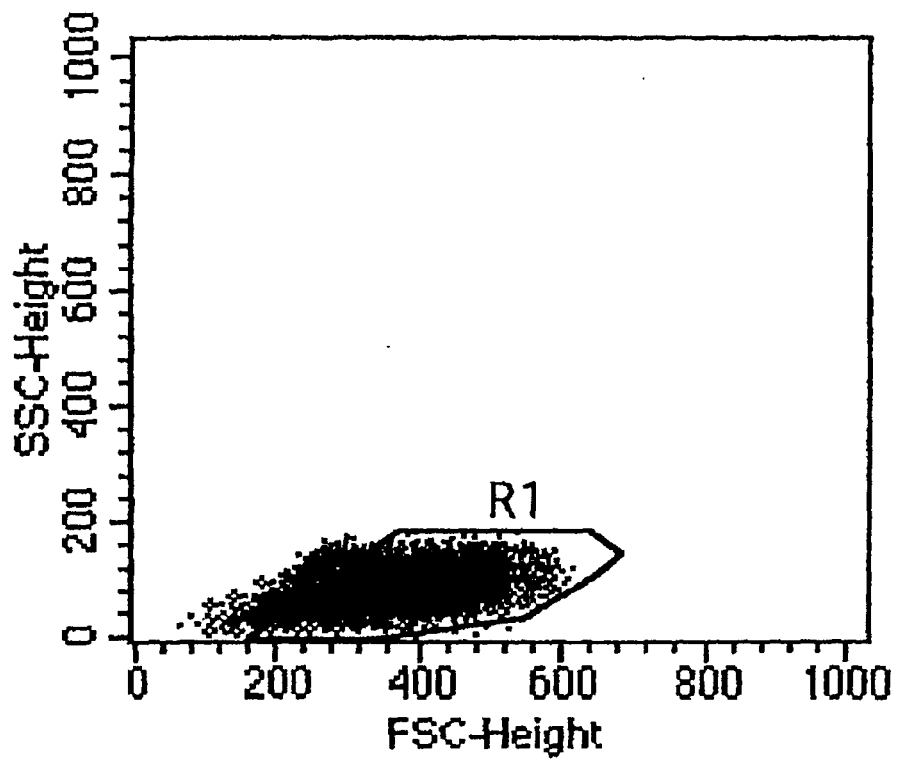
FIG. 36 is a dot plot of the results based on forward scattering light and side scattering light for the cell group where the mixing ratio of the IL-2 expression-induced cells to the IL-2 expression-uninduced cells was 50:50 when the selective separation was conducted according to flow cytometry by gating with the R1 gate of FIG. 30 and the R2 gate of FIG. 31, and the resulting cell group was again subjected to flow cytometry.
Figure 37:
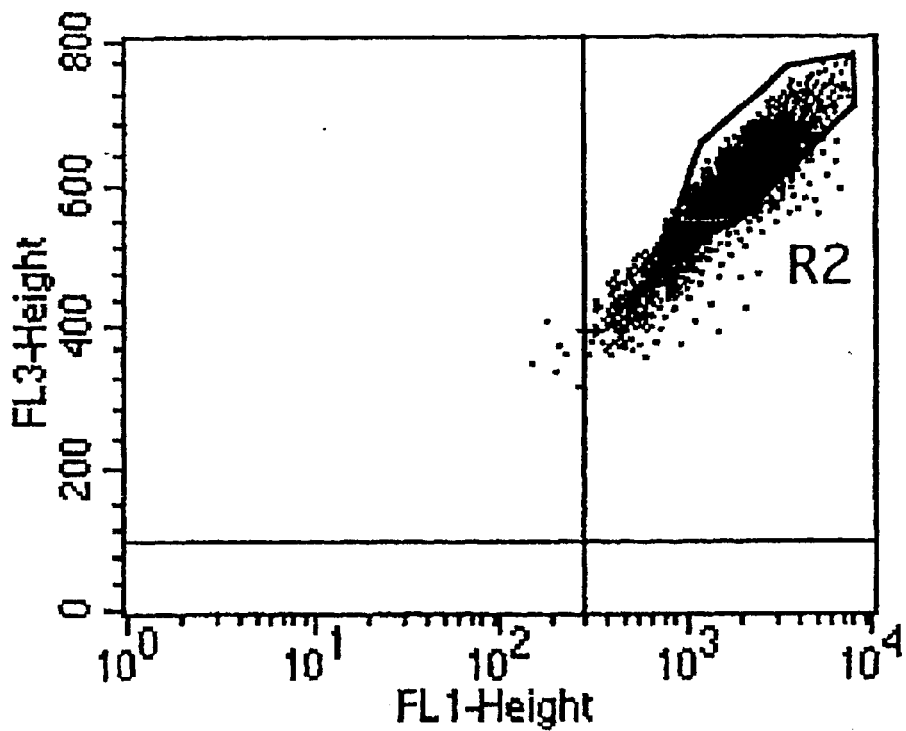
FIG. 37 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 50:50 when the selective separation was conducted according to flow cytometry by gating with the R1 gate of FIG. 30 and the R2 gate of FIG. 31, and the resulting cell group was again subjected to flow cytometry.
Figure 38:
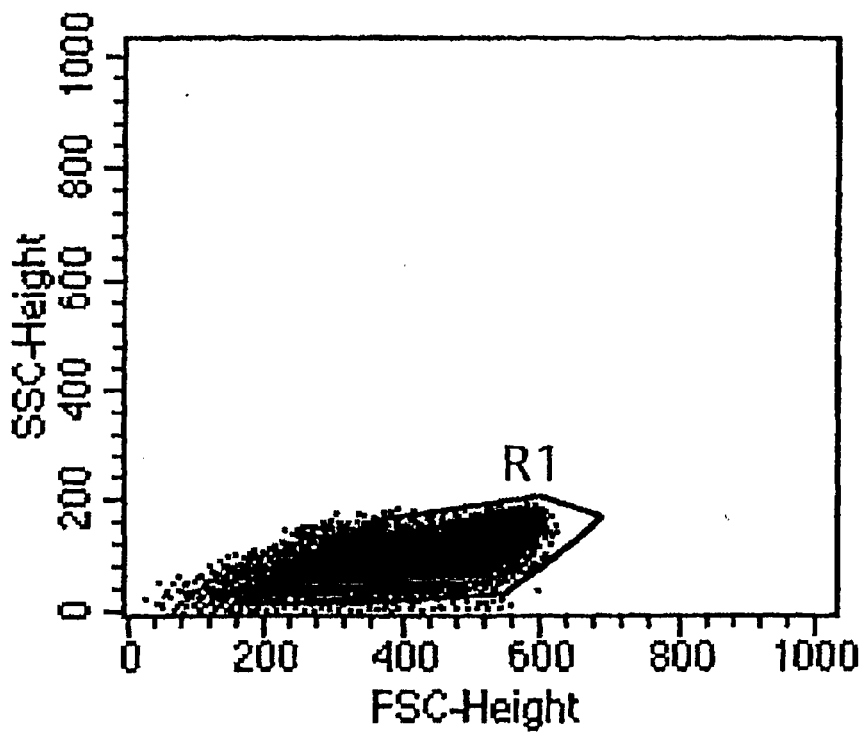
FIG. 38 is a dot plot of the results based on forward scattering light and side scattering light for the cell group where the mixing ratio of the IL-2 expression-induced cells to the IL-2 expression-uninduced cells was 20:80 when the selective separation was conducted according to flow cytometry by gating with the R1 gate of FIG. 32 and the R2 gate of FIG. 33, and the resulting cell group was again subjected to flow cytometry.
Figure 39:
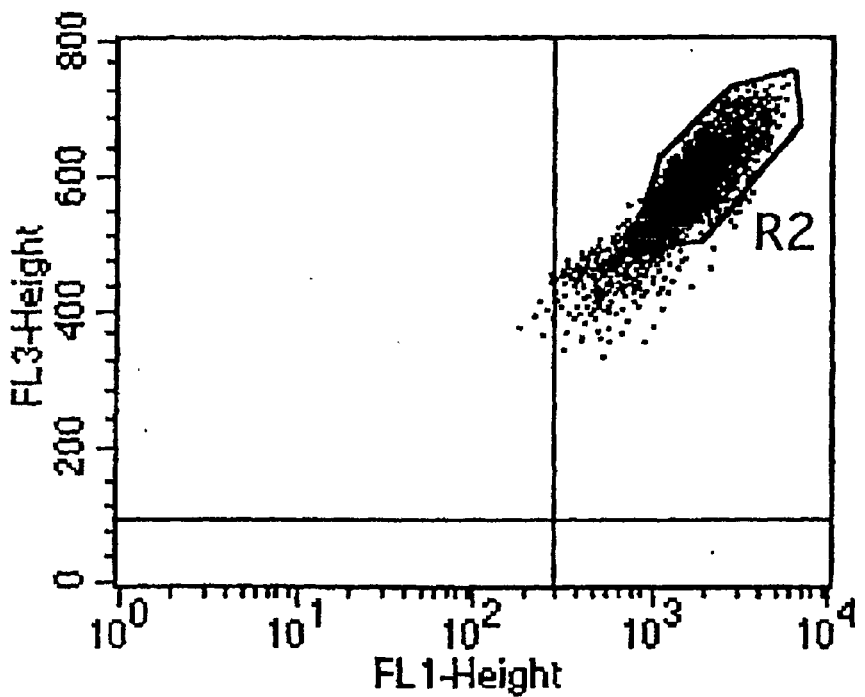
FIG. 39 is a dot plot of the results based on relative fluorescence intensity of the energy donor fluorescent dye and relative fluorescence intensity of the energy acceptor fluorescent dye due to FRET for the cell group where the mixing ratio of the IL-2 expression-induced cells to the IL-2 expression-uninduced cells was 20:80 when the selective separation was conducted according to flow cytometry by gating with the R1 gate of FIG. 32 and the R2 gate of FIG. 33, and the resulting cell group was again subjected to flow cytometry.

A cell group belonging to both R1 and R2 was collected by a cell sorting function (a cell sorter). Some of the collected cell group was applied to FACSCalibur and detected as similar dot-plots in order to confirm that the group was still fluorescently labeled as desired. The obtained dot-plots were shown in FIGS. 34–39. FIG. 34 shows a dot plot for FSC-Height and SSC-Height when the mixing ratio of IL-2 expression-induced cells to -uninduced cells was 100 to 0. FIG. 35 shows a dot plot of the cells based on FL1-Height and FL3-Height with the same mixing ratio as in FIG. 34. FIG. 36 shows a dot plot for FSC-Height and SSC-Height when the mixing ratio of IL-2 expression-induced cells to -uninduced cells was 50 to 50. FIG. 37 shows a dot plot of the cells based on FL1-Height and FL3-Height with the same mixing ratio as in FIG. 36. FIG. 38 shows a dot plot for FSC-Height and SSC-Height when the mixing ratio of IL-2 expression-induced cells to -uninduced cells was 20 to 80. FIG. 39 shows a dot plot of the cells based on FL1-Height and FL3-Height with the same mixing ratio as in FIG. 38.

The comparison of FIG. 27, FIG. 31, and FIG. 33 revealed that the proportion of dots representing the cell group belonging to R2 to the entire number of dots decreased in relation to the decrease in the mixing ratio of IL-2 expression-induced cells from 100, 50 to 20%, while the value of FL3-Height was totally background level regarding IL-2 expression-uninduced cells even when the same donor and acceptor probes were introduced to the cells (FIG. 29). As most of the sorted-out cells, selectively separated and collected cells, belonged to both R1 and R2, IL-2 expression-induced cells were found to be collected as the live cells emitting considerable FRET-fluorescence (see FIGS. 34–39).

(12) Comparison of Cell Groups Before and After Flow Cytometry by Fluorescence Microscopy Some of the cells before and after flow cytometry were transferred to glass-bottomed dishes, and ratios of fluorescing cells of D/A, A/A, and D/D of the cells in the entire visual field were examined.

Figure 40:
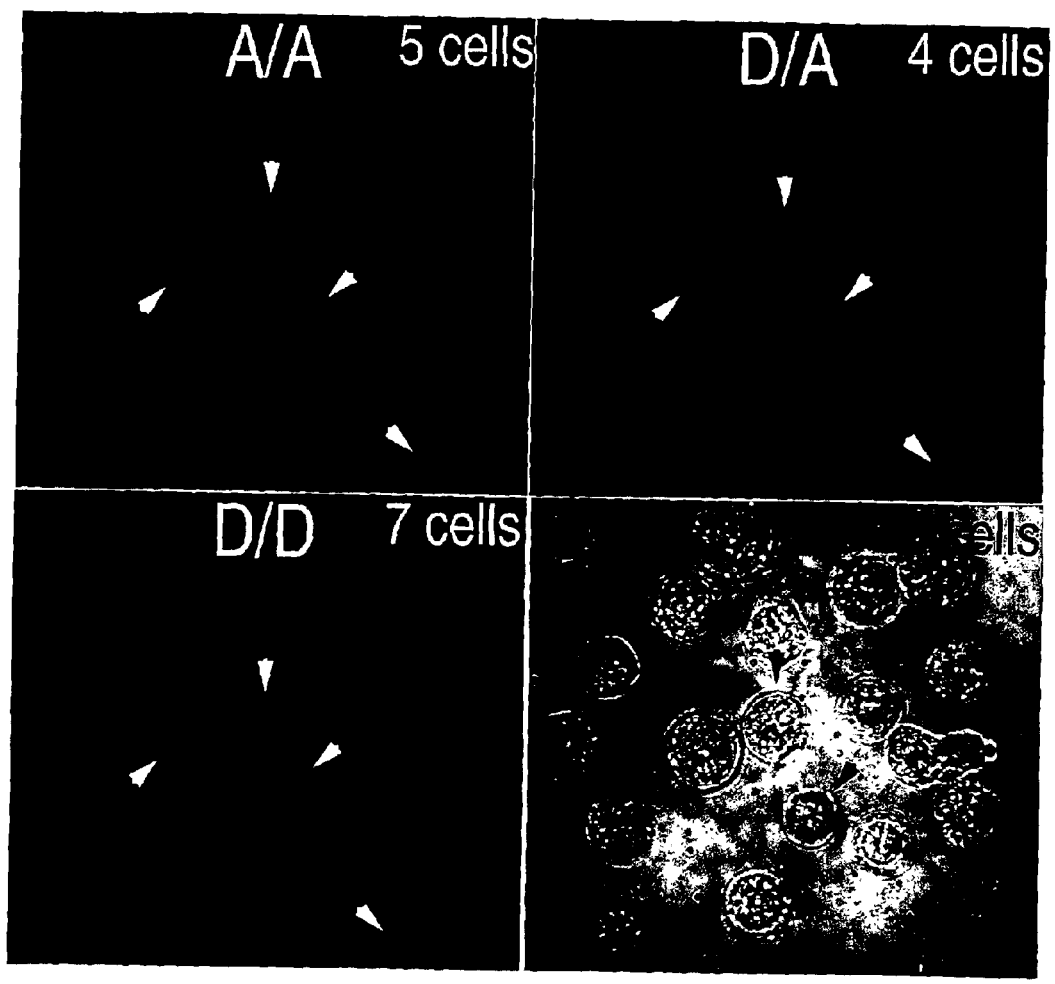
FIG. 40 is a set of micrographs showing D/A, D/D and A/A images, and the corresponding phase contrast micrograph of the cell group where the mixing ratio of the IL-2 expression-induced cells to the expression-uninduced cells in the live state was 100:0 before subjected to flow cytometry.
Figure 41:
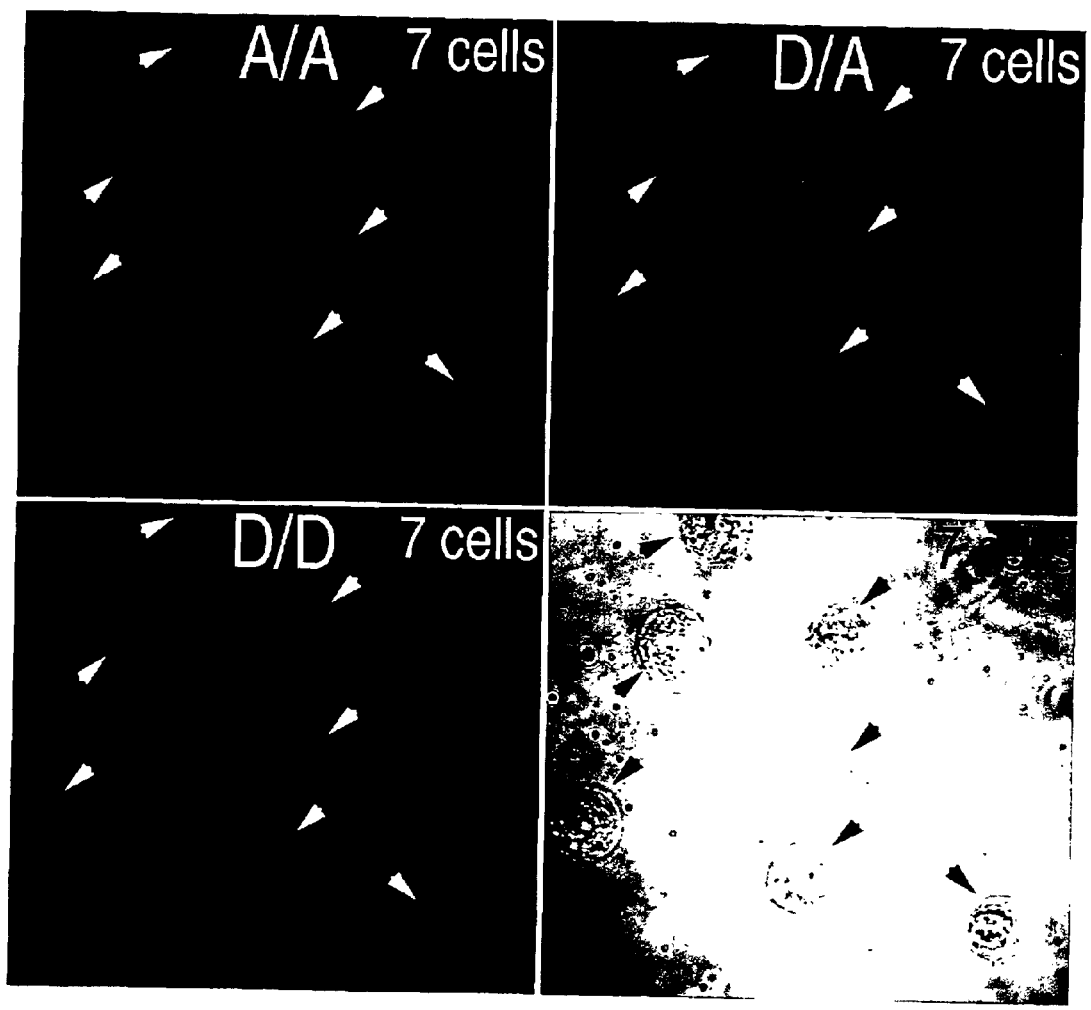
FIG. 41 is a set of micrographs showing D/A, D/D and A/A images, and the corresponding phase contrast micrograph of the cell group where the mixing ratio of the IL-2 expression-induced cells to the expression-uninduced cells in the live state was 100:0 when the selective separation was conducted according to flow cytometry by gating with the R1 gate of FIG. 26 and the R2 gate of FIG. 27.
Figure 42:
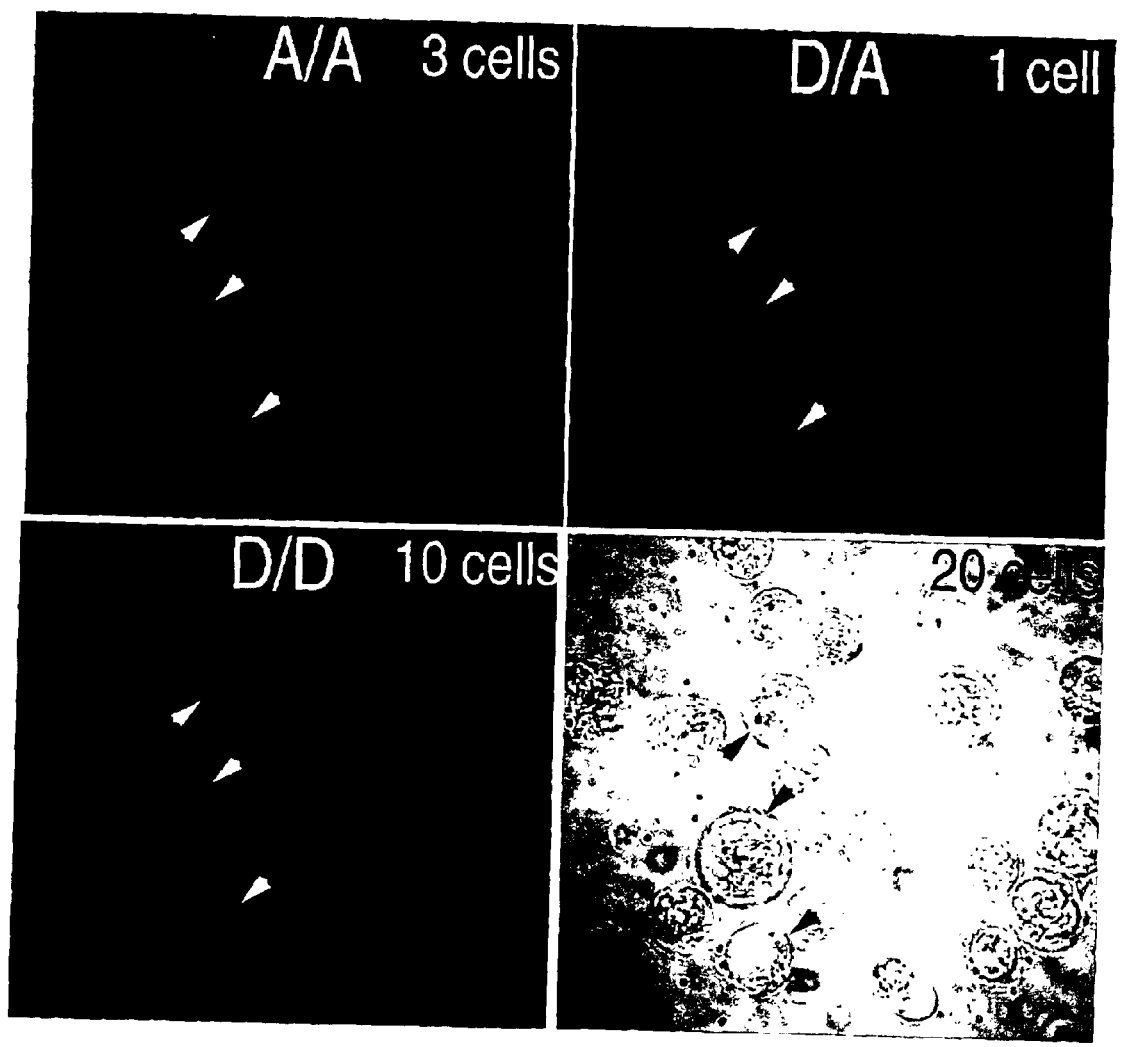
FIG. 42 is a set of micrographs showing D/A, D/D and A/A images, and the corresponding phase contrast micrograph of the cell group where the mixing ratio of the IL-2 expression-induced cells to the expression-uninduced cells in the live state was 50:50 before subjected to flow cytometry.
Figure 43:
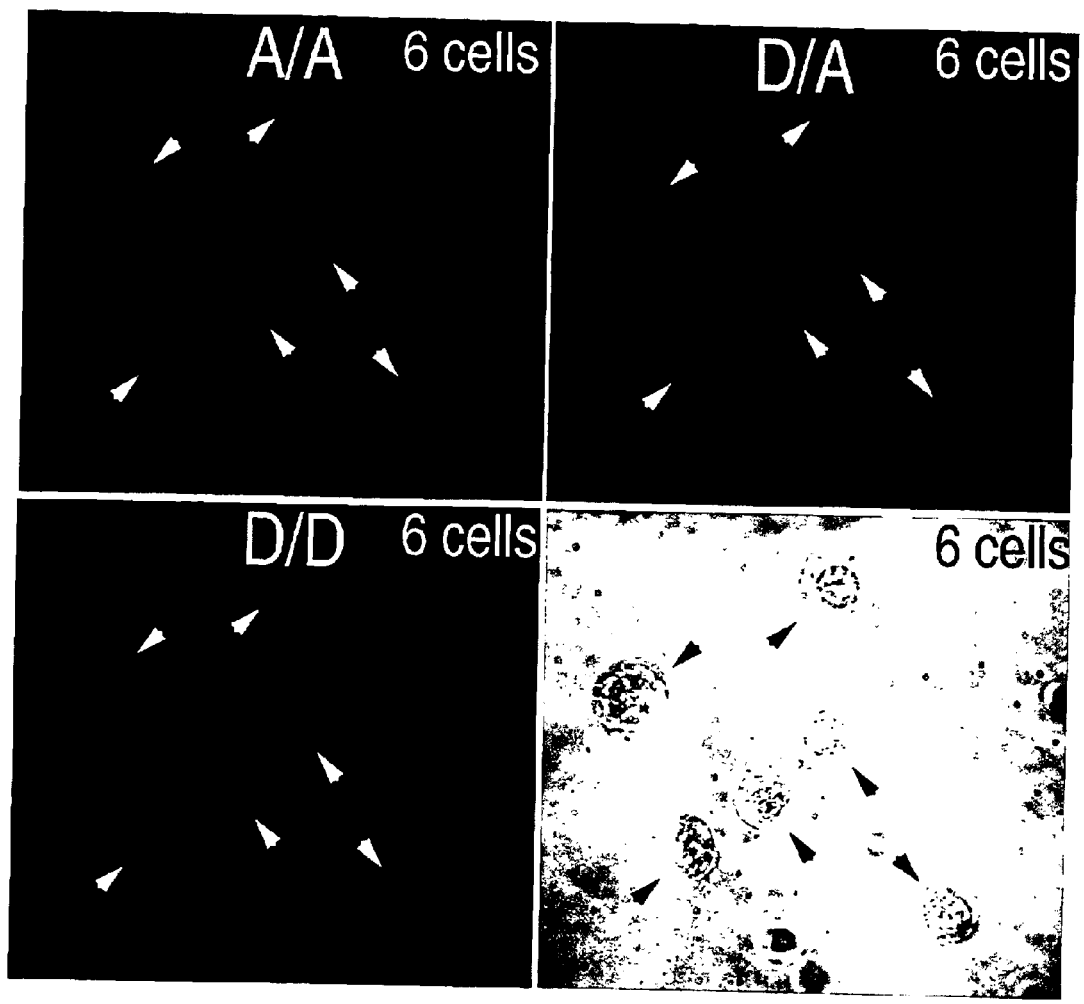
FIG. 43 is a set of micrographs showing D/A, D/D and A/A images, and the corresponding phase contrast micrograph of the cell group where the mixing ratio of the IL-2 expression-induced cells to the expression-uninduced cells in the live state was 50:50 when the selective separation was conducted according to flow cytometry by gating with the R1 gate of FIG. 40 and the R2 gate of FIG. 31.
Figure 44:
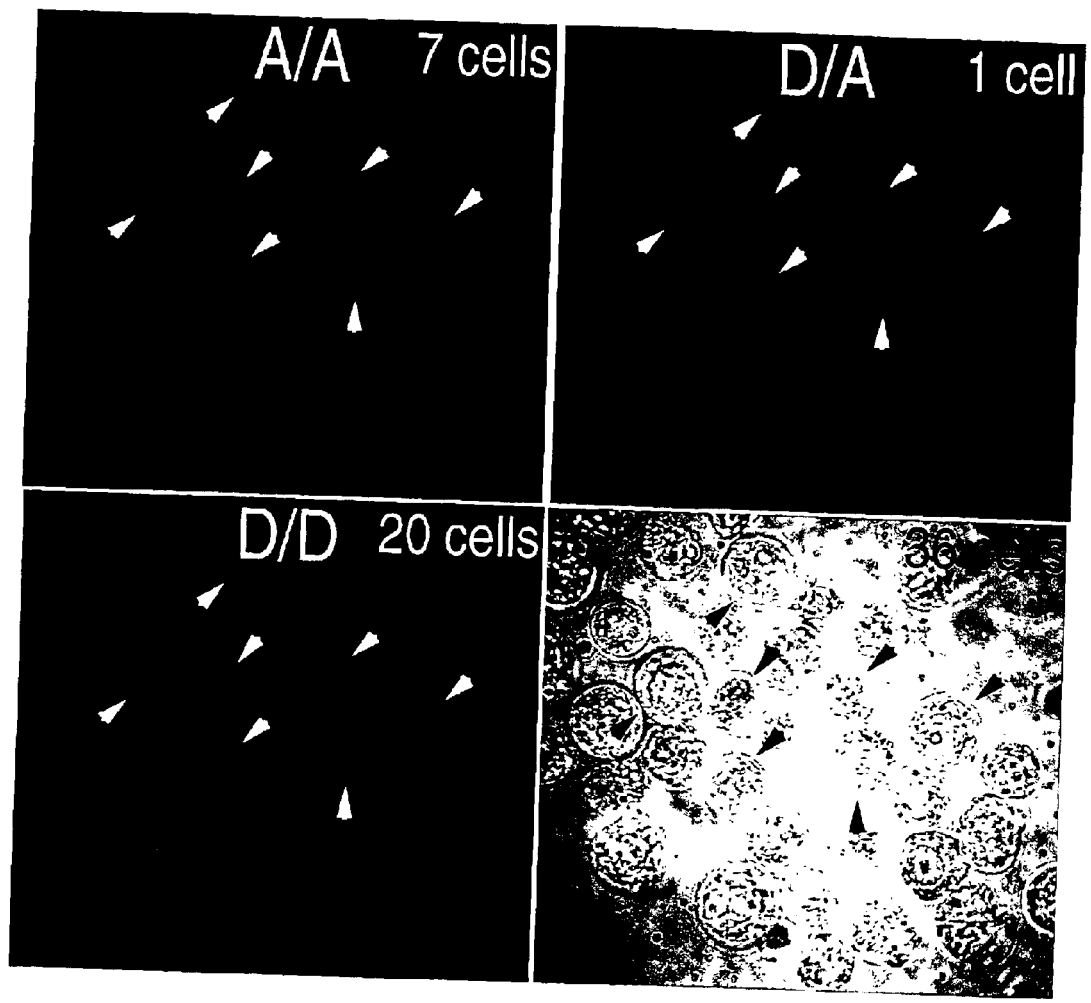
FIG. 44 is a set of micrographs showing D/A, D/D and A/A images, and the corresponding phase contrast micrograph of the cell group where the mixing ratio of the IL-2 expression-induced cells to the expression-uninduced cells in the live state was 20:80 before subjected to flow cytometry.
Figure 45:
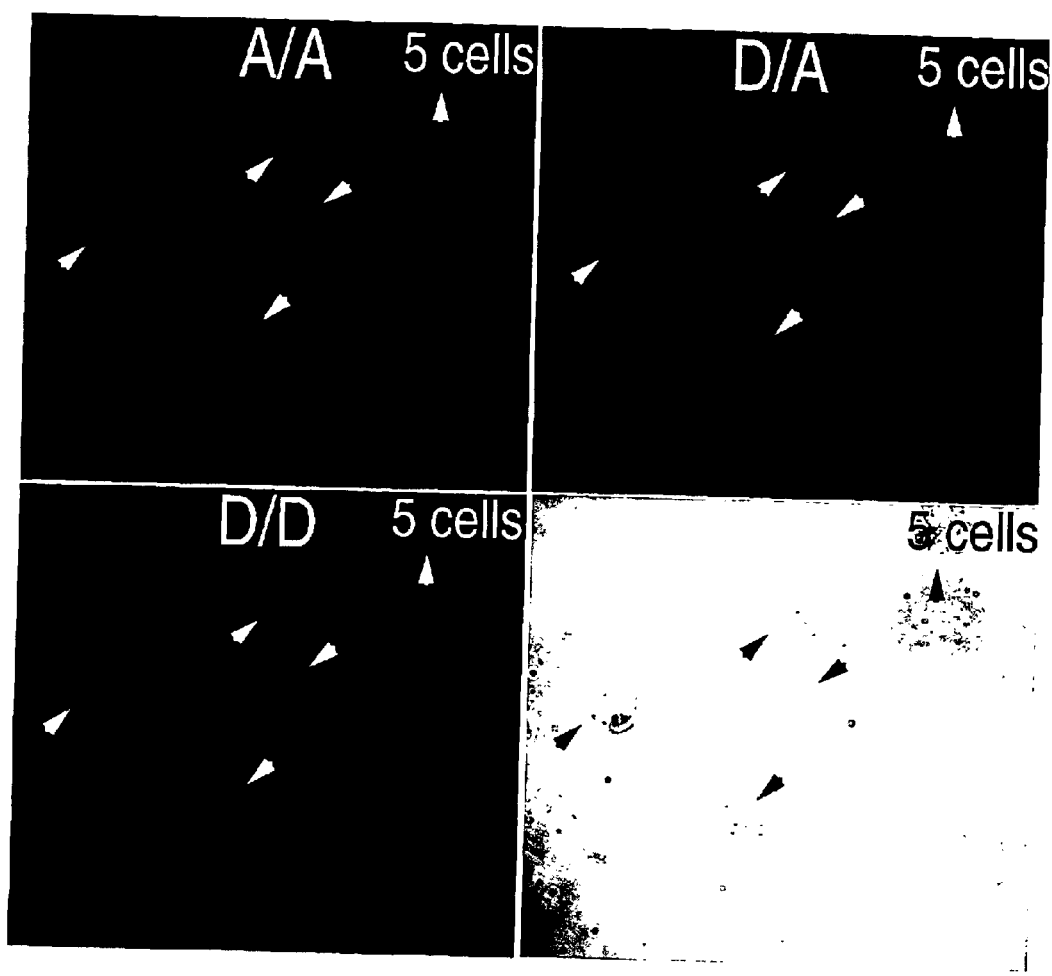
FIG. 45 is a set of micrographs showing D/A, D/D and A/A images, and the corresponding phase contrast micrograph of the cell group where the mixing ratio of the IL-2 expression-induced cells to the expression-uninduced cells in the live state was 20:80 when the selective separation was conducted according to flow cytometry by gating with the R1 gate of FIG. 32 and the R2 gate of FIG. 33.

The results were shown in FIGS. 40–46. FIGS. 40, 42, 44, and 46 show images of the cells before flow cytometry; fluorescence images of acceptor dyes based on FRET representing hybrid formation among IL-2 mRNA, donor probes and acceptor probes (D/A image), fluorescence images of donor dyes by the donor-excitation representing the presence of donor probes in the cells (D/D image), fluorescence images of acceptor dyes by the acceptor-excitation representing the presence of acceptor probes in the cells (A/A image), and the corresponding phase contrast images. FIGS. 41, 43 and 45 show images of the cells after flow cytometry, the cells selectively collected by the cell sorting function. The A/A, D/A, and D/D fluorescence images and the corresponding phase contrast images are shown in these figures as in FIGS. 40, 42, 44 and 46. In FIGS. 40–46, arrows indicating some cells are shown to align the positions of cells between the fluorescence images and the phase contrast images.

Cells in FIGS. 40 and 41 were the mixture of IL-2 expression-induced and -uninduced live cells with the ratio of 100 to 0; cells in FIGS. 42 and 43 were those with the ratio of 50 to 50. Cell groups in FIGS. 34 and 35 were those with the ratio of 20 to 80; and cell groups in FIG. 46 were those with the ratio of 0 to 100.

In FIG. 40, the description of 20 cells in the phase contrast micrograph means that there were 20 cells in the entire visual field. The descriptions of 5 cells, 4 cells and 7 cells in A/A, D/A and D/D images represent that the numbers of the cells emitting A/A-, D/A-, and D/D-fluorescence were 5, 4, and 7, respectively.

Figure 46:
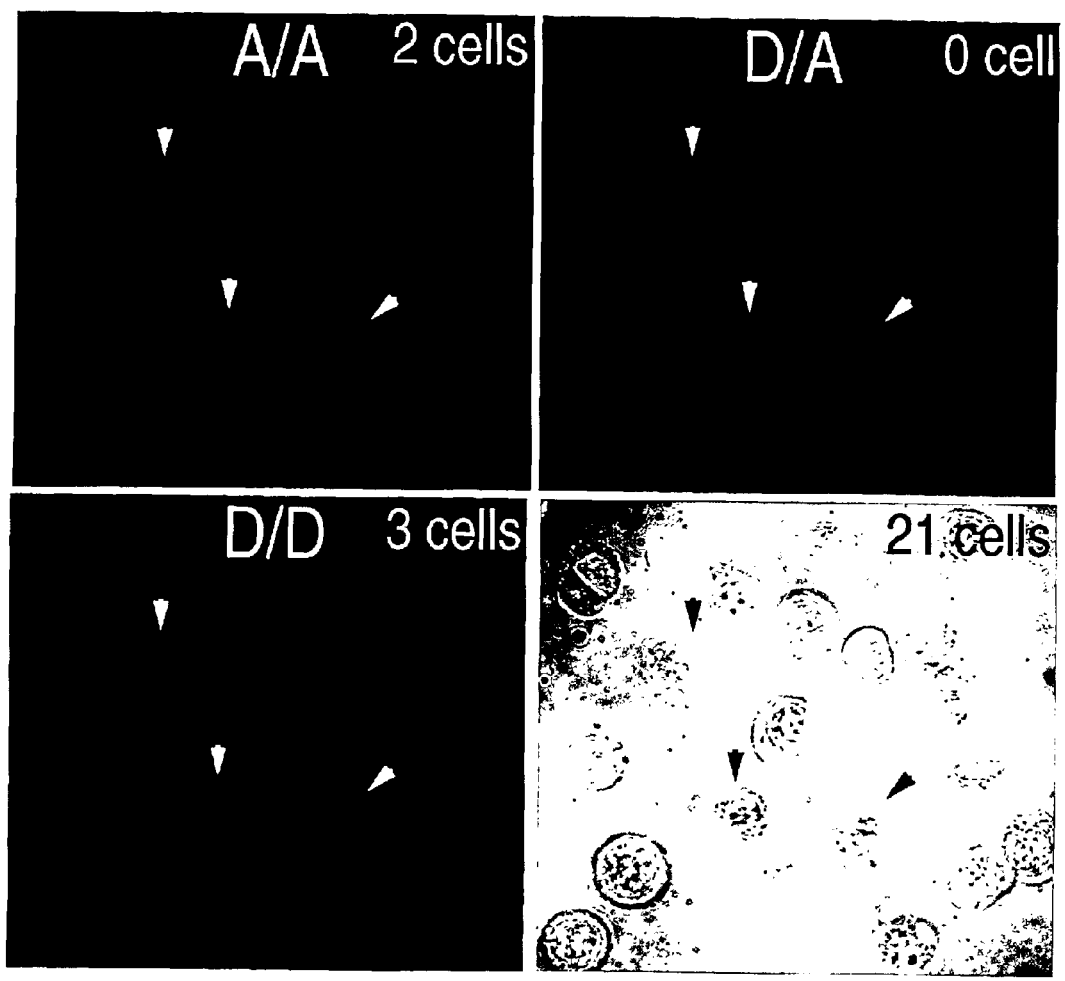
FIG. 46 is a set of micrographs showing D/A, D/D and A/A images, and the corresponding phase contrast micrograph of the cell group where the mixing ratio of the IL-2 expression-induced cells to the expression-uninduced cells in the live state was 0:100 before subjected to flow cytometry.

In FIG. 42, the descriptions of 20 cells, 3 cells, 1 cell and 10 cells mean that the number of the cells in the entire visual field was 20 and the numbers of cells emitting A/A-, D/A-, and D/D-fluorescence were 3, 1, and 10 respectively. In FIG. 44, the descriptions of 36 cells, 7 cells, 1 cell and 20 cells mean that the number of the cells in the entire visual field was 36 and the numbers of cells emitting A/A-, D/A-, and D/D-fluorescence were 7, 1, and 20, respectively. In FIG. 46 where IL-2 expression-uninduced cells are contained, the descriptions of 21 cells, 2 cells, 0 cell and 3 cells mean that the number of the cells in the entire field was 21 and the numbers of cells emitting A/A-, D/A-, and D/D-fluorescence were 2, 0, and 3 respectively.

Thus, as the ratio of IL-2 expression-induced cells was decreased from 100, 50, to 20%, it was found that the ratio of D/A-fluorescent cells possessing fluorescently labeled IL-2 mRNA to the cells in the entire visual field decreased.

FIG. 41 shows fluorescence images of the cells selectively separated from the mixture of IL-2 expression-induced and -uninduced live cells with the ratio of 100 to 0. The description of 7 cells in the phase contrast micrograph means that 7 cells exist in the entire visual fields. The descriptions of 7 cells, 7 cells, and 7 cells in the A/A, D/A and D/D images represent that all 7 cells in the field were emitting A/A-, D/A- and D/D-fluorescence.

In FIG. 43, the descriptions of 6 cells in the phase contrast image and in all the A/A, D/A and D/D images represent that the number of the cells in the entire field was 6 and that all the cells were emitting A/A-, D/A-, and D/D-fluorescence. Similarly in FIG. 45, all the descriptions of 5 cells in the phase contrast image and in all the A/A, D/A and D/D images represent the number of the cells in the entire field was 5 and that all the cells were emitting A/A-, D/A-, and D/D-fluorescence.

The comparison between FIGS. 40 and 41, between FIGS. 42 and 43, and between FIGS. 44 and 45 revealed that only the cells in which IL-2 mRNA was fluorescently labeled could be selectively separated by the cell sorting function of flow cytometry (a cell sorter).

(13) Comparison Between the Cells Before and After Flow Cytometry by In Situ Hybridization Some of the cells before and after flow cytometry were transferred to a glass-bottomed dish, and fixed with 4% paraformaldehyde/PBS (pH7.4) at room temperature for 30 minutes. The ratio of cells carrying IL-2 mRNA (IL-2 mRNA (+)) in the entire visual field was determined by fluorescent in situ Hybridization. First, in this FISH, in order to prevent higher background caused by RNA probes remaining in the cell after the wash-out procedure, IL-2 RNA probes, which were obtained by the fragmentation of a full-length anti-sense IL-2 RNA synthesized according to the method in (7) (c), were used for hybridization experiments.

A full-length anti-sense IL-2 RNA, 10 $\mu$g, were dissolved in 100 $\mu$l of alkaline solution (42 mM NaHCO$_3$, 63 mM Na$_2$CO$_3$, 5 mM DTT), incubated at 60° C. for 10–15 minutes. Then, 10 $\mu$l of 3M sodium acetate and 350 $\mu$l of ethanol were added to precipitate the RNA probes. After allowing to stand at −20° C. for 30 minutes, they were and centrifuged at 16 krpm for 20 minutes. The obtained precipitates were washed with 70% ethanol and dried. The precipitates were dissolved in 50 $\mu$l of RNase-free sterile distilled water to prepare an alkaline denatured RNA probe solution for IL-2 RNA.

The cells fixed at the bottom of the dish were washed with PBS(-) three times and treated with 0.1% Triton X-100/PBS solution at room temperature for 5 minutes to permeabilize the cells, and the permeabilized cells were washed with PBS(-) three times and treated with 0.2N HCl at room temperature for 10 minutes. After washing the monolayer cells with PBS(-), they were incubated with 1 $\mu$g/ml of proteinase K/PBS solution for 5 minutes at 37° C. After the monolayer cells were washed with PBS(-), they was fixed again with 4% of paraformaldehyde/PBS (pH 7.4) for 30 minutes. The fixed cells were washed twice with 2 mg/ml of glycine/PBS for 15 minutes, and treated with 50% deionized formamide/2×SSC solution (solution A, described hereunder) for 30 minutes; the hybridization solution (50% deionized formamide, 5× denhardt, 2×SSC, alkaline denatured probes for IL-2 RNA (1 $\mu$g/ml)) was prepared, denatured at 90° C. for 10 minutes, and then the monolayer cells were ice-cooled. Adding 100 $\mu$l of the hybridization solution to the cells, they were incubated at 45° C. overnight.

The monolayer cells after the hybridization were washed twice with solution A for 5 minutes at 45° C., then washed with solution B (10M Tris.HCl (pH8.5),500 mM NaCl) for 5 minutes, and treated with 20 $\mu$g/ml of RNase A/solution B (pretreated at 90° C. for 10 minutes) at 37° C. for 20 minutes. They were washed with solutions A at 45° C. for 30 minutes and C (50% of deionized formamide/1×SSC) at 45° C. for 30 minutes and with solution C at room temperature for 20 minutes. After washing with Buffer 1 [100 mM maleic acid, 150 mM NaCl (pH7.5)] twice for 5 minute, they were treated with Buffer 2 [1% Blocking Reagent (Boehringer Mannheim Inc.) in Buffer 1] at room temperature for 20 minutes.

After the monolayer cells were washed with Buffer 1 twice, FITC-labeled anti-DIG antibodies (Fab, diluted with Buffer 2 by 100 times, protein level: about 1 μg/ml) was added, incubated for at least 30 minutes, washed with PBS(-) three times. The cells were observed under a fluorescence microscope; and the ratio of cells carrying IL-2 mRNA to the total cells in the visual field was determined.

Figure 47:
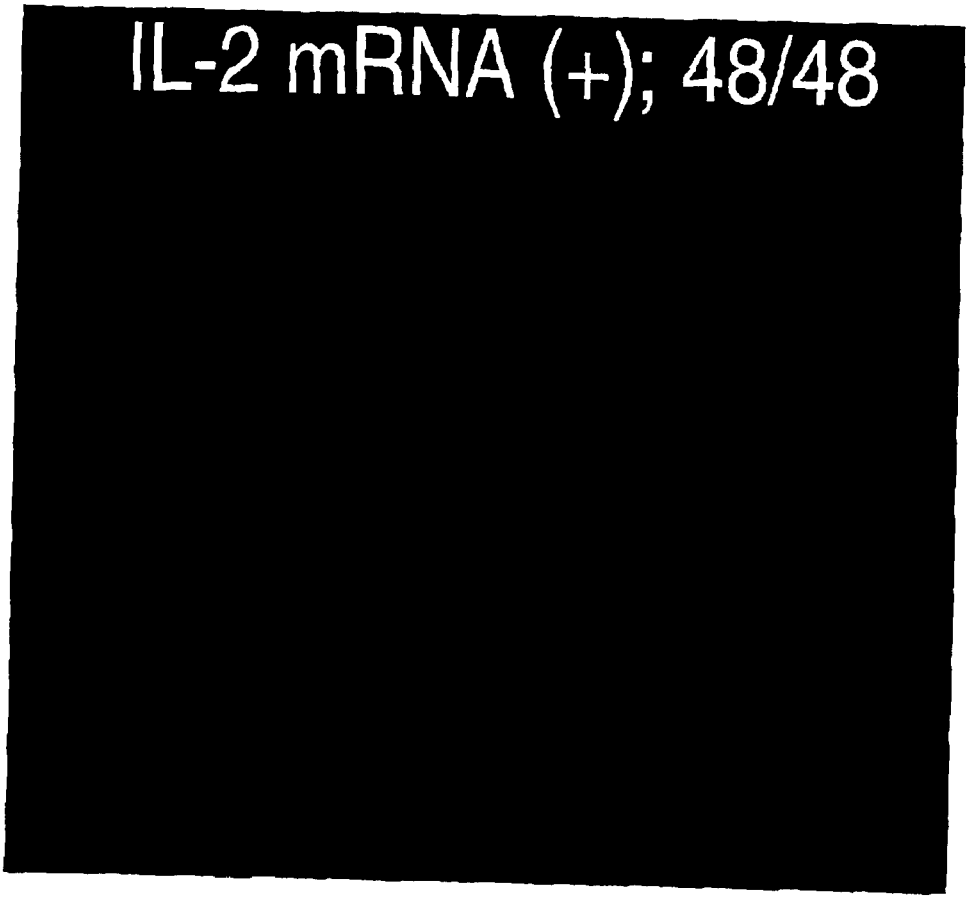
FIG. 47 is a fluorescence micrograph obtained when the cell group obtained by mixing IL-2 expression-induced cells and IL-2 expression-uninduced cells at the ratio of 100:0 before flow cytometry thereof was fixed to a glass-bottomed dish, hybrids were formed between the cellular IL-2 mRNA in the fixed state and RNA probe for IL-2 RNA s, and the hybrids were fluorescently detected.
Figure 48:
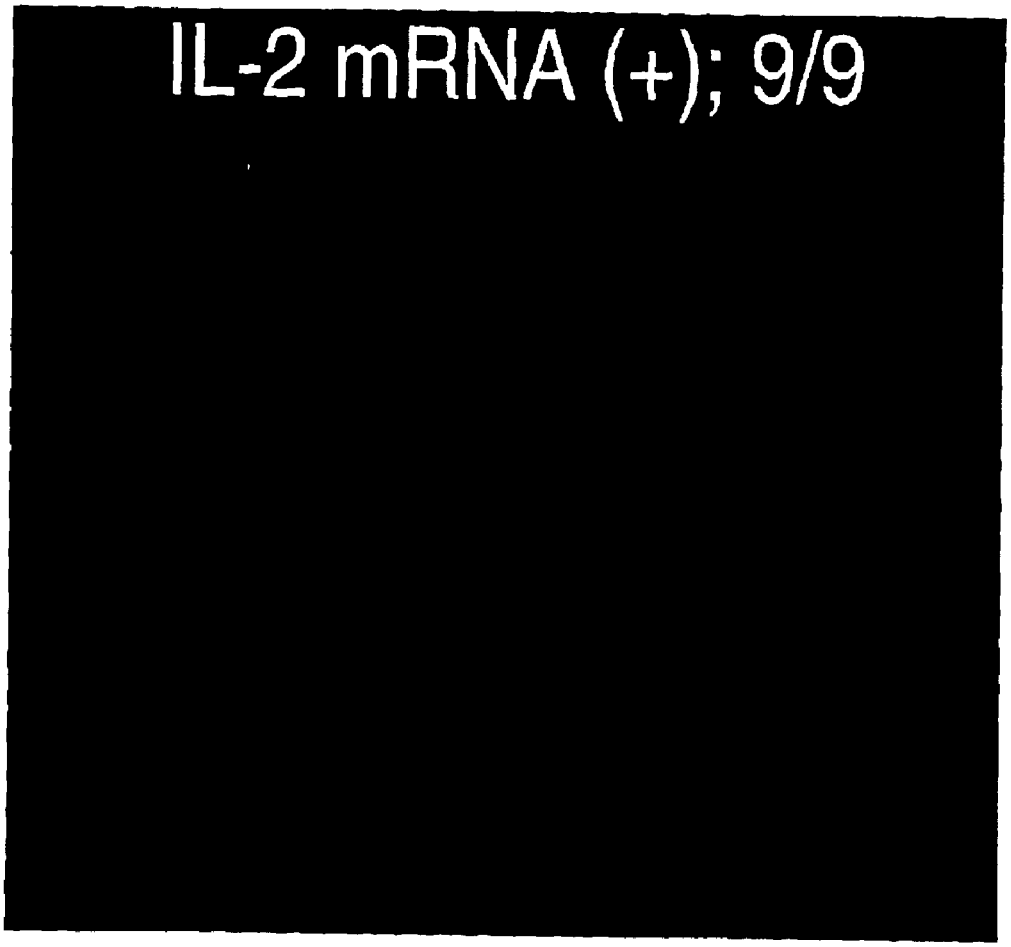
FIG. 48 is a fluorescence micrograph obtained when the cell group obtained by mixing IL-2 expression-induced cells and IL-2 expression-uninduced cells at the ratio of 100:0 was subjected to selective separation according to flow cytometry by gating with the R1 gate of FIG. 26 and the R2 gate of FIG. 27, the resulting cell group was fixed to a glass-bottomed dish, hybrids were formed between the cellular IL-2 mRNA in the fixed state and RNA probe for IL-2 RNA s, and the hybrids were fluorescently detected.
Figure 49:
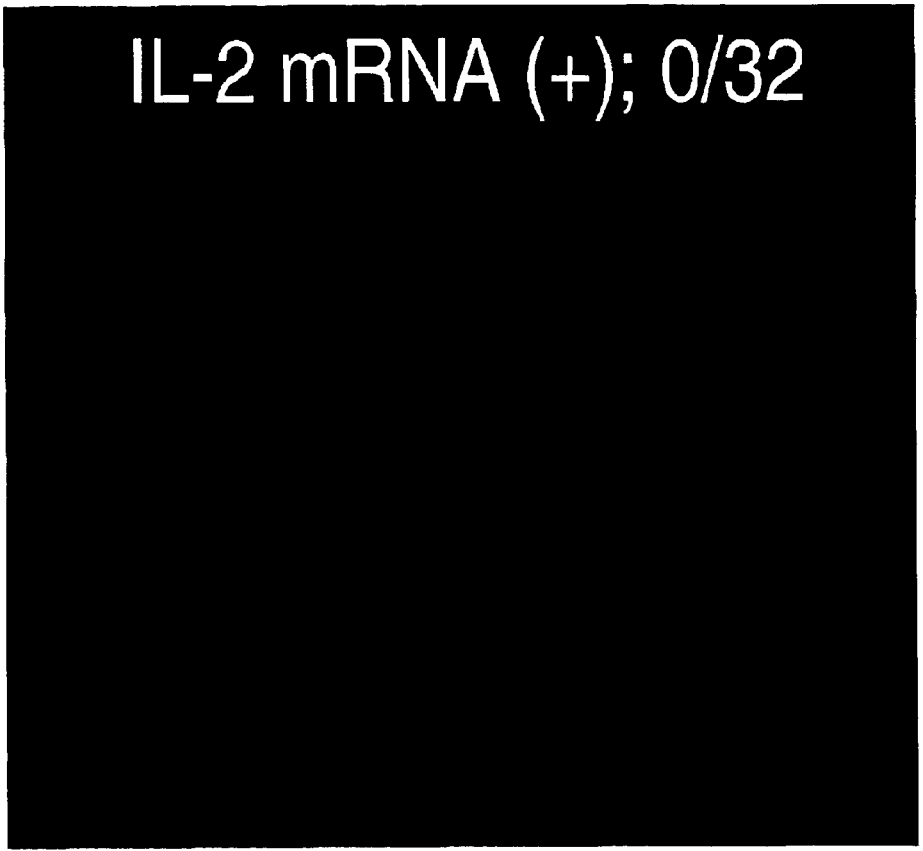
FIG. 49 is a fluorescence micrograph obtained when the cell group obtained by mixing IL-2 expression-induced cells and IL-2 expression-uninduced cells at the ratio of 0:100 before flow cytometry thereof was fixed to a glass-bottomed dish, hybrids were formed between the cellular IL-2 mRNA in the fixed state and RNA probe for IL-2 RNA s, and the hybrids were fluorescently detected.
Figure 50:
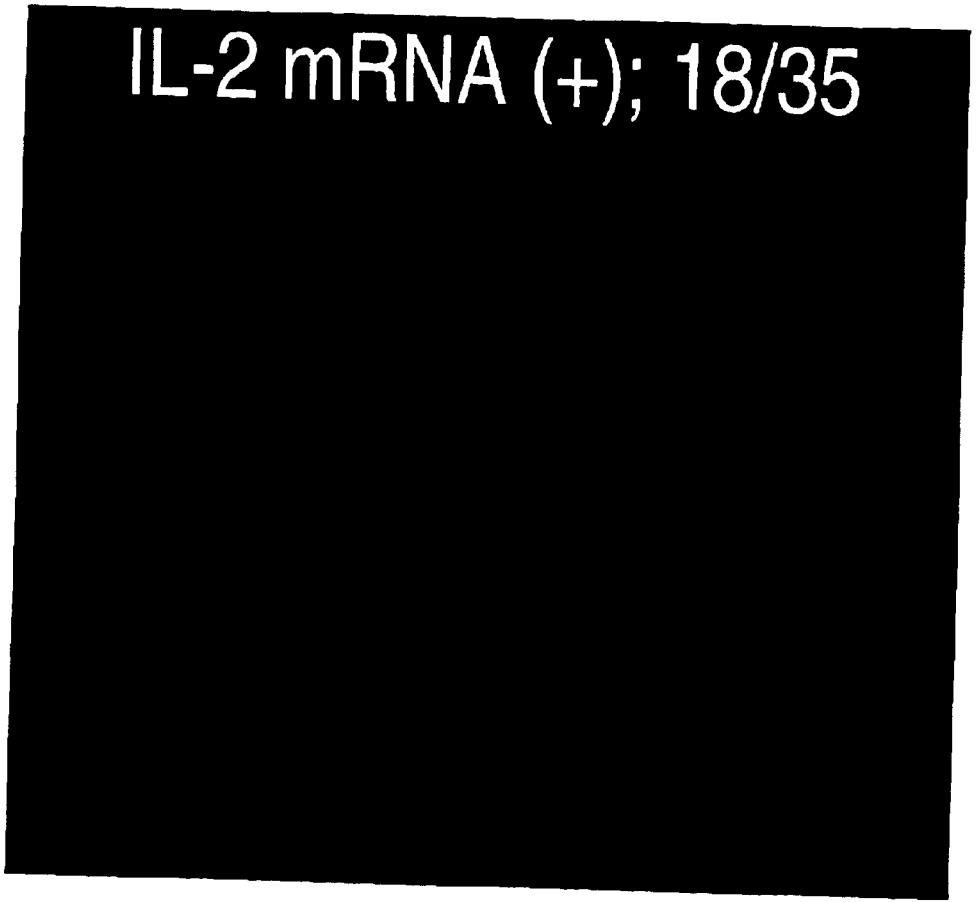
FIG. 50 is a fluorescence micrograph obtained when the cell group obtained by mixing IL-2 expression-induced cells and IL-2 expression-uninduced cells at the ratio of 50:50 before flow cytometry thereof was fixed to a glass-bottomed dish, hybrids were formed between the cellular IL-2 mRNA in the fixed state and RNA probe for IL-2 RNA s, and the hybrids were fluorescently detected.
Figure 51:
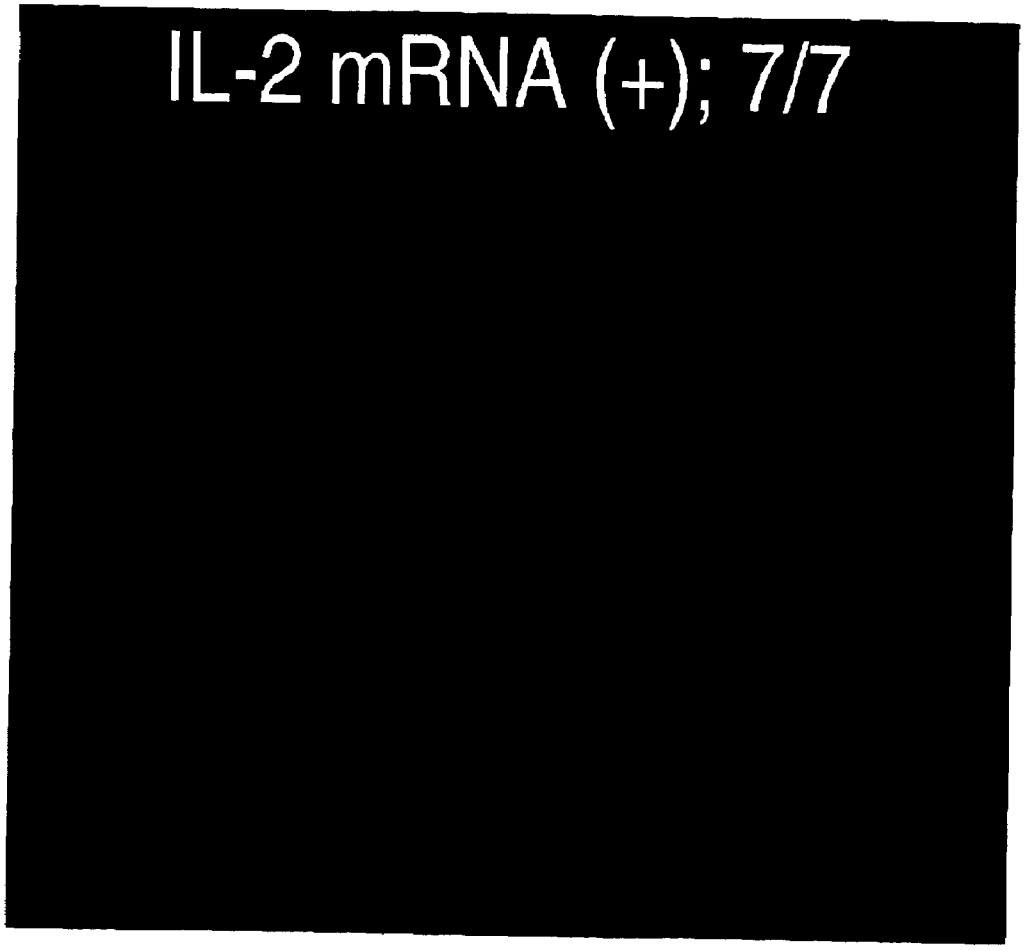
FIG. 51 is a fluorescence micrograph obtained when the cell group obtained by mixing IL-2 expression-induced cells and IL-2 expression-uninduced cells at the ratio of 50:50 was subjected to selective separation according to flow cytometry by gating with the R1 gate of FIG. 30 and the R2 gate of FIG. 31, the resulting cell group was fixed to a glass-bottomed dish, hybrids were formed between the cellular IL-2 mRNA in the fixed state and RNA probe for IL-2 RNA s, and the hybrids were fluorescently detected.
Figure 52:
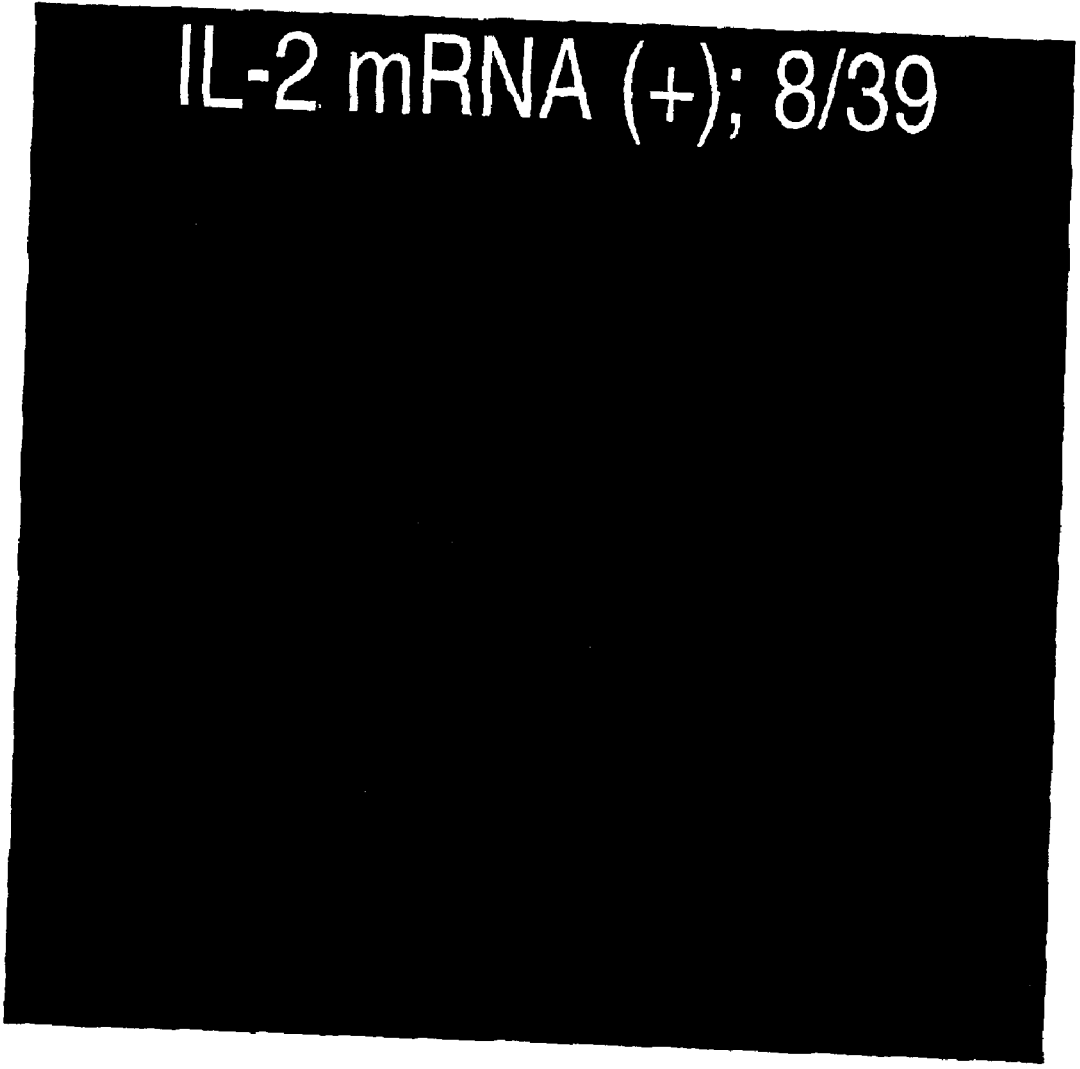
FIG. 52 is a fluorescence micrograph obtained when the cell group obtained by mixing IL-2 expression-induced cells and IL-2 expression-uninduced cells at the ratio of 20:80 before flow cytometry thereof was fixed to a glass-bottomed dish, hybrids were formed between the cellular IL-2 mRNA in the fixed state and RNA probe for IL-2 RNA s, and the hybrids were fluorescently detected.
Figure 53:
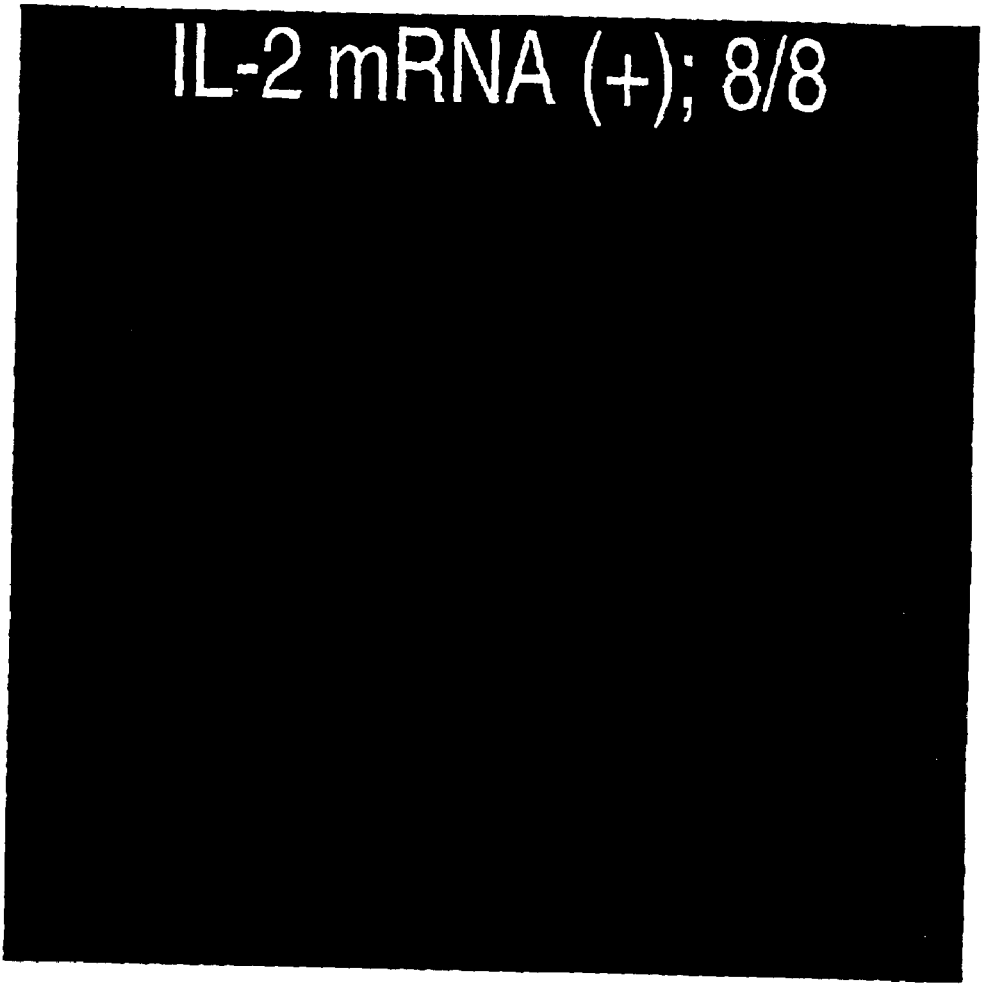
FIG. 53 is a fluorescence micrograph obtained when the cell group obtained by mixing IL-2 expression-induced cells and IL-2 expression-uninduced cells at the ratio of 20:80 was subjected to selective separation according to flow cytometry by gating with the R1 gate of FIG. 32 and the R2 gate of FIG. 33, the resulting cell group was fixed to a glass-bottomed dish, hybrids were then formed between the cellular IL-2 mRNA in the fixed state and RNA probe for IL-2 RNA s, and the hybrids were fluorescently detected.
Figure 54:
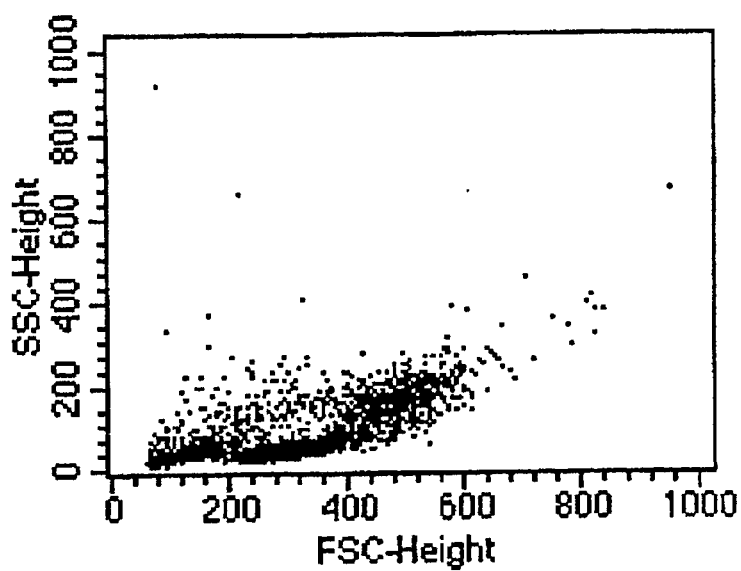
FIG. 54 is a dot plot of the results based on forward scattering light (FSC) and side scattering light (SSC) for lymphocytes separated from human peripheral blood when subjected to flow cytometry.
Figure 55:
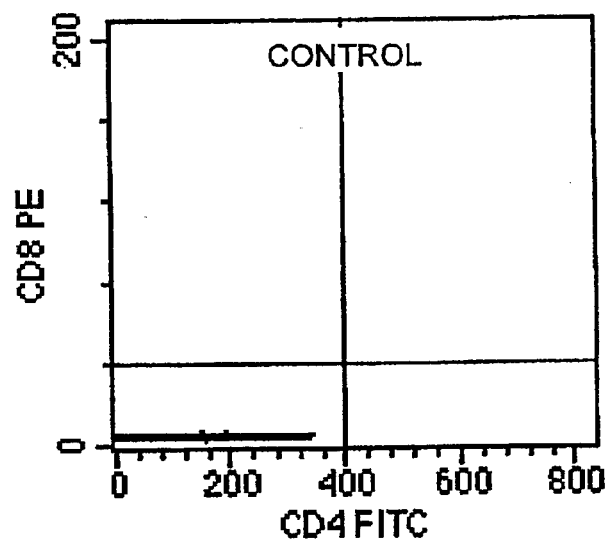
FIG. 55 is a dot plot of the results of lymphocytes separated from human peripheral blood that were fluorescently labeled on cell surfaces thereof with a control antibody when subjected to flow cytometry.

FIGS. 47 and 48 show fluorescence micrographs when the mixing ratio of IL-2 expression-induced cells to -uninduced cells was 100 to 0. FIG. 47 shows micrographs before flow cytometry. FIG. 48 shows micrographs after flow cytometry. FIG. 49 shows fluorescence micrographs before flow cytometry when the mixing ratio of IL-2 expression-induced cells to -uninduced cells was 0 to 100. FIGS. 50 and 51 show fluorescence micrographs when the mixing ratio of IL-2 expression-induced cells to -uninduced cells was 50 to 50. FIG. 50 shows micrographs before flow cytometry and FIG. 51 shows those after flow cytometry. FIGS. 52 and 53 show fluorescence micrographs when the mixing ratio of IL-2 expression-induced cells to -uninduced uninduced cell was 20 to 80. FIG. 52 shows fluorescence micrographs before flow cytometer, and FIG. 53 shows those after flow cytometry.

The figures in the micrographs represent the numbers of fluorescing cells per the number of total cells in the entire visual field. In FIG. 47, "48/48" represents that all of the 48 cells were fluorescing cells in the image, suggesting that all the cells were IL-2 mRNA carrying cells. On the contrary, "0/32" in FIG. 49 represents that there were no IL-2 mRNA carrying cells out of 32 cells. In FIG. 50, "18/35" represents that 18 cells possess IL-2 mRNA out of 35 cells. In FIG. 52, "8/39" represents that 8 cells possess IL-2 mRNA out of 39 cells. These results are well consistent with the fact that IL-2 expression-induced and -uninduced cells were mixed with the ratios of 50 to 50 in FIG. 50 and 20 to 80 in FIG. 52. On the other hand, the figures in FIG. 48, FIG. 51, and FIG. 53 were %, 7/7, and 8/8, respectively, suggesting that IL-2 mRNA carrying cells were condensed from 20–50% to 100% throughout flow cytometry.

(14) Separation Method Based on Fluorescence Intensities of Live Cells Expressing Specific Genes Table 8 is a summarized result of (11)–(13) to show the effect of this separation method utilizing the differenciated intensities based on the fluorescent labeling of IL-2 mRNA. The cells carrying IL-2 mRNA which were condensed from 20–50% to 100% by the separation method utilizing the difference in fluorescence intensities. That is, all the live cells carrying IL-2 mRNA were selectively separated from the live cell group containing, IL-2 mRNA carrying cells.

TABLE 8

| Mixing Ratios IL-2 expression | | Flow Cytometry | | | |
|---|---|---|---|---|---|
| | | Before | | After | |
| | | FRET (D/A) Positive | Cells carrying IL-2 mRNA | FRET (D/A) Positive | Cells carrying IL-2 mRNA |
| Induced | uninduced | Cells (%) | (%) | Cells (%) | (%) |
| 100 | 0 | 20 | 100 | 100 | 100 |
| 0 | 100 | 0 | 0 | — | — |
| 50 | 50 | 5 | 51.4 | 100 | 100 |
| 20 | 80 | 2.8 | 20.5 | 100 | 100 |

(15) Separation of Lymphocytes From Human Peripheral Blood

After sampling 200 ml of blood from a healthy adult and adding heparin thereto at a final concentration of 10 U/ml, it was mixed with a two-fold volume of 3% dextrin in PBS (phosphate buffered saline) in a 50 ml centrifugation tube (Falcon 2070), and the mixture was allowed to stand at room temperature for 15 minutes to precipitate erythrocytes. 21.5 ml of the supernatant was gently superposed onto a 15 ml of Ficoll pack (Pharmacia) and subjected to centrifugation at 490×g (1,600 rpm) for 30 minutes. The lymphocyte layer observed as white suspended matter in the supernatant was collected with a pipette. After mixing the lymphocyte layer with a three-fold volume of HBSS (Hanks' Balanced Salt Solution, GIBCO BRL) in a 50 ml centrifugation tube (Falcon 2070) and centrifuging at 1,200 rpm for 10 minutes, the lymphocyte precipitate was washed twice with 30 ml of PBS(-) and suspended to a cell density of about $2.5 \times 10^7$ cells/ml.

(16) Separation and Fluorescent Antibody Staining of Helper T Cells (CD4+ Cells) From Peripheral Blood Lymphocytes Separation of CD4+ cells from peripheral blood lymphocytes was performed using Human CD4+ cell Recovery Column Kit (CEDARLANE Laboratories, Ltd.) was used for separation of the CD4+ cells, by a separation procedure according to the protocol provided with the kit.

A CD4+ cell separating column (CEDARLANE) was set in a column stand and the glass beads in the column were equilibrated with 15 ml of PBS(-), with only a slight amount of the PBS(-) remained above the beads. To coat these beads with goat anti-human IgG (H+L) and goat anti-mouse IgG (H+L), the powder of Column Reagent (CEDARLANE) was dissolved in 1–1.5 ml of PBS(-), and applied to the column and allowed to flow till only a slight amount remained above the beads, and this was allowed to stand at room temperature for 1–8 hours.

To neutralize CD8+ cells in the cell sample with CD8-specific antibodies (mouse anti-human CD8), the powder of Cell Reagent (CEDARLANE) was dissolved in 1.5 ml of PBS(-), and the total amount of this Cell Reagent solution was mixed with 3.5–4.5 ml of the lymphocyte suspension prepared in (15) above in a 50 ml centrifugation tube (Falcon 2070) and incubated on ice for at least 30 minutes. After adding 15 ml of PBS(-) to the lymphocyte suspension, it was centrifuging at 4° C., 200×g (approximately 1,200 rpm) for 5–10 minutes, the supernatant was removed by pipetting.

The resulting cell precipitate was washed again with 15 ml of PBS(-) and suspended to a cell density of about $5 \times 10^7$ cells/ml PBS (-). The beads equilibrated with PBS(-) in a column as described above were washed with 20 ml of PBS(-) adjusting the flow rate to 6–8 drops/min (1 drop/8 sec), and then the lymphocyte suspension was poured down over the column beads, the eluate was collected in a 15 ml tube (Falcon), and the pouring was stopped when a slight amount of the suspension remained above the beads. PBS(-) was further poured onto the beads, and 10–15 ml of eluate was collected. The obtained eluates were centrifuged at 4° C. at 1,200 rpm for 10 minutes, the supernatant was removed by pipetting, and the obtained precipitate was suspended to a cell density of $1.0 \times 10^7$ cells/ml in PBS(-) containing 10% fetal bovine serum (FBS).

Figure 56:
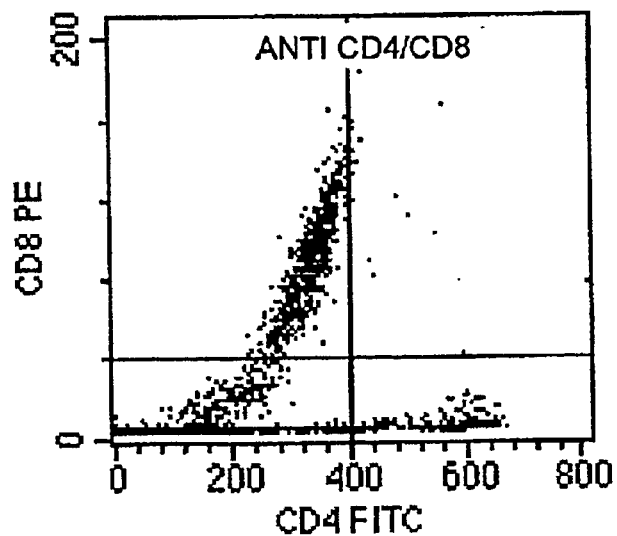
FIG. 56 is a dot plot of the results of lymphocytes separated from human peripheral blood that were fluorescently labeled at CD4 (CD4 FITC) and CD8 (CD8 PE) on cell surfaces thereof when subjected to flow cytometry.
Figure 57:
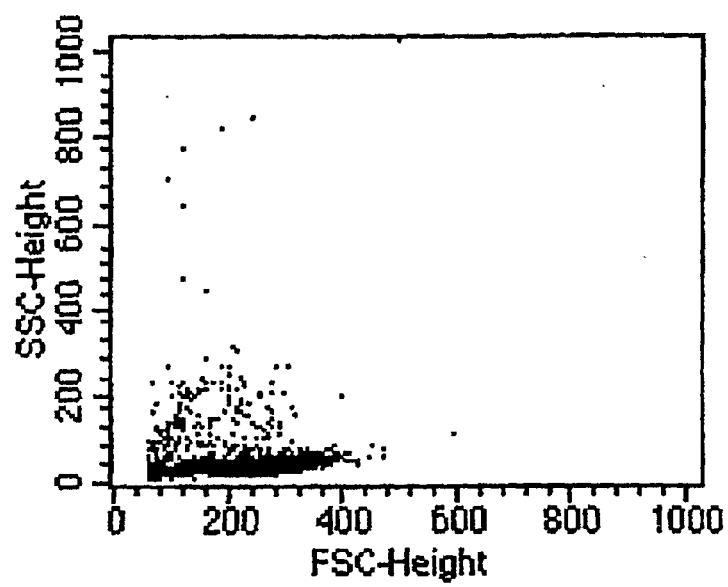
FIG. 57 is a dot plot of the results based on forward scattering light (FSC) and side scattering light (SSC) for CD4+cells separated from human peripheral blood with a CD4+ cell separating column when subjected to flow cytometry.
Figure 58:
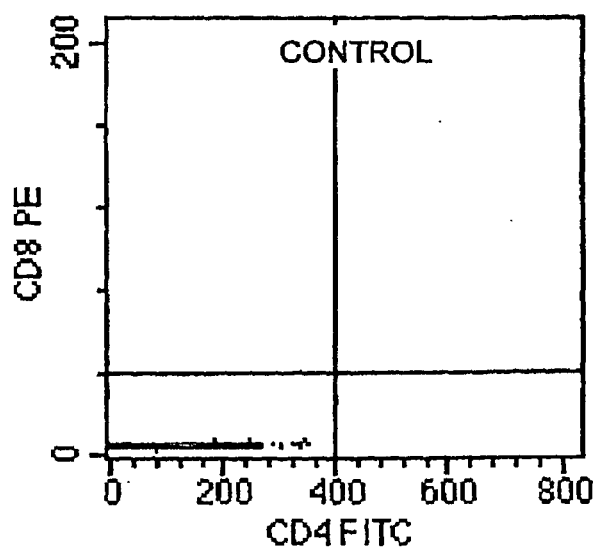
FIG. 58 is a dot plot of the results of CD4+ cells separated from human peripheral blood with a CD4+ cell separating column that were fluorescently labeled with a control antibody when subjected to flow cytometry.
Figure 59:
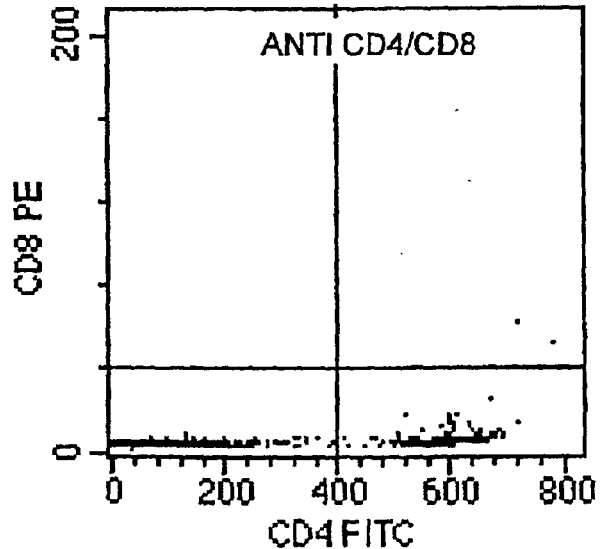
FIG. 59 is a dot plot of the results of CD4+ cells separated from human peripheral blood with a CD4+ cell separating column that were fluorescently labeled at CD4 (CD4 FITC) and CD8 (CD8 PE) on cell surfaces thereof when subjected to flow cytometry.

In order to determine the ratio of CD4+ T cells in the lymphocyte suspensions, 20 μl of anti-CD4/CD8 antibody (Simultest (Leu-3A/2a), Becton Dickinson) and a control antibody (Simultest control, Becton Dickinson) was mixed with 50 μl of the cell suspension in a 2 ml microtube and incubated on ice in the dark for 30–45 minutes, and the mixture was subjected to fluorescent staining of the CD4 and CD8 on the cell surface. The mixture was diluted with 2 ml PBS(-), mixed with vortexing, centrifuged at 300×g for 5 minutes, and then the supernatant was removed by pipetting or aspiration. The precipitate was suspended in 1 ml of PBS(-), the lymphocyte suspension was applied to a flow cytometer (FACSCalibur, Becton Dickinson) and analyzed for CD4 and CD8. The results confirmed abundant CD8+ cells among the peripheral blood lymphocytes before the column separation (FIG. 56). In contrast, although about 50% of the obtained cells from the CD4+ cell separation procedure described above was CD4 negative or weakly positive, there was no contamination of CD8+ cells (FIG. 59). Accordingly the purified cells was used as CD4 positive cells for further experiments.

(17) Activation of Helper T Cells (CD4+ Cells)

After adding 1 μg/ml (final concentration) of ionomycin (SIGMA) and 30 nM PMA (SIGMA) to the CD4 positive cells obtained in (16) (cell density: $1.0 \times 10^7$ cells/ml), the mixture was incubated for 2 hours at 37° C. in the presence of 5% $CO_2$.

(18) Fluorescent Labeling of Intracellular IL-2 mRNA of Helper T Cells (CD4+ Cells)

0.9 ml of the activated CD4+ cell suspension obtained in (17) was transferred to an electroporation cuvette (Gene Pulser specialized cuvette (electrode spacing=0.4 cm), BIO-RAD), and after adding 5.4 nmol (final concentration: 6.0 μM) of Bodipy493-503-labeled donor probe IL-2 342–356 (D) and 5.3 nmol (final concentration: 5.86 μM) of Cy5-labeled acceptor probe IL-2 357–371(A), a pulse was applied to the cells at 250 V, 975 μF. The cell suspension was filtered through 70 μm Cell Strainer (Falcon), and after moderate centrifugation the cells were resuspended with PBS(-). The cell suspension was then filtered through 40 μm Cell Strainer (Falcon) to remove as much of the dead cell-containing debris as possible, centrifuged and the precipitates was resuspended with PBS(-). Some of the cells was transferred to a cover glass chamber (Lab-Tek II Chambered Coverglass #155409, NUNC Co.) and observed under a fluorescence microscope to examine the ratio of fluorescing cells among all the cells in the visual field.

[1] A/A {fluorescence of A (acceptor dye) emitted from cells when the excitation light for A was irradiated to the cells}

[2] D/A {fluorescence of A emitted from cells when the excitation light for D (donor dye) was irradiated to the cells; FRET fluorescence}

[3] D/D {fluorescence of D emitted from cells when the excitation light for D was irradiated to the cells}

Figure 60:
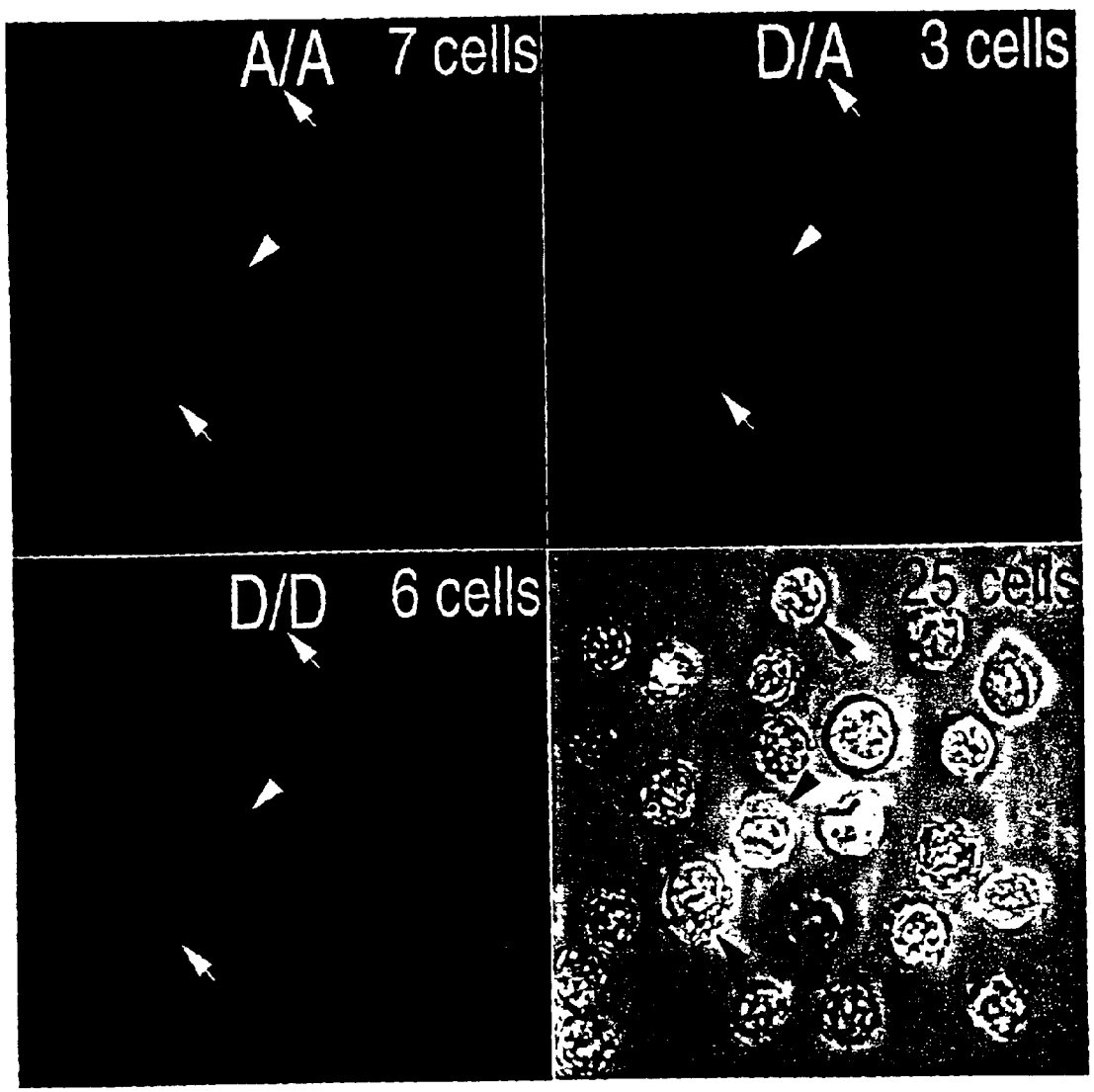
FIG. 60 is a set of micrographs showing A/A, D/A and D/D fluorescence images of a hybrid formed by the three components, intracellular IL-2 mRNA of a CD4+ cell (helper T cell) in the live state, IL-2 342–356(D) and IL-2 357–371(A), and the corresponding phase contrast micrograph.

Three cells in the entire visual field (25 cells) were observed emitting D/A fluorescence, indicating specific fluorescent labeling of IL-2 mRNA based on hybridization between the mRNA and the donor and acceptor probes. This result suggested that TH1 cells present at about 12% in activated CD4+ cells (FIG. 60).

(19) Selective Separation of TH1 by Flow Cytometry From Activated CD4+ Cells

The difference in fluorescence intensity (between IL-2 mRNA carrying and non-carrying cells) produced by FRET fluorescence caused by hybridization of IL-2 mRNA with the donor and acceptor probe in live cells was utilized in the following attempt to selectively separate TH1.

Figure 63:
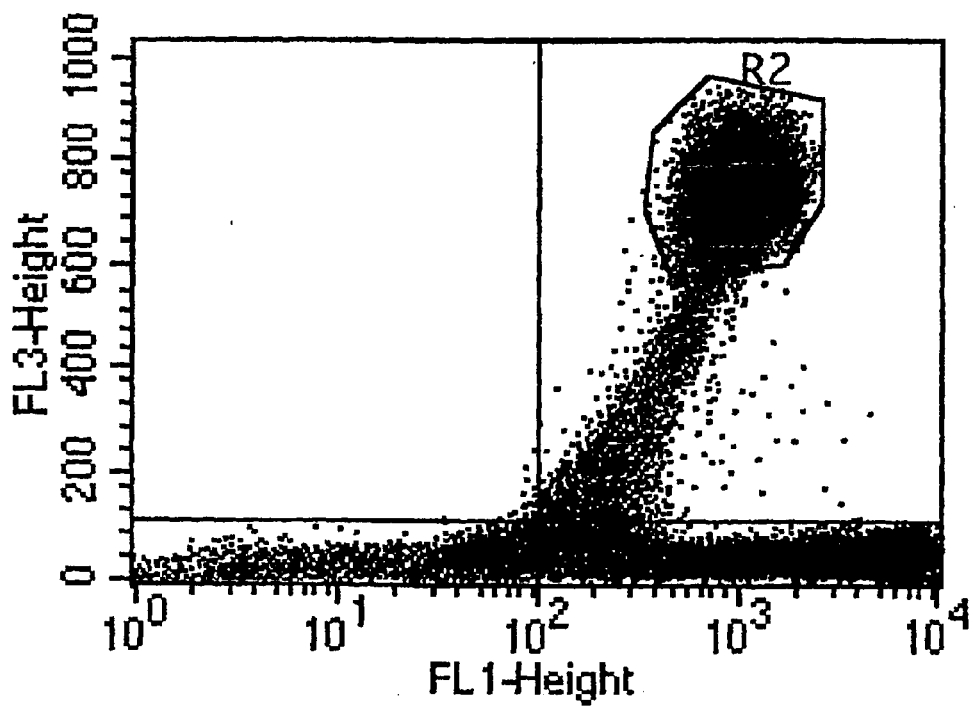
FIG. 63 is a dot plot of the results based on relative fluorescence intensity of the energy donor fluorescent dye and relative fluorescence intensity of the energy acceptor fluorescent dye due to FRET, of the cell group of CD4+ cells (helper T cells) of FIG. 60 when subjected to flow cytometry (R2 is the region selected for fluorescing cells due to FRET).
Figure 64:
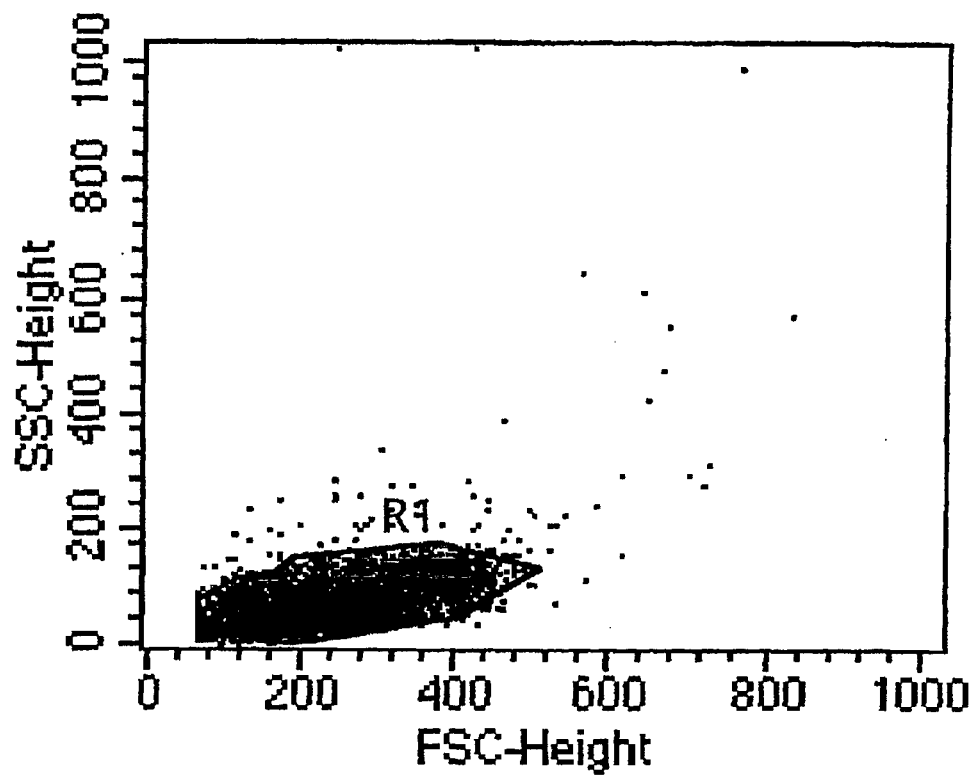
FIG. 64 is a dot plot of the results based on forward scattering light (FSC) and side scattering light (SSC) for the cell sorter-separated cell group of FIG. 61 when subjected to flow cytometry (where R1 is the region selected for live cells to be measured).
Figure 65:
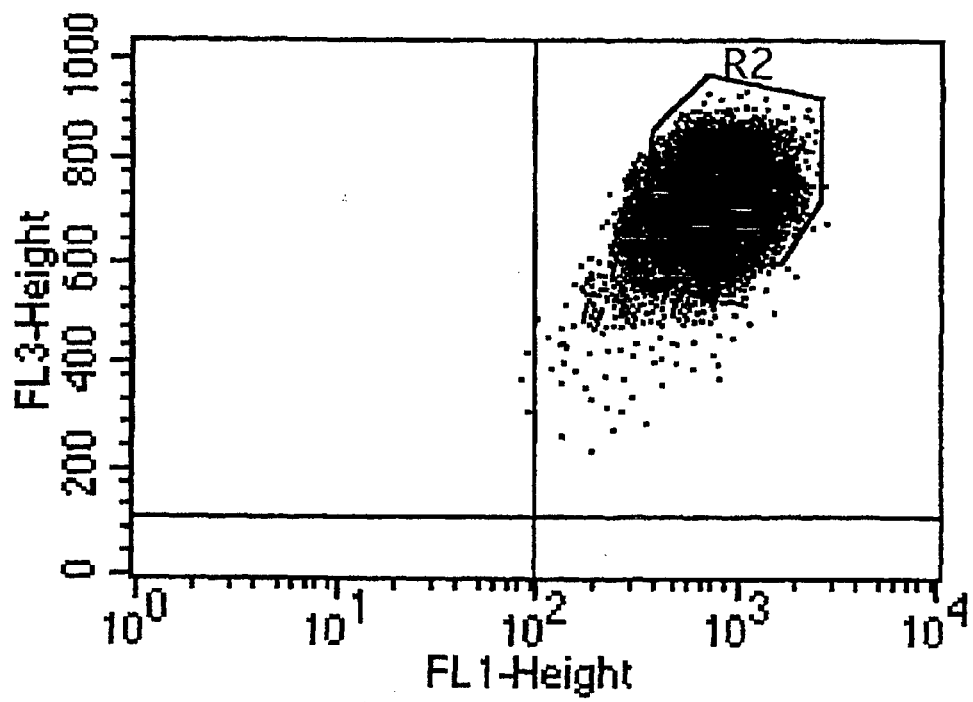
FIG. 65 is a dot plot of the results based on relative fluorescence intensity of the energy donor fluorescent dye and relative fluorescence intensity of the energy acceptor fluorescent dye due to FRET, for the cell sorter-separated cell group of FIG. 61 when subjected to flow cytometry (R2 is the region selected for fluorescing cells based on FRET).
Figure 66:
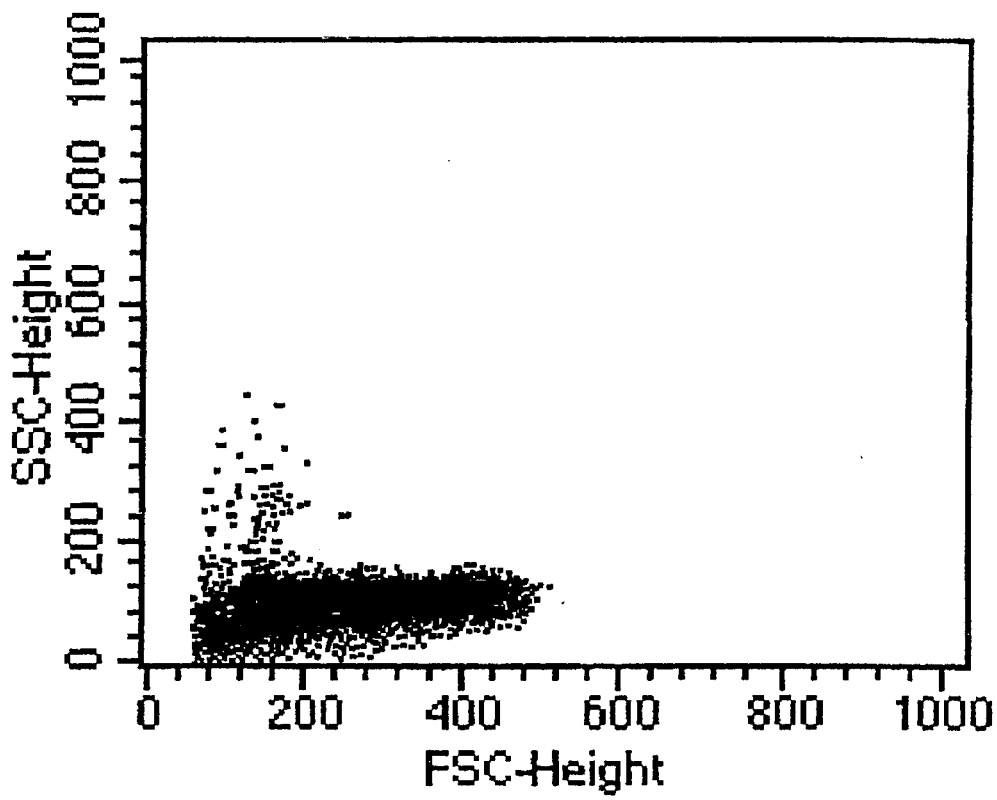
FIG. 66 is a dot plot of the results based on forward scattering light (FSC) and side scattering light (SSC) for a cell group of CD4+ cells (helper T cells) with no fluorescent probes introduced, when subjected to flow cytometry.
Figure 67:
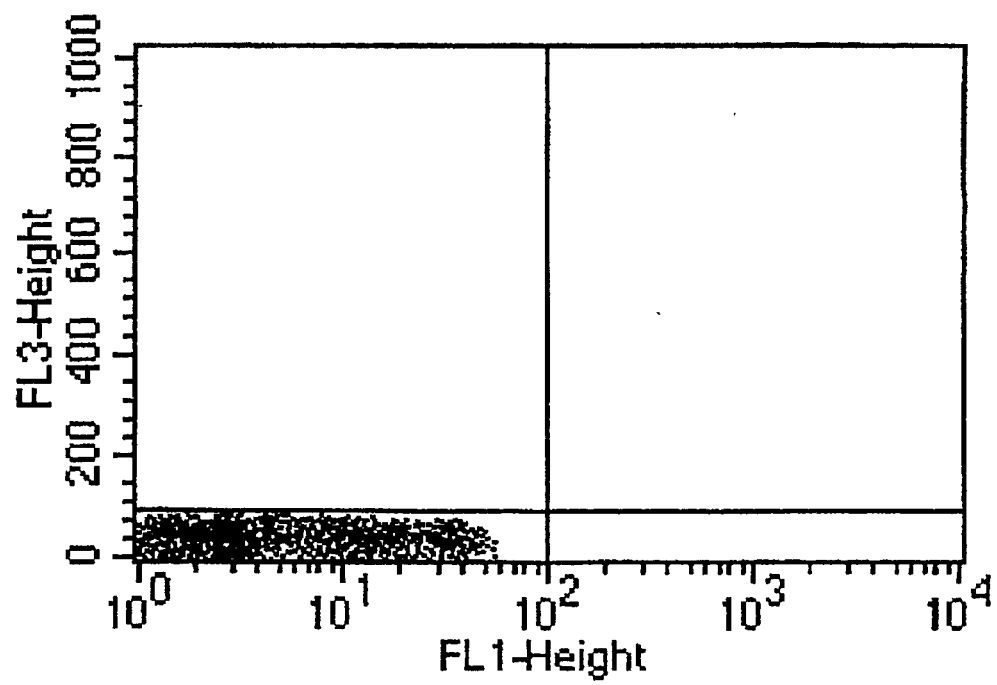
FIG. 67 is a dot plot of the results based on relative fluorescence intensity of the energy donor fluorescent dye and relative fluorescence intensity of the energy acceptor fluorescent dye due to FRET, for the cell group of CD4+ cells (helper T cells) with no fluorescent probes introduced, when subjected to flow cytometry.

A suspension of the fluorescent IL-2 probes-introduced cells prepared in (18) was applied to a flow cytometer (FACSCalibur). At a position in flow path, the excitation light of a donor fluorescent dye (Bodipy) was irradiated to the cells to detect FRET fluorescence emitted from acceptors (Cy5) caused by the hybridization, and then relative fluorescence intensity of Cy5 or Bodipy was shown as FL3-Height or FL1-Height, respectively in a dot-plots diagram. Among these plots, a group of cells with the highest value of FL3-Height was designated as R2 (FIG. 63). On the other hand, a group of typical human lymphocytes in the points of cell size (FSC-Height; forward-scattering light) as well as the complexity in the intrastructure (SSC-Height; side-scattering light) was designated as R1 according to the reference value (FACSCalibur Training Manual, BECTON DICKINSON). Cells belonging to both R1 and R2 were selectively separated using a cell sorting function. The separated cells were again applied to the FACSCalibur to confirm that they were the objective cells. The majority of the sorted out cells by the cell sorting function belonged to both R1 and R2, indicating that the cells with fluorescently labeled IL-2 mRNA had been separated out as ones emitting considerable FRET fluorescence (FIG. 65). In contrast, CD4+ cells introduced no fluorescent probes were detected as dots near at the base line of FL3-Height with only weak fluorescence at FL1-Height (FIG. 67). These results indicated that cells with specifically fluorescent labeled IL-2 mRNA can be clearly distinguished on dot plots.

Figure 61:
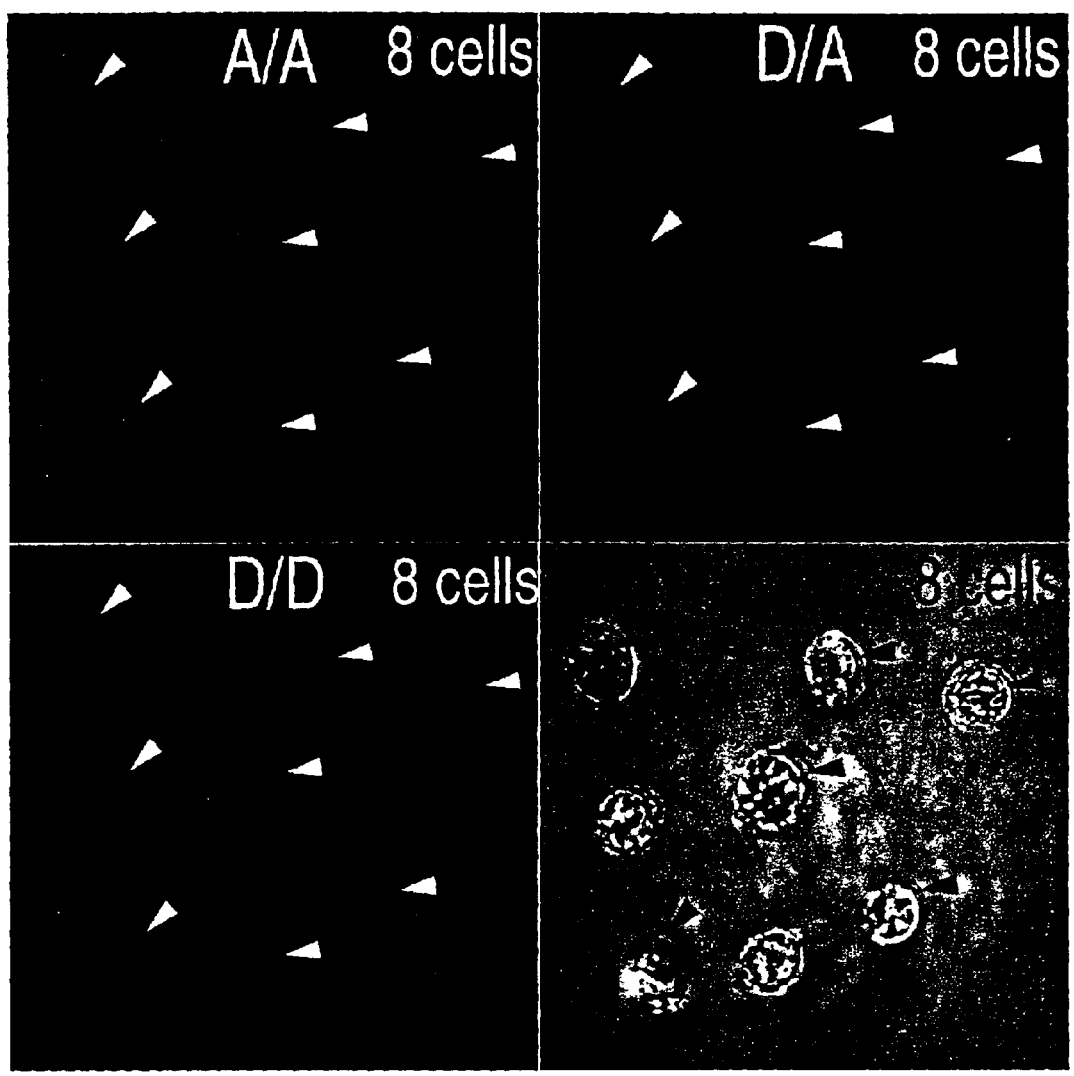
FIG. 61 is a set of micrographs showing A/A, D/A and D/D fluorescence images, and the corresponding phase contrast micrograph, of a cell group obtained by selective separation of the CD4+ cell group of FIG. 60 in the live state according to flow cytometry by gating with the R1 gate of FIG. 62 and the R2 gate of FIG. 63.
Figure 62:
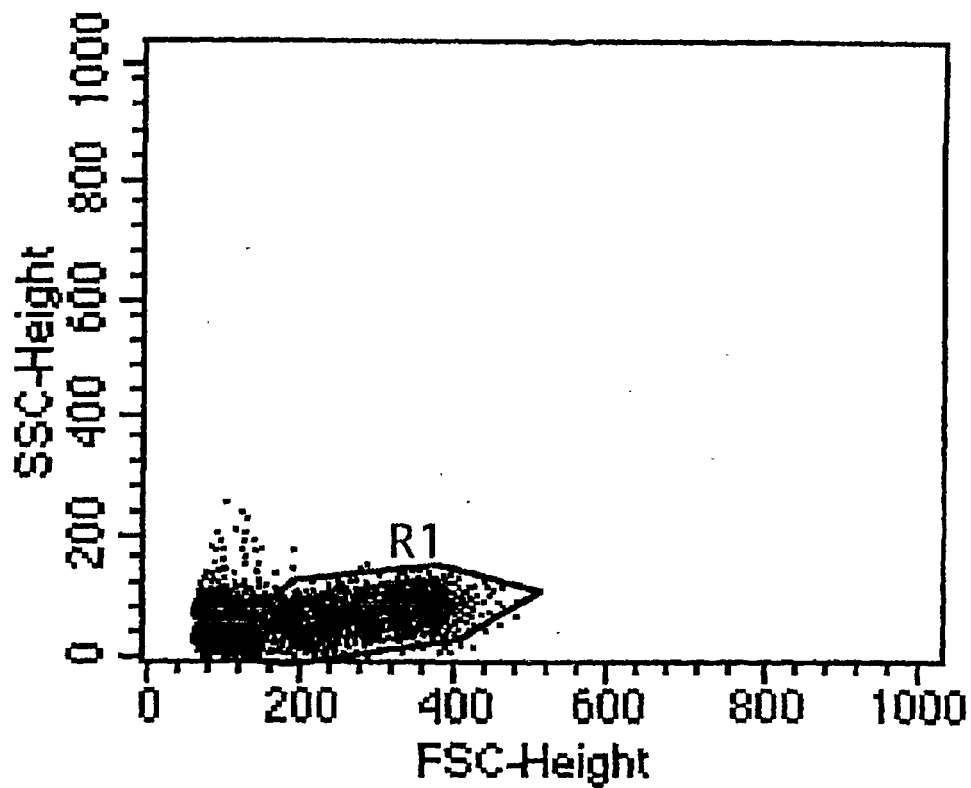
FIG. 62 is a dot plot of the results based on forward scattering light (FSC) and side scattering light (SSC) for the cell group of CD4+ cells (helper T cells) of FIG. 60 when subjected to flow cytometry (R1 is the region selected for live cells to be measured).

Some of the sorted out cells were then observed under a fluorescence microscope in the same manner as (18). All 8 cells in the entire visual field emitted D/A (FRET fluorescence), suggesting that IL-2 mRNA was fluorescently labeled in all the sorted out cells (FIG. 61). Comparing the result above with that before cytometry in (18) for the ratios of CD4+ cells with fluorescent labeled IL-2 mRNA, it was suggested that TH1 had been selectively separated by the cell sorting function.

(20) Fluorescent Labeling of Intracellular IL-4 mRNA of helper T Cells (CD4+ Cells)

Figure 68:
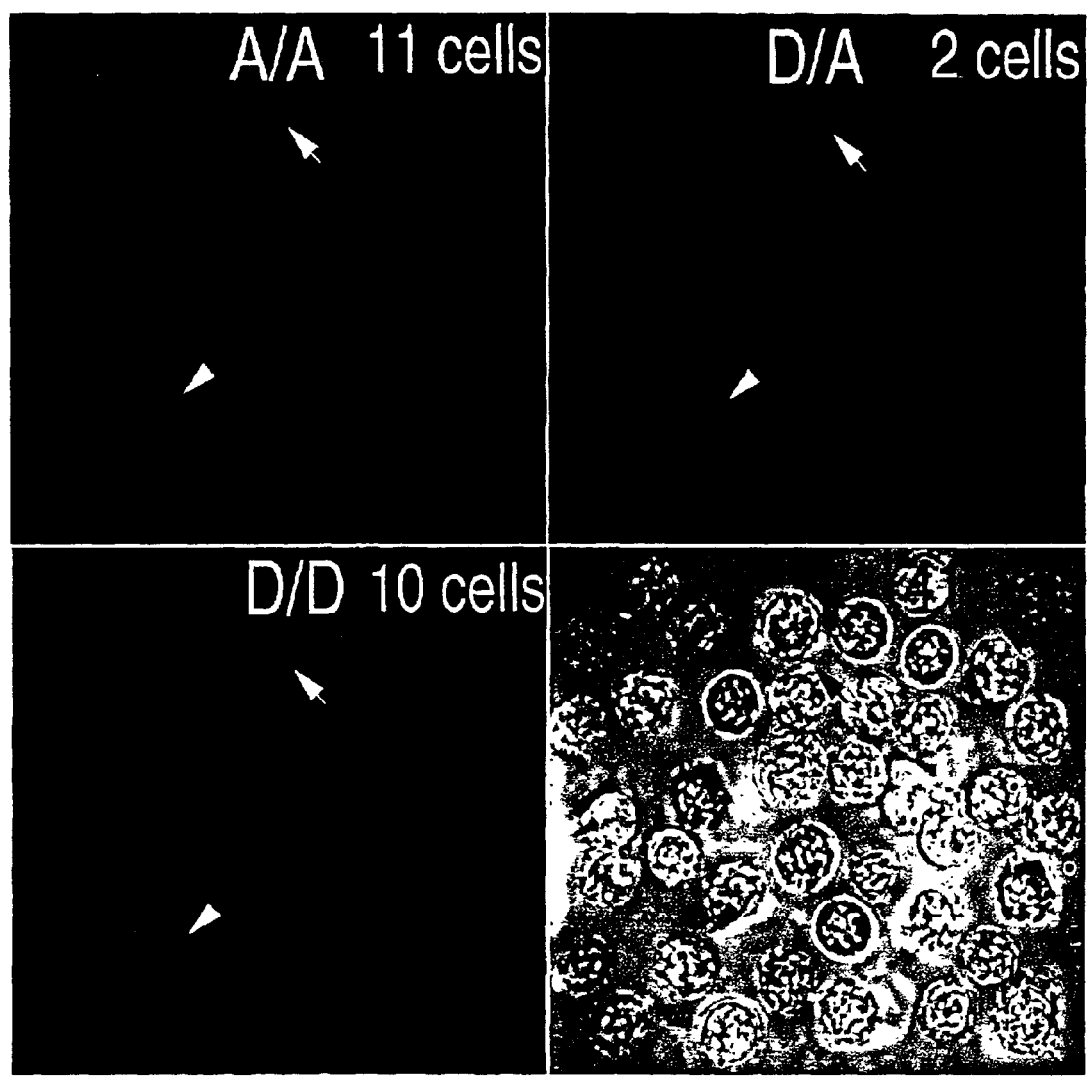
FIG. 68 is a set of micrographs showing A/A, D/A and D/D fluorescence images of a hybrid formed by the three components, intracellular IL-4 mRNA of CD4+ cells (helper T cells) in the live state, IL-4 265–279(D) and IL-4 280–294(A) and the corresponding phase contrast micrograph.

0.9 ml of the activated CD4+ cell suspension obtained in (17) was transferred to an electroporation cuvette (BIO-RAD) in the same manner as (18), and after adding 15.1 nmol (final concentration: 16.8 μM) of Bodipy493-503-labeled donor probe IL-4 265–279 and 13.6 nmol (final concentration: 15.1 μAM) of Cy5-labeled acceptor probe IL-4 280–294, a pulse was applied to the cells at 250 V, 975 μF. In the same manner as (18), the cell suspension was filterated through 70 μm Cell Strainer (Falcon), and after moderate centrifugation the cells were resuspended with PBS(-). To remove as much of the dead cell-containing debris as possible, the suspension was then filtered through 40 μm Cell Strainer (Falcon), centrifuged and resuspended and then the cells were transferred to a cover glass chamber (NUNC) and observed under a fluorescence microscope to examine the ratio of A/A, D/A and D/D fluorescing cells among the total cells in the visual field, in the same manner as (18). Two cells in the entire visual field (41 cells) were emitting D/A fluorescence, indicating specific fluorescent labeling of IL-4 mRNA based on hybridization between the mRNA and the donor and acceptor probes (FIG. 68). This result suggested that TH2 is present at about 5% in activated CD4+ cells.

(21) Selective Separation of TH2 by Flow Cytometry From Activated CD4+ Cells

The difference in fluorescence intensity (between IL-4 mRNA carrying and non-carrying cells) caused by FRET fluorescence based on hybridization of IL-4 mRNA with the donor and acceptor probe in live cells was utilized to selectively separate TH2.

Figure 70:
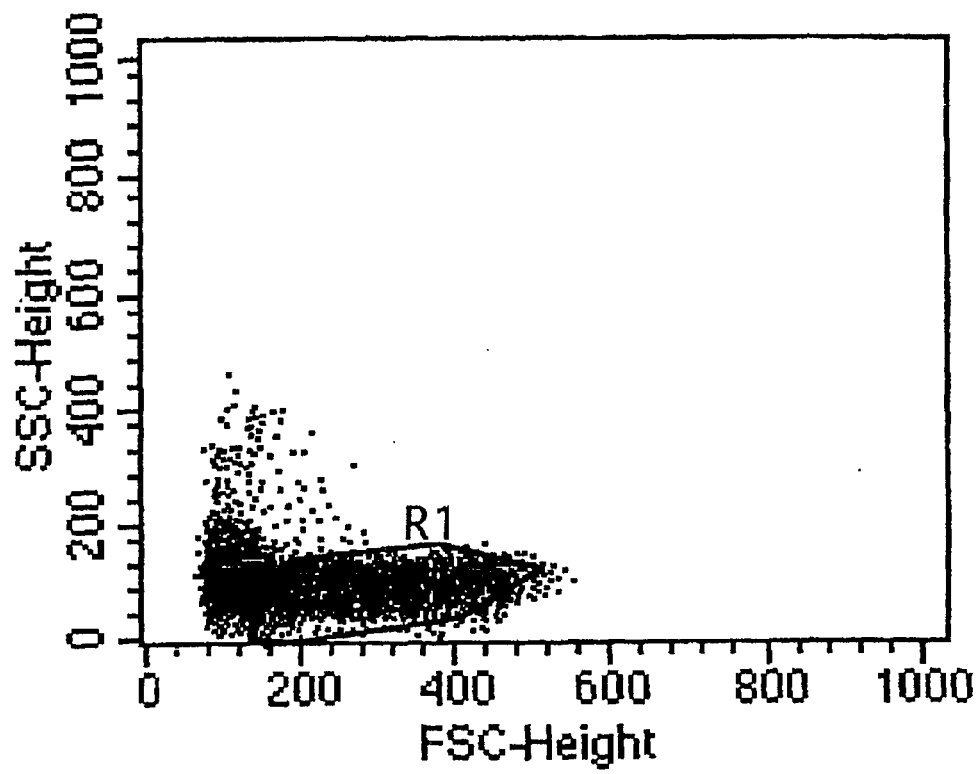
FIG. 70 is a dot plot of the results based on forward scattering light (FSC) and side scattering light (SSC) for the cell group of CD4+ cells (helper T cells) in the live state of FIG. 68 when subjected to flow cytometry (R1 is the region selected for live cells to be measured).
Figure 71:
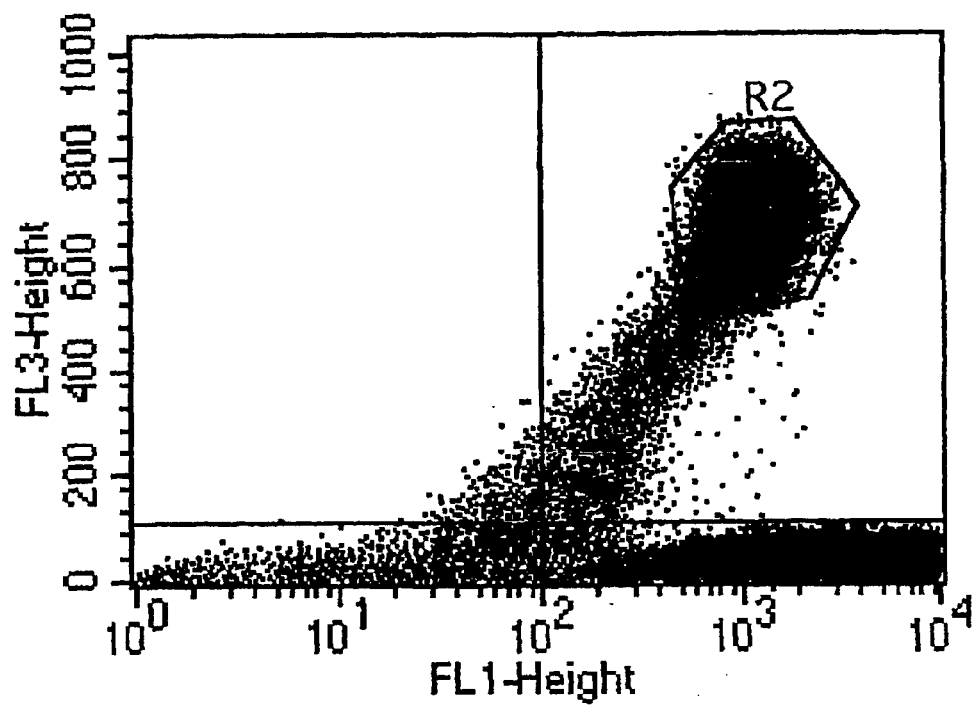
FIG. 71 is a dot plot of the results based on relative fluorescence intensity of the energy donor fluorescent dye and relative fluorescence intensity of the energy acceptor fluorescent dye due to FRET, for the cell group of CD4+ cells (helper T cells) of FIG. 68 when subjected to flow cytometry (R2 is selected for fluorescing cells due to FRET).
Figure 72:
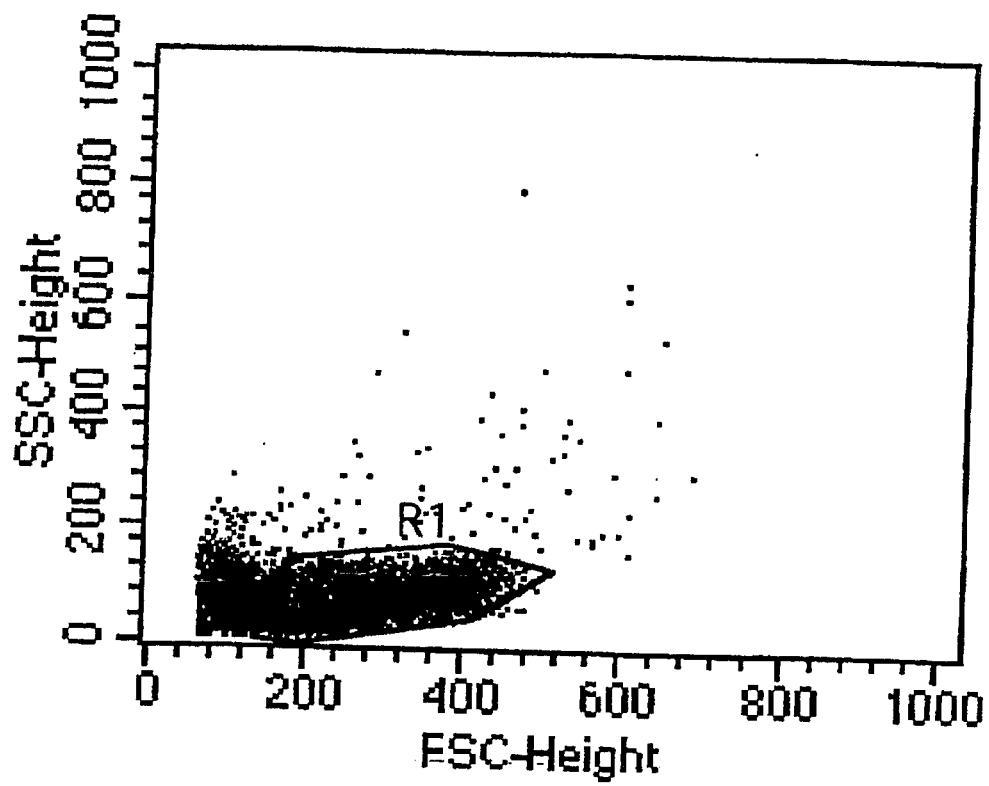
FIG. 72 is a dot plot of the results based on forward scattering light (FSC) and side scattering light (SSC) for the cell sorter-separated cell group of FIG. 69 when subjected to flow cytometry (R1 is the region selected for live cells to be measured).
Figure 73:
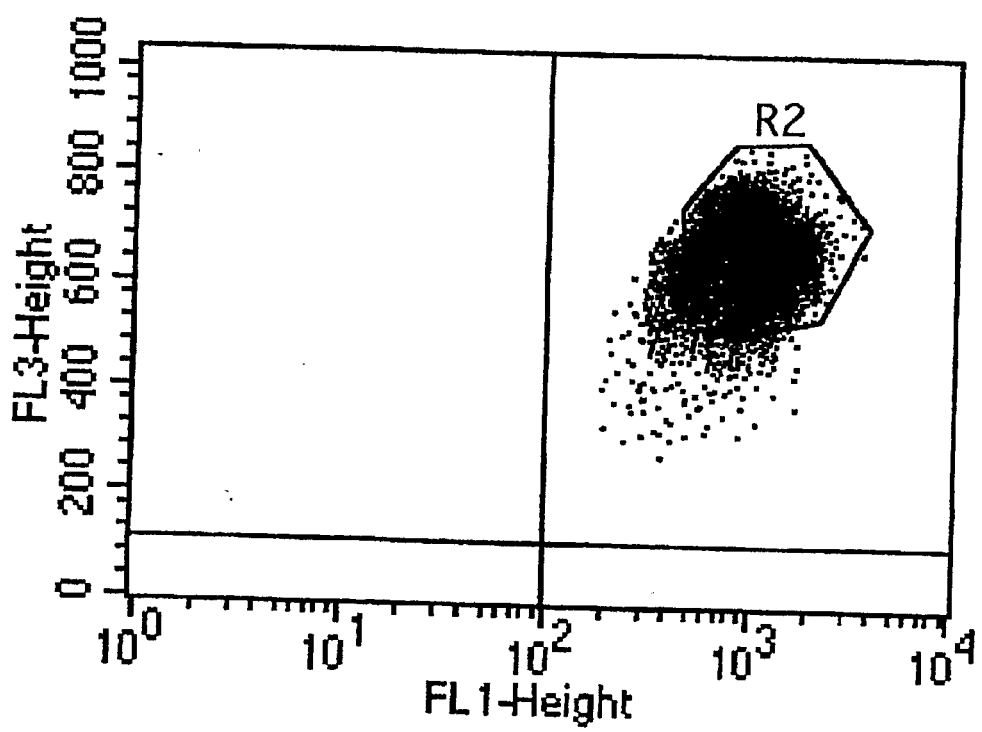
FIG. 73 is a dot plot of the results based on relative fluorescence intensity of the energy donor fluorescent dye and relative fluorescence intensity of the energy acceptor fluorescent dye due to FRET, for the cell sorter-separated cell group of FIG. 35 when subjected to flow cytometry (R2 is the region selected for fluorescing cells based on FRET).

A suspension of the fluorescent probes-introduced cells obtained in (20) was applied to a flow cytometer (FACSCalibur). The excitation light of a donor dye (Bodipy) was irradiated to the cells to detect FRET fluorescence emitted from acceptors (Cy5) based on the hybridization in the same manner as (19), and then relative fluorescence intensity of Bodipy or Cy5 was shown as FL1-Height or FL3-Height, respectively in dot-plots diagram. Among these plots, a group of cells with the highest value of FL3-Height was designated as R2 (FIG. 71). On the other hand, a group of typical human lymphocytes in the points of cell size (FSC-Height; forward-scattering light) as well as the complexity in the intrastructure (SSC-Height; side-scattering light) was designated as R1 (FIG. 70). Cells belonging to both R1 and R1 was selectively separated using a cell sorting function. The separated cells were again applied to FACSCalibur and examined to confirm that they were the objective fluorescently labeled cells. The majority of the sorted out cells by the cell sorting function belonged to both R1 and R2 (FIGS. 72 and 73), indicating that the cells with fluorescent labeled IL-4 mRNA had been separated out as ones emitting considerable FRET fluorescence.

Figure 69:
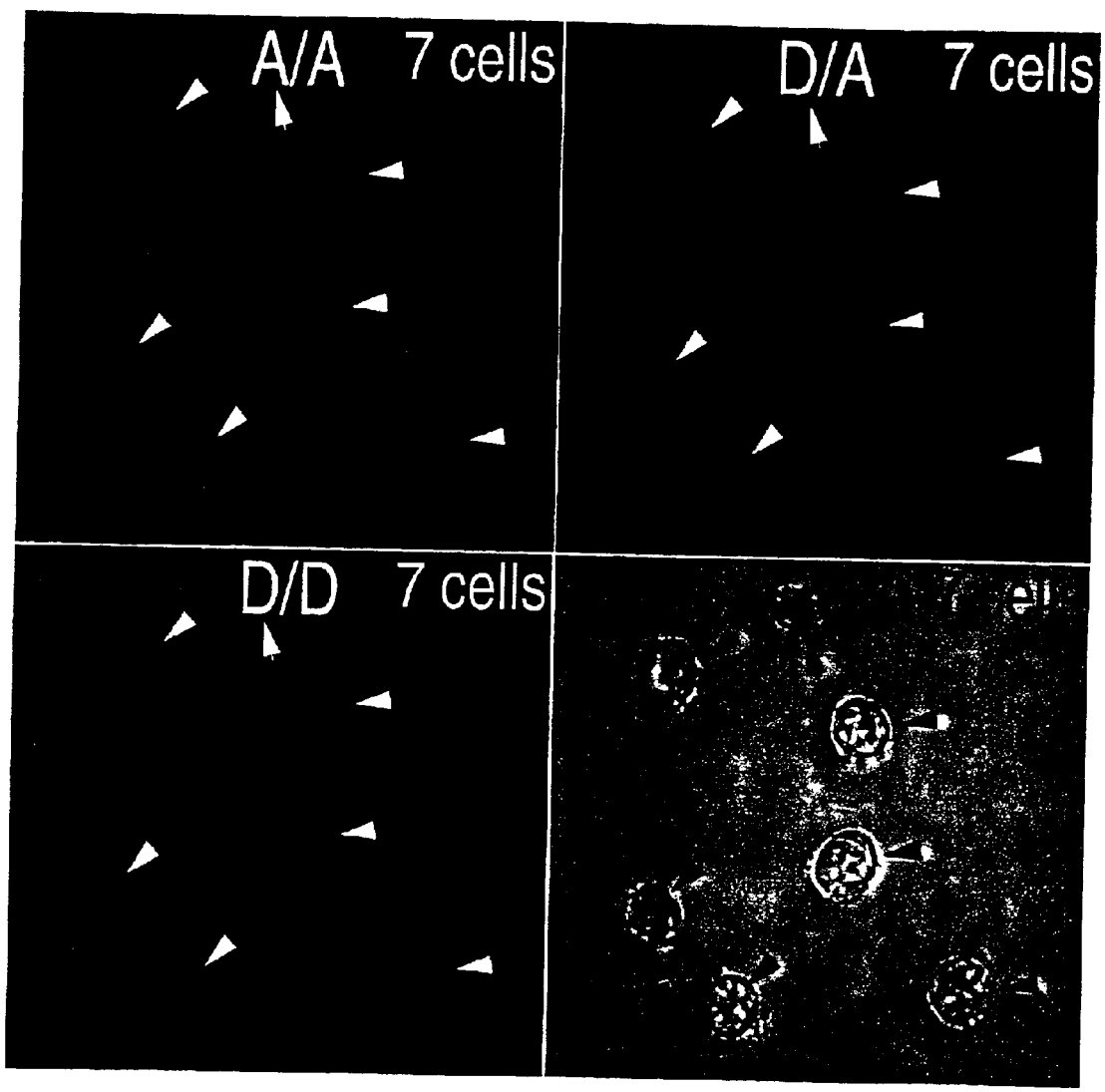
FIG. 69 is a set of micrographs showing A/A, D/A and D/D fluorescence images, and the corresponding phase contrast micrograph, of the cell group obtained by selective separation of CD4+ cell group in the live state of FIG. 68 according to flow cytometry by gating with the R1 gate of FIG. 70 and the R2 gate of FIG. 71.

Some of the sorted-out cells were then observed under a fluorescence microscope in the same manner as (20). All 7 cells in the entire visual field emitted D/A (FRET fluorescence), suggesting that IL-4 mRNA was fluorescently labeled in all the sorted-out cells (FIG. 69). Comparing the result above with that before cytometry in (20) for the ratios of CD4+ cells with fluorescent labeled IL-4 mRNA, it was suggested that TH2 had been selectively separated by the cell sorting function.

(22) Induction of TH2 Among Helper T Cells (CD4+ Cells)

A balance between TH1 and TH2 is maintained in healthy bodies, and it is believed that this balanced relationship supports homeostasis in immune system of the body. Conversely, disruption of the balance between TH1 and TH2 is a cause of onset of numerous immune diseases. While there is no doubt that factors causing disruption in this balance in the body are the sources responsible for such diseases, the mechanisms leading to their onset are too complicated to reconstitute in vitro. Nevertheless, several approaches to mimic the disruption have long been performed as follows. When TH2 is dominant over TH1, it promotes excess production and secretion of immunoglobulins (antibody molecules) by B cells as their humoral immune function. In this unbalanced state, the production of autoantibodies (react with self components to cause tissue damage) is induced to result in autoimmune diseases. An approach to mimic this condition by artificially preparing a TH2-dominant helper T cell group is one utilizing the property of TH2, "IL-4 autocrine", i.e., TH2 activates itself by a cytokine (IL-4) which it produces", whereby a helper T cell group is treated with a high concentration of IL-4 to induce differentiation to TH2 (Openshaw, P. et al., J. Exp. Med. 182(5), 1357, 1995). Here, 20 ng/ml (final concentration) of human recombinant IL-4 (Genzyme) was added with 1 $\mu$g/ml ionomycin and 30 nM PMA as described in (17) to CD4+ cells obtained in (16), and the cells were incubated at 37° C. for 2 hours.

Figure 74:
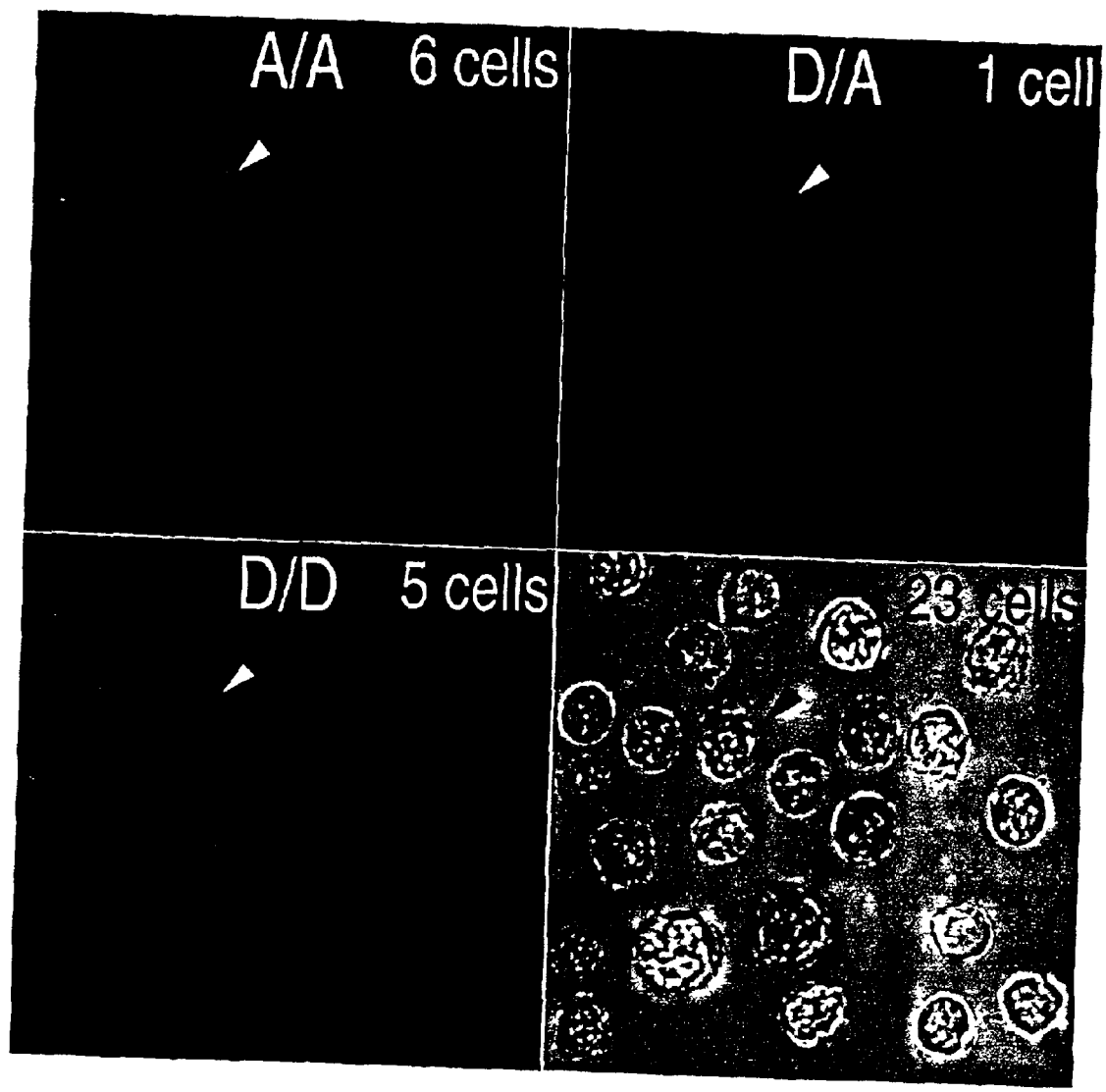
FIG. 74 is a set of micrographs showing A/A, D/A and D/D fluorescence images of a hybrid formed by the three components, intracellular IL-2 mRNA of TH2-induced CD4+ cell in the live state (helper T cell), IL-2 342–356(D) and IL-2 357–371(A) and the corresponding phase contrast micrograph.

(23) Fluorescent Labeling of TH1 Intracellular IL-2 mRNA Among TH2-Dominant Helper T Cells TH1 cells were selectively separated and obtained from TH2-dominant helper T cell group in which TH1 is sparsely present as follows. 0.9 ml of the TH2-induced CD4+ cell suspension obtained in (22) was transferred to an electroporation cuvette (BIO-RAD) in the same manner as (18). After adding 5.4 nmol (final concentration: 6.0 $\mu$M) of Bodipy493-503-labeled donor probe IL-2 342–356 and 5.3 nmol (final concentration: 5.86 $\mu$M) of Cy5-labeled acceptor probe IL-2 357–371, a pulse was applied to the cells at 250 V, 975 $\mu$F. In the same manner as (18), the debris containing most of the dead cells was removed from the cell suspension and then some of the cells were transferred to a cover glass chamber (NUNC) and observed under a fluorescence microscope to examine the ratio of A/A, D/A and D/D fluorescing cells among the cells in the entire visual field. One cell in the entire visual field (23 cells) was emitting D/A fluorescence, indicating the presence of a cell with specific fluorescent labeling of IL-2 mRNA (FIG. 74). Comparing this result with that in (18), it was suggested that TH1 is reduced to approximately 4% in the TH2-dominant CD4+ cells from 12% in the unselectively activated CD4+ cells (FIG. 60).

(24) Selective Separation of TH1 by Flow Cytometry From TH2-Dominant Helper T Cell Group The difference in fluorescence intensity (between IL-2 mRNA carrying and non-carrying cells) caused by FRET fluorescence based on hybridization of IL-2 mRNA with the donor and acceptor probe in live cells was utilized to selectively separate TH1.

Figure 76:
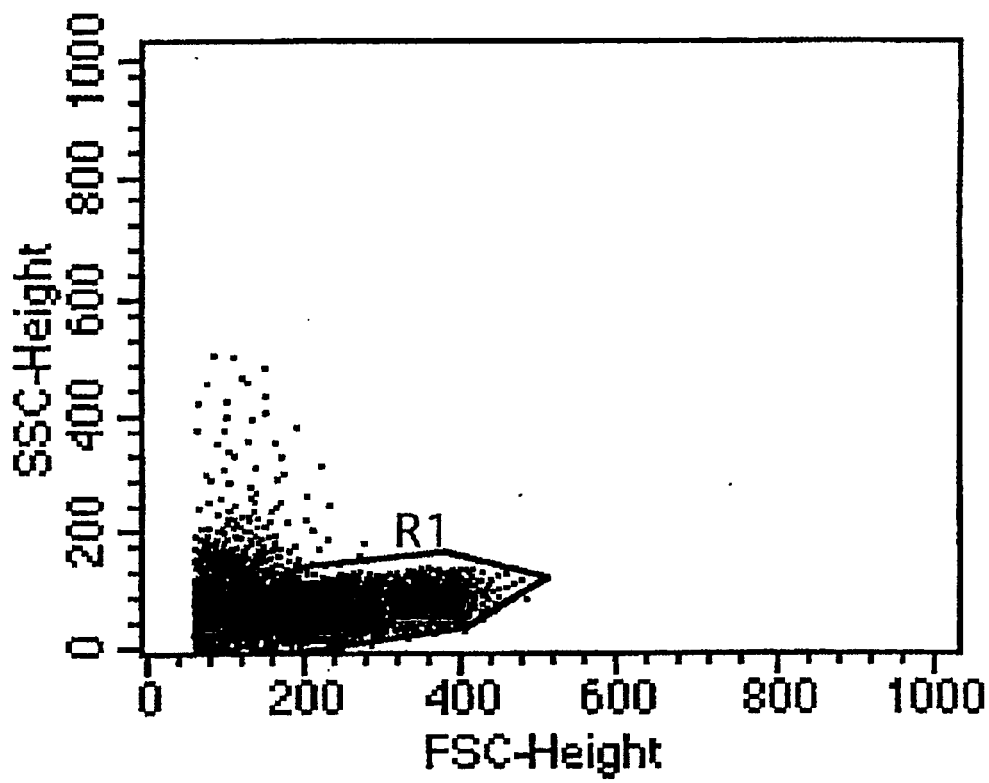
FIG. 76 is a dot plot of the results based on forward scattering light (FSC) and side scattering light (SSC) for the cell group of CD4+ cells (helper T cells) of FIG. 74 when subjected to flow cytometry (R1 is the region selected for live cells to be measured).
Figure 77:
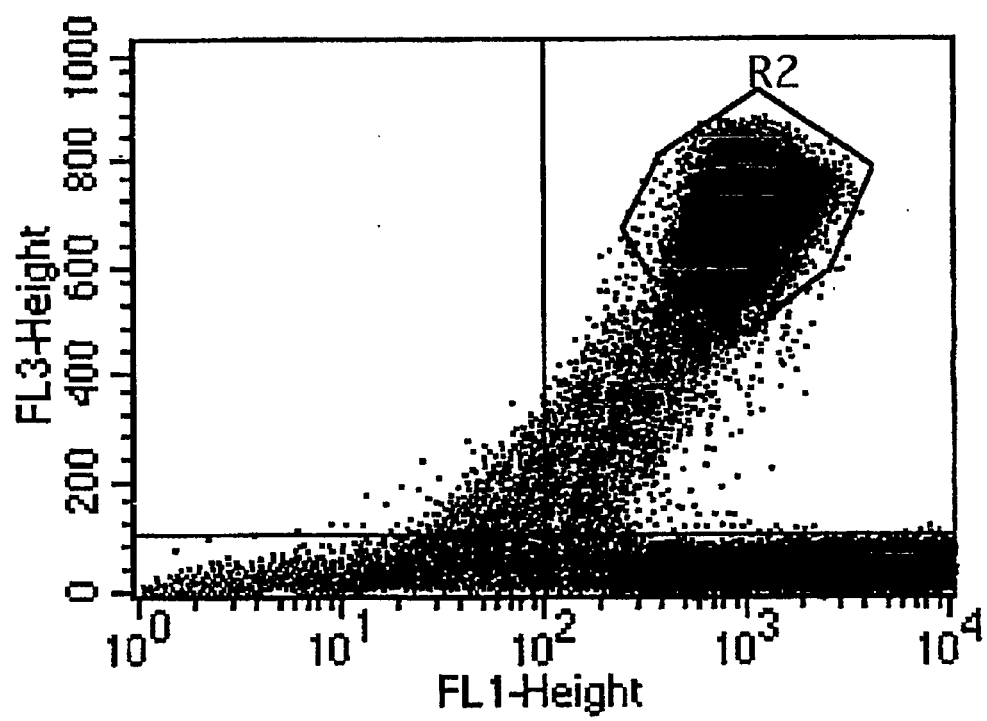
FIG. 77 is a dot plot of the results based on relative fluorescence intensity of the energy donor fluorescent dye and relative fluorescence intensity of the energy acceptor fluorescent dye due to FRET, for the cell group of CD4+ cells (helper T cells) of FIG. 74 when subjected to flow cytometry (R2 is the region selected for fluorescing cells based on FRET).

A suspension of the fluorescent probes-introduced cells obtained in (23) was applied to a flow cytometer (FACSCalibur). The excitation light of a donor dye (Bodipy) was irradiated to the cells to detect FRET fluorescence emitted from acceptors (Cy5) based on the hybridization in the same manner as (19), and then relative fluorescence intensity of Bodipy or Cy5 was shown as FL1-Height or FL3-Height, respectively in dot-plots diagram, Among these plots, a group of cells with the highest value of FL3-Height was designated as R2 (FIG. 77). On the other hand, a group of typical human lymphocytes in the points of cell size (FSC-Height; forward-scattering light) as well as the complexity in the intrastructure (SSC-Height; side-scattering light) was designated as R1 (FIG. 76). Cells belonging to both R1 and R2 were selectively separated using a cell sorting function.

Figure 78:
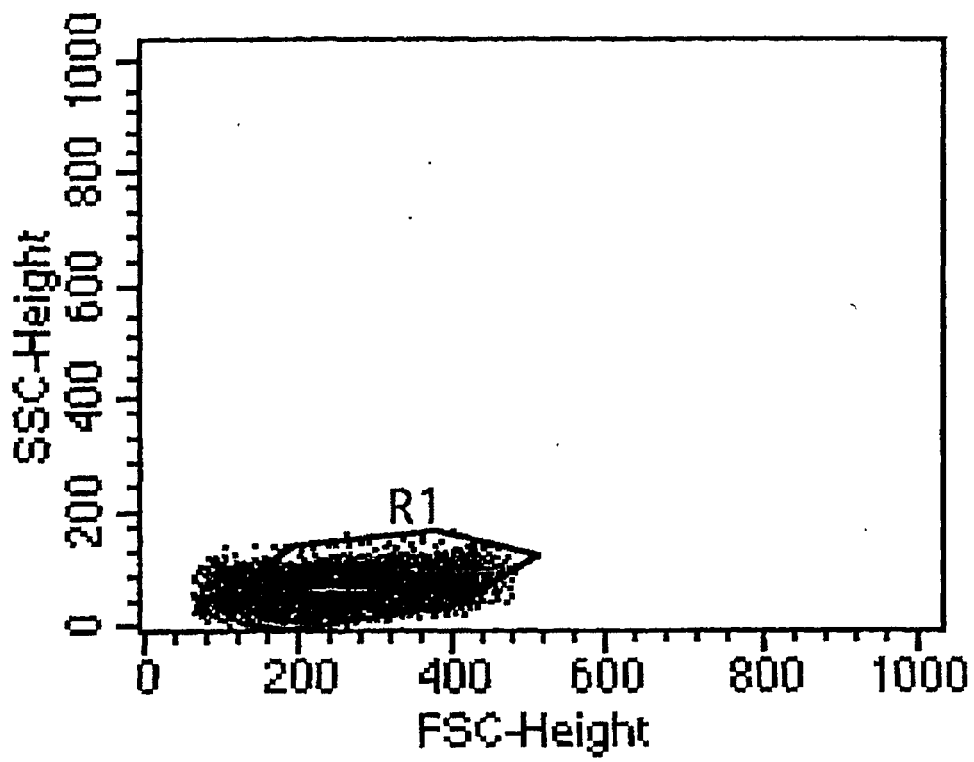
FIG. 78 is a dot plot of the results based on forward scattering light (FSC) and side scattering light (SSC) for the cell sorter-separated cell group of FIG. 75 when subjected to flow cytometry (R1 is the region selected for live cells to be measured).
Figure 79:
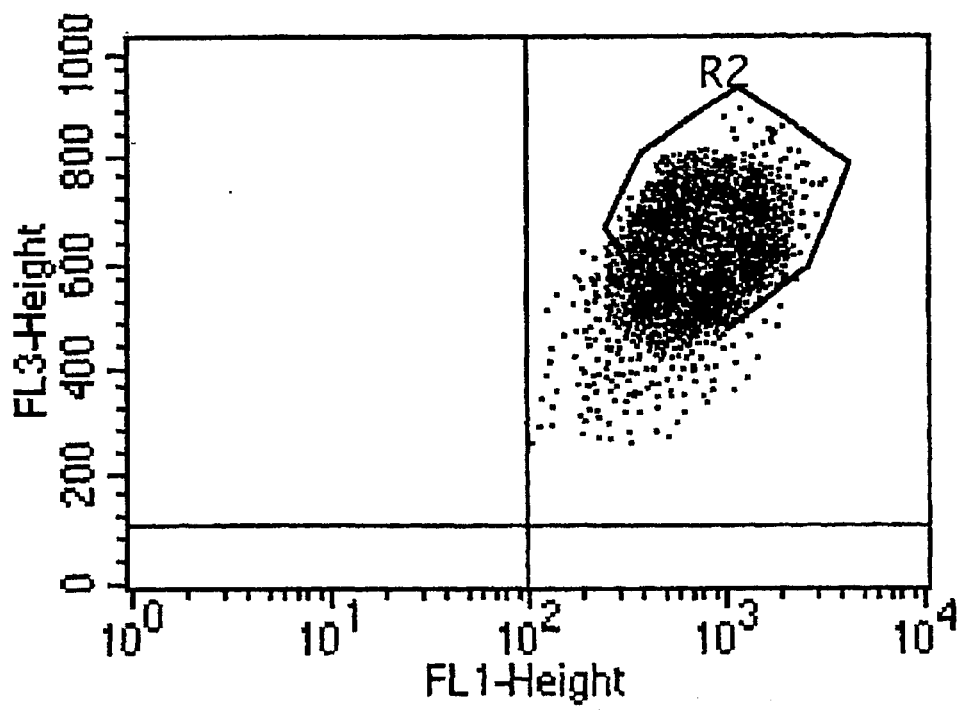
FIG. 79 is a dot plot of the results based on relative fluorescence intensity of the energy donor fluorescent dye and relative fluorescence intensity of the energy acceptor fluorescent dye due to FRET, for the cell sorter-separated cell group of FIG. 75 when subjected to flow cytometry (R2 is the region selected for fluorescing cells based on FRET).

The separated cells were again applied to the FACSCalibur and examined to confirm that they were the objective fluorescently labeled cells. The majority of the sorted out cells by the cell sorting function belonged to both R1 and R2 (FIGS. 78 and 79), indicating that the cells with fluorescent labeled IL-2 mRNA had been separated out as ones emitting considerable FRET fluorescence.

Figure 75:
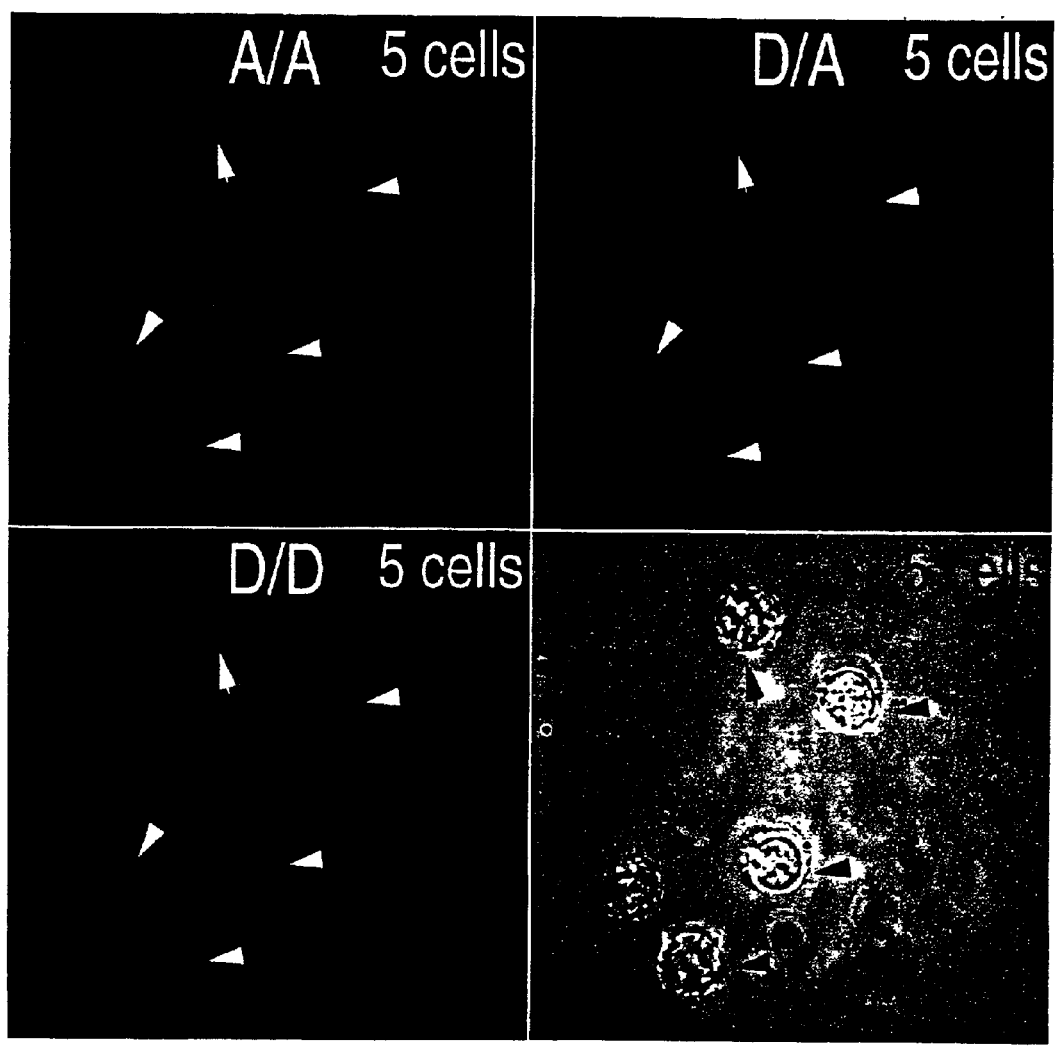
FIG. 75 is a set of micrographs showing A/A, D/A and D/D fluorescence images, and the corresponding phase contrast micrograph, of the cell group obtained by selective separation of CD4+ cell group in the live state of FIG. 74 according to flow cytometry by gating with the R1 gate of FIG. 76 and the R2 gate of FIG. 77.

Some of the sorted out cells were then observed under a fluorescence microscope in the same manner as (18). All 5 cells in the entire visual field emitted D/A (FRET fluorescence), suggesting that IL-2 mRNA was fluorescently labeled in all the sorted-out cells (FIG. 75). Comparing the result above with that before cytometry in (23) for the ratios of CD4+ cells with fluorescent labeled IL-2 mRNA, it was suggested that TH1 had been selectively separated by the cell sorting function.

(25) Induction of TH1 Among Helper T Cells (CD4+ Cells)

In contrast to (22), it is known that when TH1 is dominant over TH2, it provokes a chronic disease such as tuberculoid leprosy (Mitra, D. K. et al. Int. Immunol. 11(11), 1801, 1999). An approach to mimic this condition by artificially preparing a TH1-dominant helper T cell group is one whereby a helper T cell group is treated with the TH1-activating cytokine IL-12 and with specific antibodies for IL-4 to neutralize and inactivate IL-4 in the extracellular fluid to induce TH1 (Openshaw, P. et al., J. Exp. Med. 182(5), 1357, 1995).

Here, 10 ng/ml (final concentration) of human recombinant IL-12 (Genzyme) and 10 µg/ml anti-human IL-4 mouse monoclonal antibody (Genzyme) were added with 1 µg/ml ionomycin and 30 nM PMA as described in (17) to CD4+ cells obtained in (16), and the cells were incubated at 37° C. for 2 hours.

Figure 80:
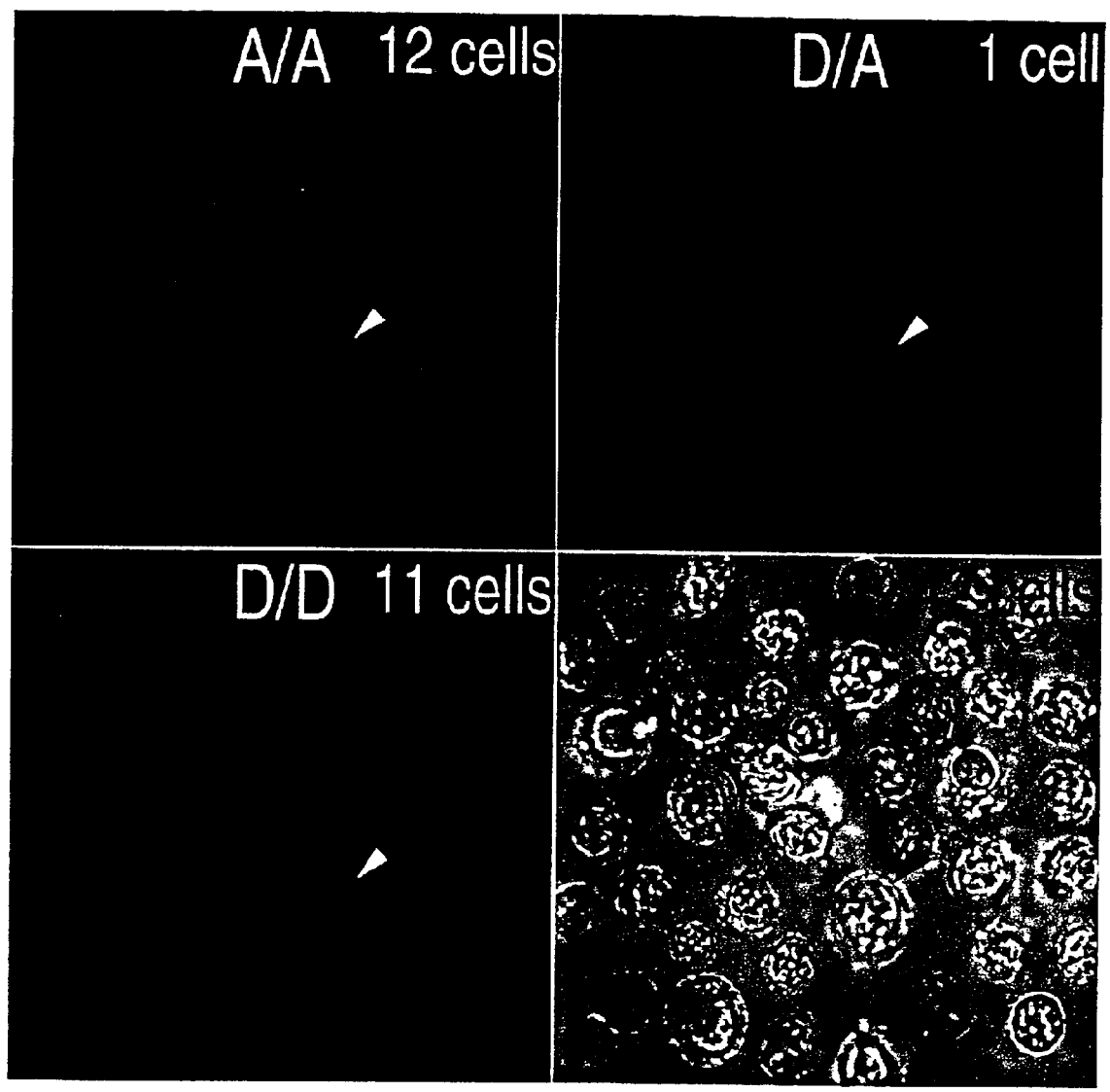
FIG. 80 is a set of micrographs showing A/A, D/A and D/D fluorescence images of a hybrid formed by the three components, the intracellular IL-4 mRNA of CD4+ cells T1 induction-treated in the live state (helper T cells), IL-4 265–279(D) and IL-4 280–294(A) and the corresponding phase contrast micrograph.

(26) Fluorescent Labeling of TH2 Intracellular IL-4 mRNA Among TH1-Dominant Helper T Cells TH2 cells were selectively separated and obtained from TH1-dominant helper T cell group in which TH2 is sparsely present as follows. 0.9 ml of the TH1-induced CD4+ cell suspension obtained in (25) was transferred to an electroporation cuvette (BIO-RAD) in the same manner as (18). After adding 15.1 nmol (final concentration: 16.8 µM) of Bodipy493-503-labeled donor probe IL-4 265–279(D) and 13.6 nmol (final concentration: 15.1 µM) of Cy5-labeled acceptor probe IL-4 280–294(A), a pulse was applied to the cells at 250 V, 975 µF. In the same manner as (18), the debris containing most of the dead cells was removed from the cell suspension and then some of the cells were transferred to a cover glass chamber (NUNC) and observed under a fluorescence microscope to examine the ratio of A/A, D/A and D/D fluorescing cells among the cells in the entire visual field. One cell in the entire visual field (42 cells) was emitting D/A fluorescence, indicating the presence of a cell with specific fluorescent labeling of IL-2 mRNA (FIG. 80). Comparing this result with that in (18), it was suggested that TH2 is reduced to approximately 2% in the TH1-dominant CD4+ cells from 5% in the unselectively activated CD4+ cells (FIG. 68).

(27) Selective Separation of TH2 by Flow Cytometry From TH1-Dominant Helper T Cell Group The difference in fluorescence intensity (between IL-4 mRNA carrying and non-carrying cells) caused by FRET fluorescence based on hybridization of IL-4 mRNA with the donor and acceptor probe in live cells was utilized to selectively separate TH2.

Figure 82:
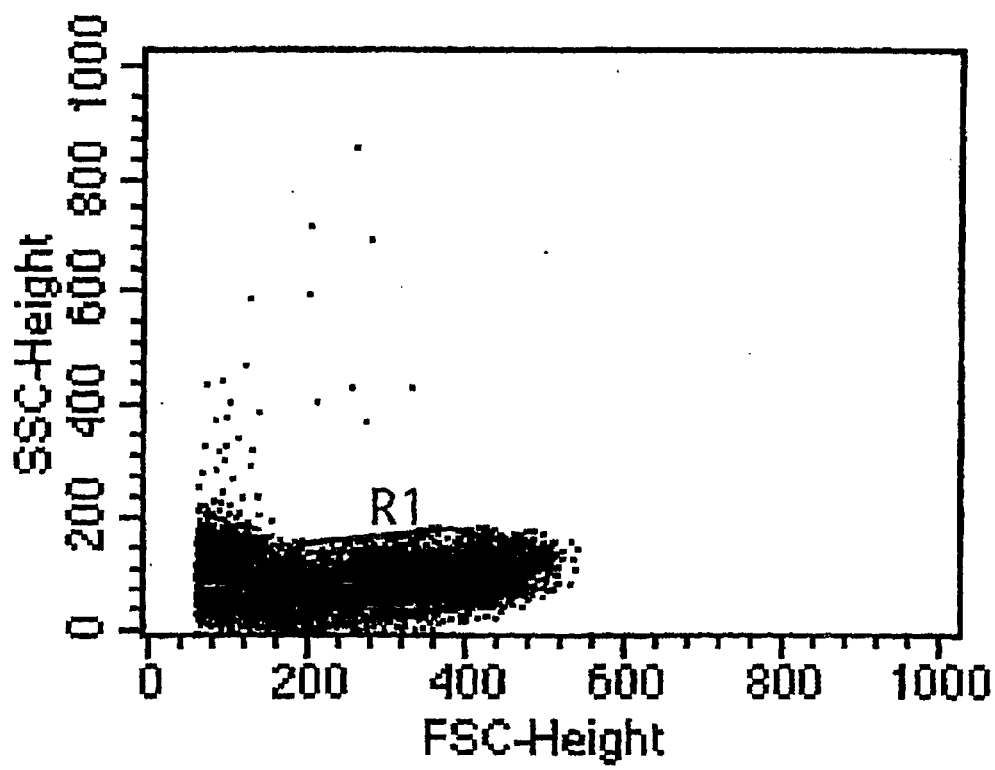
FIG. 82 is a dot plot of the results based on forward scattering light (FSC) and side scattering light (SSC) for the cell group of CD4+ cells (helper T cells) of FIG. 80 when subjected to flow cytometry (R1 is the region selected for live cells to be measured).
Figure 83:
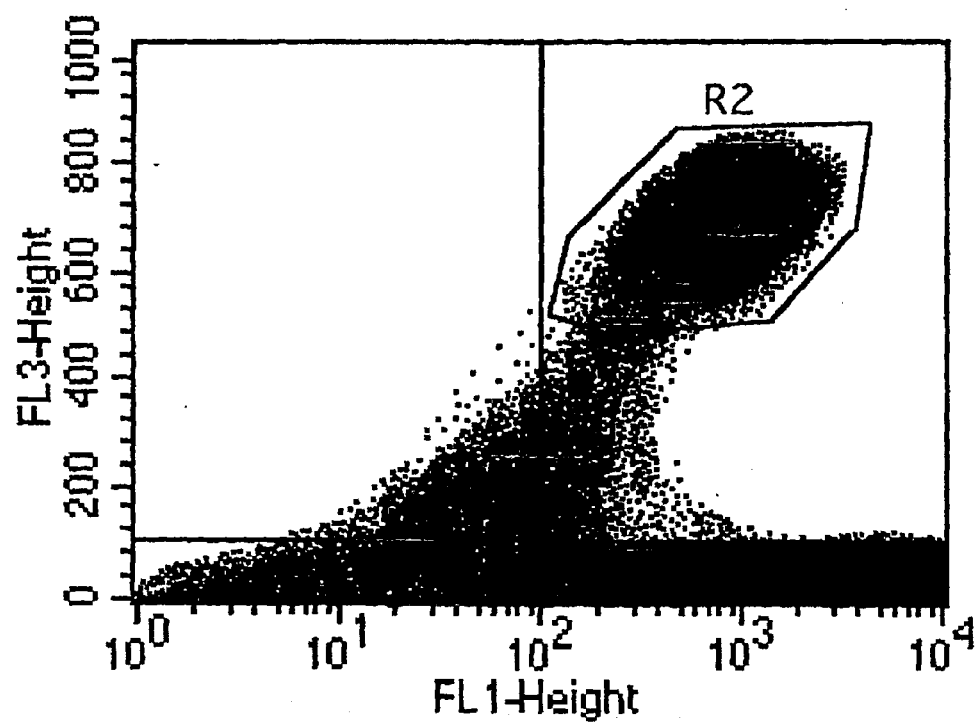
FIG. 83 is a dot plot of the results based on relative fluorescence intensity of the energy donor fluorescent dye and relative fluorescence intensity of the energy acceptor fluorescent dye due to FRET, for the cell group of CD4+ cells (helper T cells) of FIG. 80 when subjected to flow cytometry (R2 is the region selected for fluorescing cells based on FRET).

A suspension of the fluorescent probes-introduced cells obtained in (26) was applied to a flow cytometer (FACSCalibur). The excitation light of a donor dye (Bodipy) was irradiated to the cells to detect FRET fluorescence emitted from acceptors (Cy5) based on the hybridization in the same manner as (19), and then relative fluorescence intensity of Bodipy or Cy5 was shown as FL1-Height or FL3-Height, respectively in dot-plots diagram. Among these plots, a group of cells with the highest value of FL3-Height was designated as R2 (FIG. 83). On the other hand, a group of typical human lymphocytes in the points of cell size (FSC-Height; forward-scattering light) as well as the complexity in the intrastructure (SSC-Height; side-scattering light) was designated as R1 (FIG. 82). Cells belonging to both R1 and R1 was selectively separated using a cell sorting function.

Figure 84:
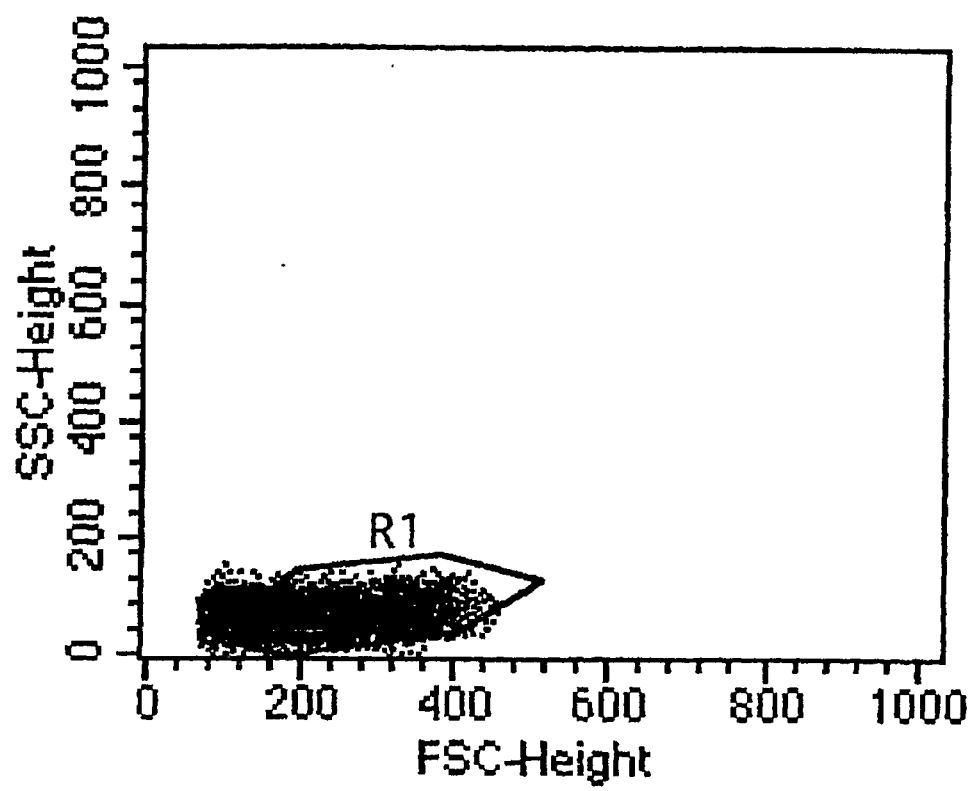
FIG. 84 is a dot plot of the results based on forward scattering light (FSC) and side scattering light (SSC) for the cell sorter-separated cell group of FIG. 81 when subjected to flow cytometry (R1 is the region selected for live cells to be measured).
Figure 85:
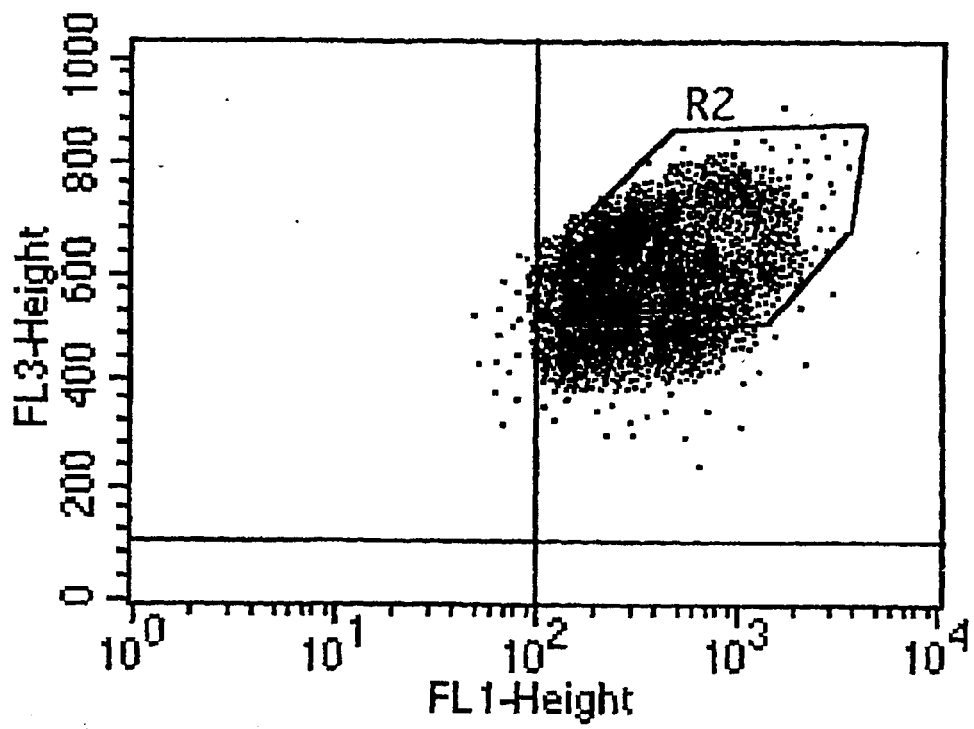
FIG. 85 is a dot plot of the results based on relative fluorescence intensity of the energy donor fluorescent dye and relative fluorescence intensity due of the energy acceptor fluorescent dye due to FRET, for the cell sorter-separated cell group of FIG. 81 when subjected to flow cytometry (R2 is the region selected for fluorescing cells based on FRET).

The separated cells were again applied to FACSCalibur and examined to confirm that they were the objective fluorescently labeled cells. The majority of the sorted-out cells by the cell sorting function belonged to both R1 and R2 (FIGS. 84 and 85), indicating that the cells with fluorescent labeled IL-4 mRNA had been separated out as ones emitting considerable FRET fluorescence.

Figure 81:
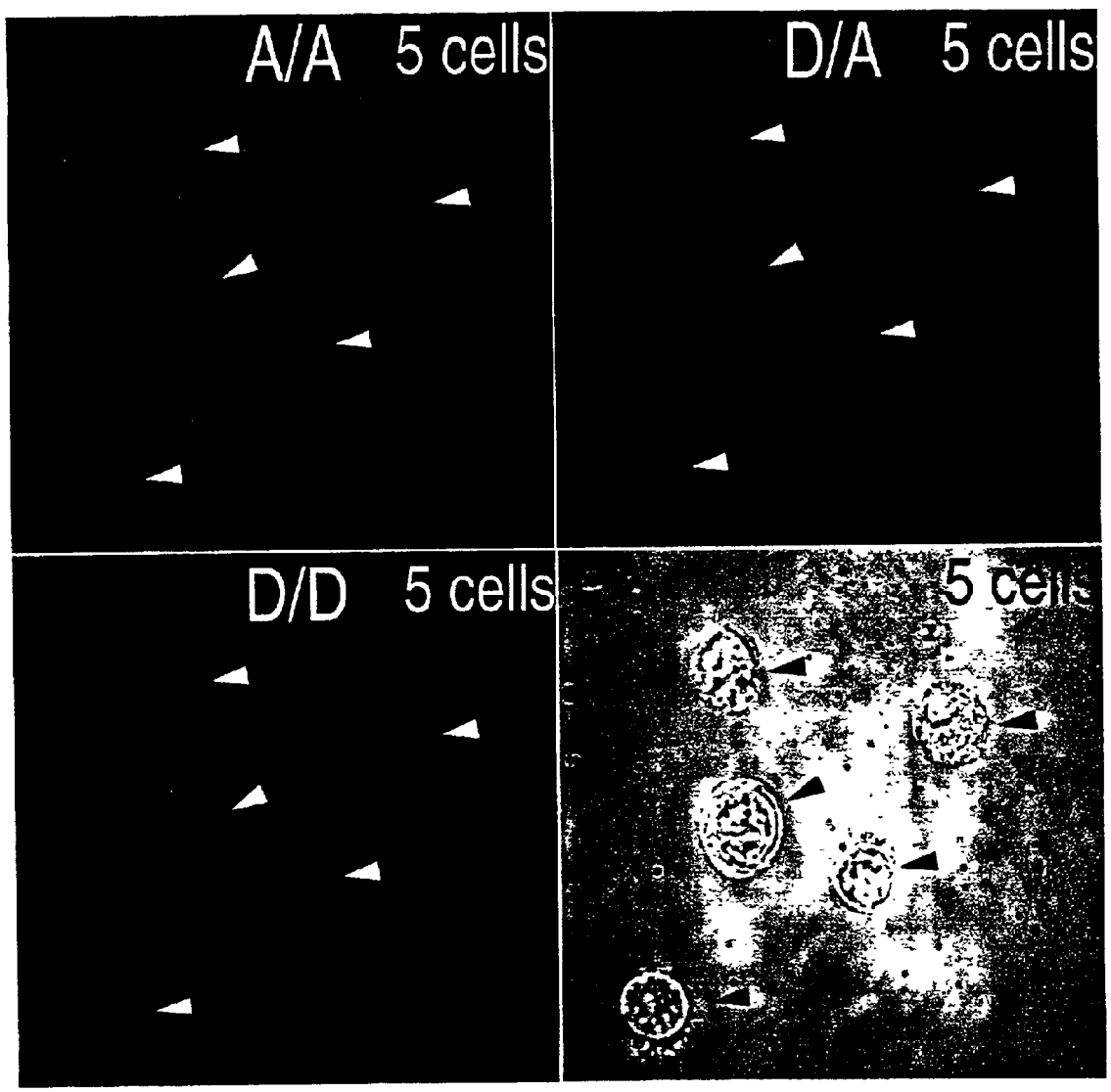
FIG. 81 is a set of micrographs showing A/A, D/A and D/D fluorescence images, and the corresponding phase contrast micrograph, of a cell group obtained by selective separation of CD4+ cell group of FIG. 80 in the live state according to flow cytometry by gating with the R1 gate of FIG. 82 and the R2 gate of FIG. 83.

Some of the sorted-out cells were then observed under a fluorescence microscope in the same manner as (20). All the cells in the entire visual field emitted D/A (FRET fluorescence), suggesting that IL-4 mRNA was fluorescently labeled in all the sorted-out cells (FIG. 81). Comparing the result above with that before cytometry in (26) for the ratios of CD4+ cells with fluorescent labeled IL-4 mRNA, it was suggested that TH2 had been selectively separated by the cell sorting function.

(28) Detection of IL-2 mRNA or IL-4 mRNA Carrying Cells Before Flow Cytometry by In Situ Hybridization Some of the cells before flow cytometry (cell sorter separation) were transferred to a cover glass chamber (Lab-Tek II Chambered Coverglass #155409, NUNC Co.), and after fixing the cells with 4% paraformaldehyde/PBS (pH 7.4) at room temperature for 30 minutes, the FISH (Fluorescence in situ Hybridization) method described below was used to determine the ratio of cells carrying IL-2 mRNA or IL-4 mRNA (IL-2 mRNA(+) or IL-4 mRNA(+)) present among the cells in the entire visual field.

First, a digoxigenin (hereunder, DIG)-labeled RNA probe for IL-2 RNA to detect intracellular IL-2 mRNA of the fixed cells was synthesized using a DIG RNA Labeling Kit (Boehringer Mannheim) according to the protocol of the kit manual. 10 µg of recombinant plasmid (pTCGF#2) constructed for human IL-2 RNA synthesis by the method described in (2A) was completely linearized by EcoRI digestion, and the linearized DNA in the obtained DNA solution was extracted with phenol/chloroform for denaturation and removal of protein and then purified by ethanol precipitation, to prepare a template for RNA probe synthesis. This template DNA (5 µg) was mixed with 1.8 mM ATP, 0.9 mM CTP, 0.7 mM GTP, 1.1 mM UTP and 0.58 mM UTP (DIG-labeled) in the presence of T7 RNA polymerase and incubated at 37° C. for 2 hours. After DNaseI solution was added to the solution and incubated for 10 minutes to degrade the template DNA, a ¹/₁₀ volume of 5M sodium acetate and an equal volume of isopropanol were added to this reaction solution and centrifuged at 15,000 g×15 min to recover the synthesized RNA a precipitate. The precipitate was dissolved in RNase-free sterile distilled water.

Secondly, a DIG-labeled RNA probe for IL-4 RNA to detect intracellular IL-4 mRNA of the fixed cells was synthesized using a DIG RNA Labeling Kit (Boehringer Mannheim) in the same manner as the IL-2. A recombinant plasmid (phIL-4 #9) constructed for human IL-4 RNA synthesis by the method described in (2B) was linearized by complete digestion with SmaI, and the linearized DNA was treated with phenol/chloroform and then purified by ethanol precipitation, to prepare a template for RNA probe synthesis. This template DNA (5 µg) was mixed with 1.2 mM ATP, 1.0 mM CTP, 1.1 mM GTP, 0.8 mM UTP and 0.5 mM UTP (DIG-labeled) in the presence of T7 RNA polymerase and incubated at 37° C. for 2 hours. After DNaseI solution was added and reacted for 10 minutes to degrade the template DNA, a ¹/₁₀ volume of 5M sodium acetate and an equal volume of isopropanol were added to this reaction solution, and centrifuged at 15,000 g×15 min to recover the synthesized RNA as a precipitate. The precipitate was dissolved in RNase-free sterile distilled water.

Thirdly, highly fragmented RNA probes for IL-2 or IL-4 were prepared to use for a hybridization experiment as in (13) because the introduction of the full length IL-2 or IL-4 RNA probe obtained above was thought to cause high background noise due to the remaining non-hybridized RNA probe in the cells. 10 µg of the IL-2 or IL-4 RNA probe was dissolved in 100 µl of an alkaline solution (42 mM NaHCO$_3$, 63 mM Na$_2$CO$_3$, 5 mM DTT) and incubated at 60° C. for 10–15 minutes. 10 µl of 3 M sodium acetate and 350 µl of EtOH were added to precipitate the RNA. After standing at −20° C. for 30 minutes, it was centrifuged at 16 krpm for 20 minutes. The precipitate was washed with 70% ethanol, dried, and dissolved in 50 μl of RNase-free sterile distilled water to prepare an alkaline denatured IL-2 or IL-4 RNA probe.

The cells fixed on the bottom of the chamber were washed 3 times with PBS(-), treated with a 0.1% Triton X-100/PBS solution at room temperature for 5 minutes to permeabilize the cells, and then washed 3 times with PBS(-) and treated with 0.2N HCl at room temperature for 10 minutes. After washing the cell monolayer with PBS(-), it was incubated for 5 minutes at 37° C. with 1 μg/ml of Proteinase K/PBS solution. After washing the cell monolayer with PBS(-), it was fixed again with 4% paraformaldehyde/PBS (pH 7.4) for 30 minutes. This was washed twice with 2 mg/ml of glycine/PBS (15 minutes per washing) and treated with 50% deionized formaldehyde/2×SSC solution (hereunder, Soln. A) for 30 minutes to prepare a hybridization solution (50% deionized formaldehyde, 5×Denhardt, 2×SSC, alkaline denatured IL-2 or IL-4 RNA probe (1 μg/ml)). The solution was denatured at 90° C. for 10 minutes and cooled on ice. Adding 100 μl of the solution to the cells, they were incubated for hybridization overnight at 45° C.

The cell monolayer after hybridization was washed with Soln. A for 5 minutes at 45° C., and then washed twice with Soln. B (10 mM Tris.HCl (pH 8.5), 500 mM NaCl) (5 min/washing) and treated with 20 mg/ml RNase A/Soln. B (pretreated at 90° C. for 10 minutes) at 37° C. for 20 minutes. After washing with Soln. A, and then Soln. C (50% deionized formaldehyde/1×SSC) for 30 minutes each at 45° C., the cells were washed again with Soln. C at room temperature for 20 minutes. After washing with Buffer 1 (100 mM maleic acid, 150 mM NaCl (pH 7.5)) (2×5 min), it was subjected to blocking with Buffer 2 (1% Blocking Reagent (Boehringer Mannheim) in Buffer 1) at room temperature for 20 minutes. After washing twice with Buffer 1, FITC-labeled anti-DIG antibody (Fab, diluted with Buffer 2 by 100 times, protein concentration: approximately 1 μg/ml) was added to the cells and incubated for at least 30 minutes. After washing 3 times with PBS(-), the cells were observed under a fluorescence microscope to examine the ratio of IL-2 mRNA or IL-4 mRNA carrying cells (TH1 or TH2) among the cells in the entire visual field.

Figure 86:
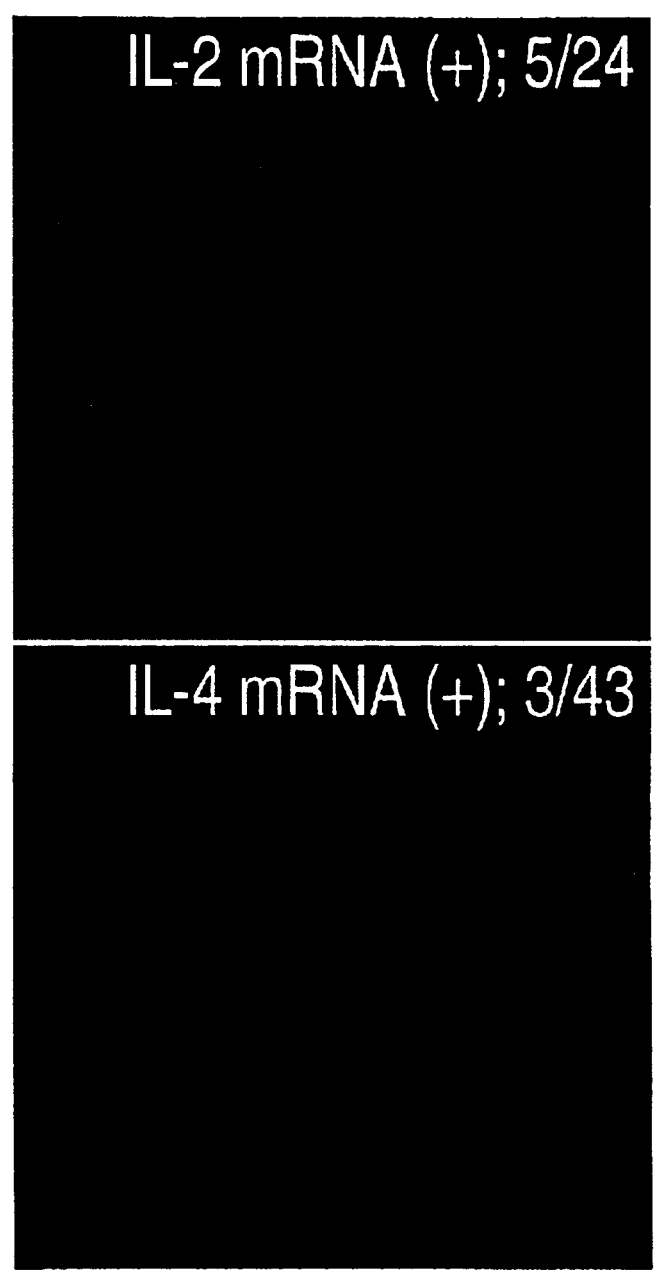

In the cells used for the experiment of (18) in which IL-2 mRNA was fluorescently labeled for selective separation of TH1, 5 cells were found to carry IL-2 mRNA out of 24 cells and 3 cells out of 43 cells were carrying IL-4 mRNA (FIG. 86). The ratio of IL-2 mRNA carrying cells (20.8%) was somewhat higher than that in (18) (12.0%). This gap is thought to be caused by the difference in the way of probe-introduction, i.e., the fluorescent probes were not introduced to some of TH1 cells in the experiment of (18).

In the cells for the experiment of (20) in which IL-4 mRNA was fluorescently labeled for selective separation of TH2, 6 cells were found to carry IL-2 mRNA out of 28 cells and 3 cells out of 42 cells were carrying IL-4 mRNA (FIG. 88). The ratio of IL-4 mRNA carrying cells (7.1%) was slightly higher than that in (20) (4.9%).

Figure 90:
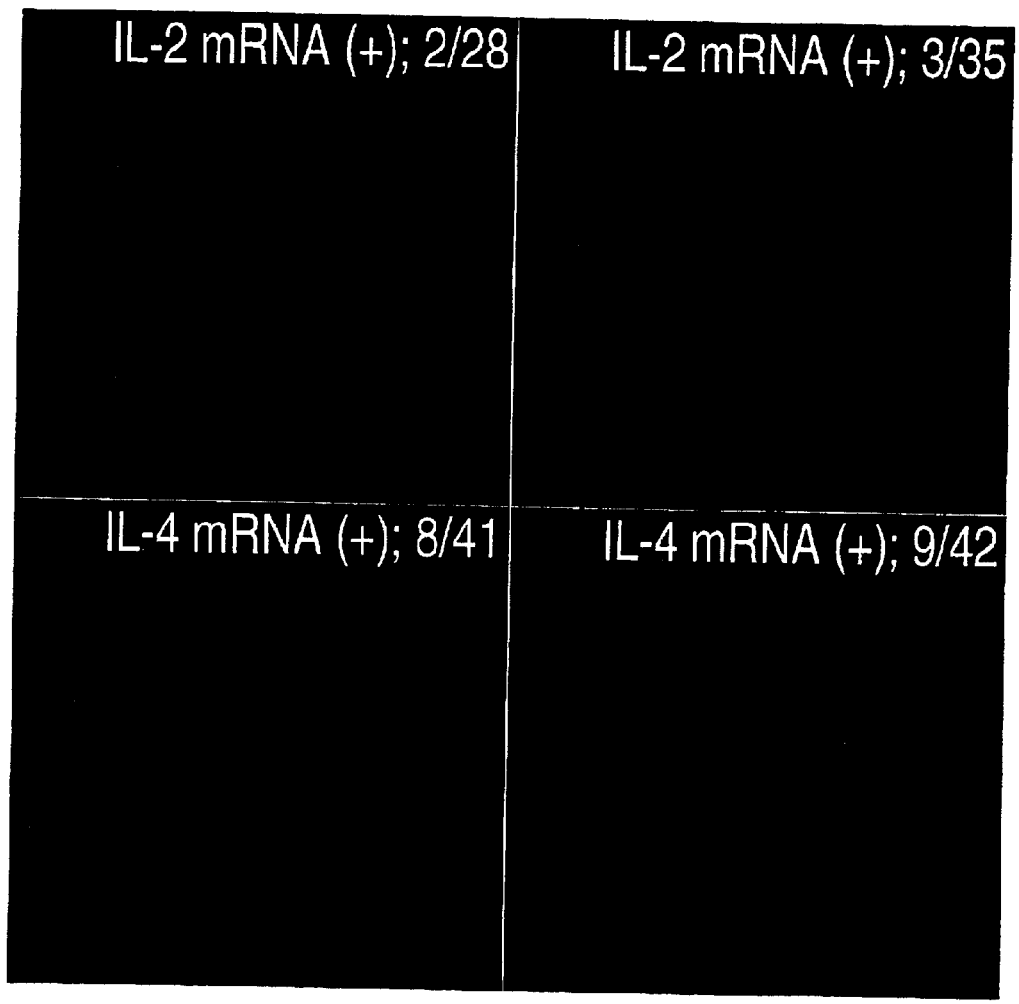
FIG. 90 is a set of fluorescence micrographs obtained when the cell group of CD4+ cells (helper T cells) of FIG. 74 before flow cytometry thereof was fixed to the bottom of a cover glass chamber, hybrids were formed between the IL-2 mRNA or IL-4 mRNA of the fixed cells and RNA probe for IL-2 RNA s or IL-4 RNA probes, and the hybrids were fluorescently detected.

Furthermore, in the cells used for the experiments of (23) in which IL-2 mRNA was fluorescently labeled for selective separation of TH1 from a TH2-dominant cell group, 2 cells out of 28 cells and 3 cells out of 35 cells were found to carry IL-2 mRNA, while 8 cells out of 41 cells and 9 cells out of 42 cells were carrying IL-4 mRNA (FIG. 90). The ratio of IL-2 mRNA carrying cells (7.9%) was higher than that in (23) (4.3%). This gap is thought to be caused by the difference in the way of probe-introduction, i.e., the fluorescent probes were not introduced to some of TH1 cells in the experiments of (23).

Figure 92:
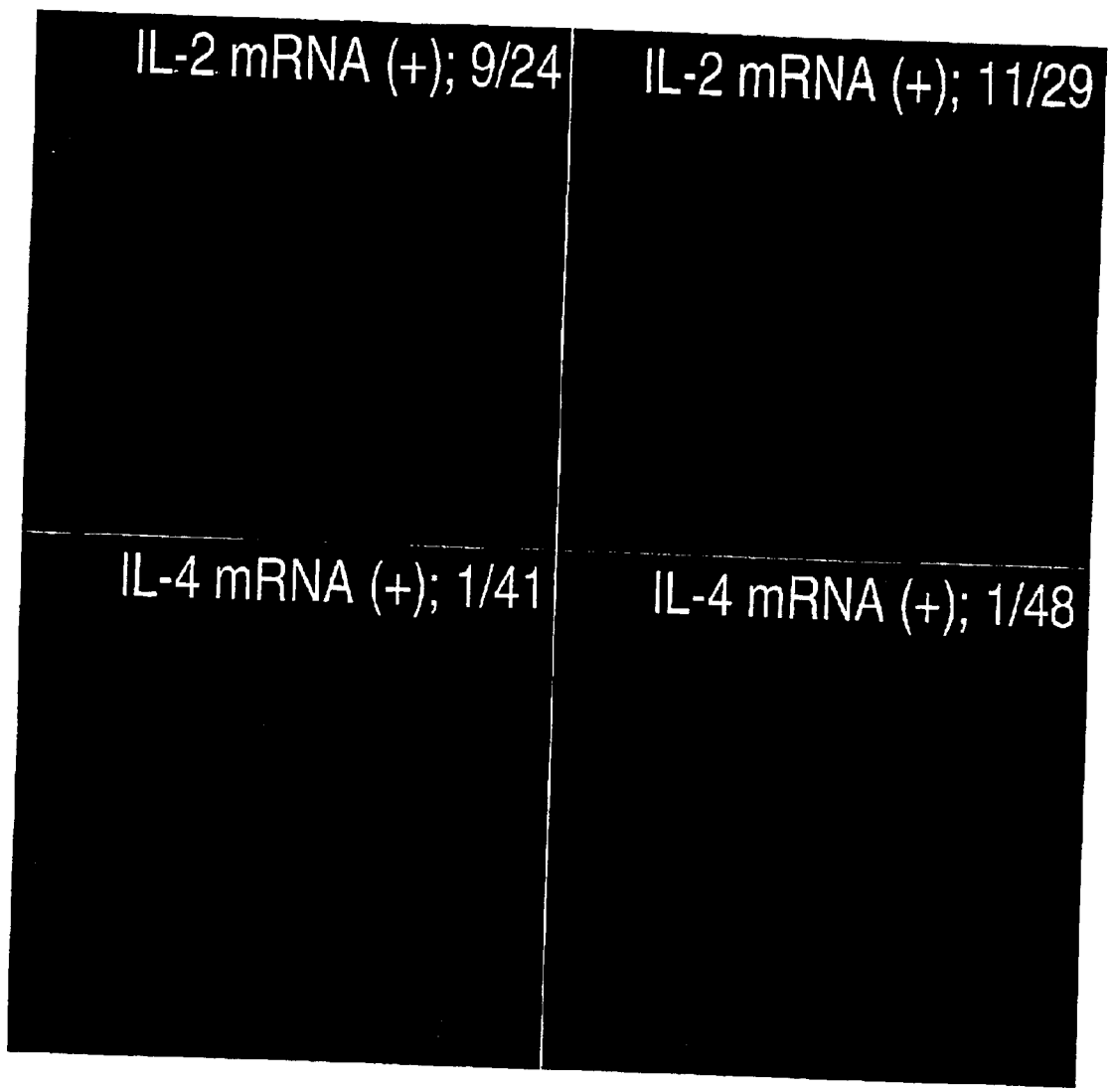
FIG. 92 is a set of fluorescence micrographs obtained when the cell group of CD4+ cells (helper T cells) of FIG. 80 before flow cytometry thereof was fixed to the bottom of a cover glass chamber, hybrids were formed between the IL-2 mRNA or IL-4 mRNA of the fixed cells and RNA probe for IL-2 RNA s or IL-4 RNA probes, and the hybrids were fluorescently detected.
Figure 94:
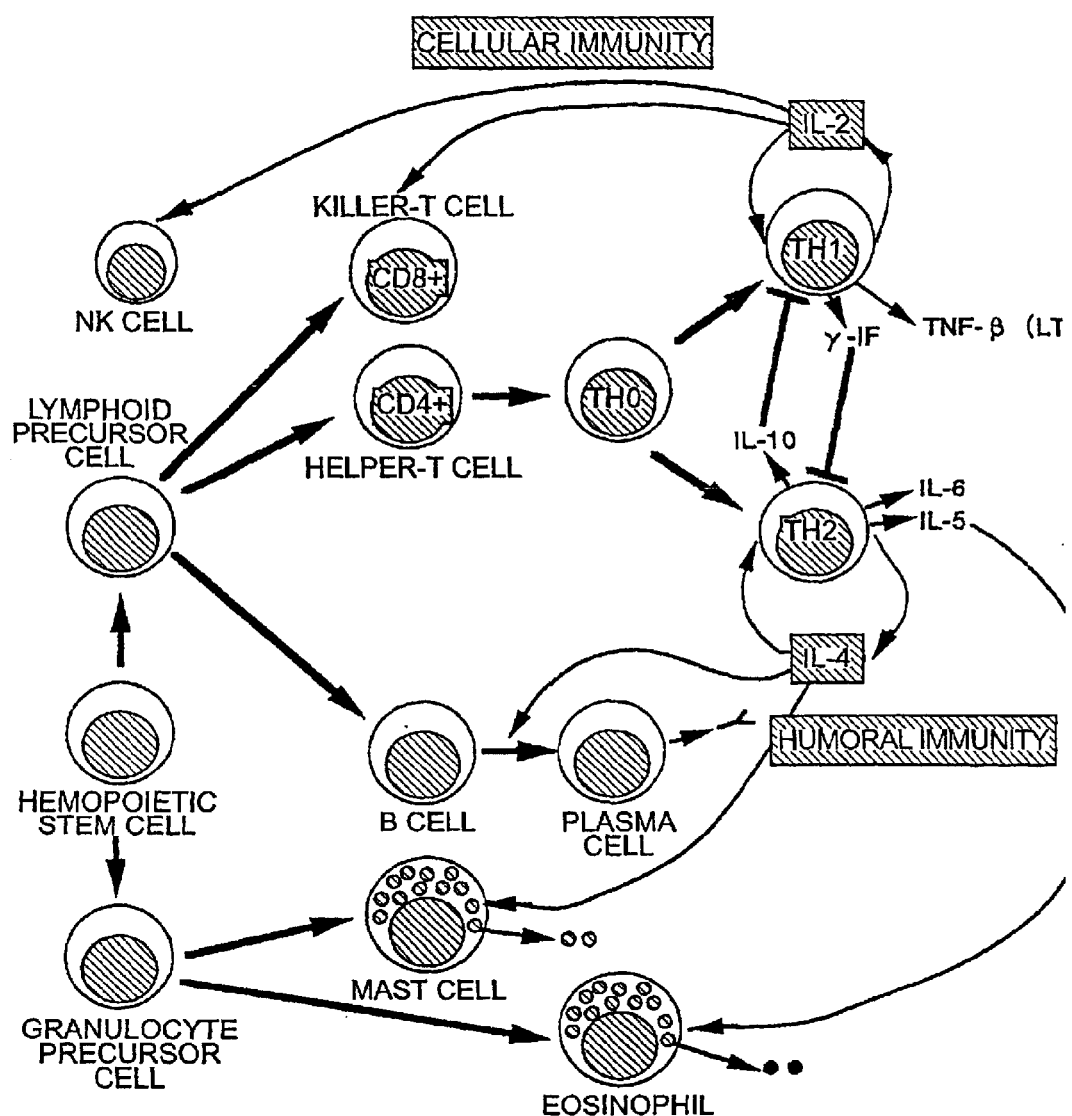
FIG. 94 is a representation showing the mutual relationship among different cells that constitute the immune system throughout their differentiation as well as the manner in which the different cells cooperate or restrain each other through cytokines such as interleukins to maintain homeostatis of immune functions of the living body.

Also, in the cells used for the experiments of (26) in which IL-4 mRNA was fluorescently labeled for selective separation of TH2 from a TH1-dominant cell group, 9 cells out of 24 cells and 11 cells out of 29 cells were found to carry IL-2 mRNA, while 1 cells out of 48 cells and 1 cells out of 41 cells were carrying IL-4 mRNA (FIG. 92). The ratio of IL-4 mRNA carrying cells (2.2%) was equal to that in (26) (2.4%). This consistence between the fluorescence microscope observation results and FISH results for IL-4 mRNA would be due to much the same frequency of probe-introduction, i.e., much the same amount of fluorescent probes were introduced to almost all the TH2 cells. This relatively uniformed introduction is thought to be obtained by the application of electrical pulse to the cells in the presence of a higher concentration of IL-4 fluorescent probe compared with IL-2 probe.

(29) Detection of IL-2, γ-IF, TNF-β, IL-4, IL-5 and IL-10 mRNA Carrying Cells in the Cells After Flow Cytometry (Selectively Separated With a Cell Sorter) by In Situ Hybridization Some of the cells after flow cytometry (selectively separated with a cell sorter) obtained in (24) to (27) were transferred to a cover glass chambers (NUNC). After fixing the cells with 4% paraformaldehyde/PBS (pH 7.4) at room temperature for 30 minutes, the FISH method described in the detail in (28) was used to examine the ratios of CD4+ cells having mRNA for the TH1 cytokines IL-2, γ-IF, TNF-β and the TH2 cytokines IL-4, IL-5 and IL-10. Since alkaline denatured RNA probes for IL-2 and IL-4 had already been obtained in (28), DIG-labeled RNA probes to detect mRNA for each of the cytokines other than IL-2 and IL-4 were synthesized using a DIG RNA Labeling Kit (Boehringer Mannheim) according to the protocol of the kit manual.

First, for γ-IF, plasmid DNA (pPLc28-HIIF52) including human γ-IF cDNA was extracted and purified using a Plasmid Midi Kit (QIAGEN) from the plasmid-carrying E. coli (ATCC#39278) that had been cultured at 28° C. The plasmid was digested with restriction enzymes BamHI and ClaI, and the obtained γ-IF cDNA fragment was linked to the AccI and BamHI restriction site of a pBluescript KS(+) vector for RNA synthesis using DNA Ligation kit version 2 (Takara). The DNA solution was introduced into competent cells of E. coli JM109 (Takara) and the recombinant plasmid DNA was extracted and purified from 100 ml culture of the resulting E. coli transformants using a Plasmid Midi Kit (QIAGEN). The recombinant plasmid (phγ-IF#1) was digested with restriction enzyme KpnI. After the linearized plasmid DNA was treated with phenol/chloroform, it was purified by ethanol precipitation to prepare a template for RNA probe synthesis. This template DNA (5 μg) was mixed with 1.3 mM ATP, 0.7 mM CTP, 0.8 mM GTP, 0.8 mM UTP and 0.43 mM UTP (DIG-labeled) in the presence of T7 RNA polymerase and incubated at 37° C. for 7 hours. After adding DNaseI to the reaction mixture, it was incubated for 10 minutes to degrade the template DNA. After a 1/10 volume of 5M sodium acetate and an equal volume of isopropanol were added to the RNA solution, it was centrifuged at 15,000 g×15 min to recover the synthesized RNA as a precipitate. The precipitate was dissolved in RNase-free sterile distilled water.

Secondly, for TNF-β, plasmid DNA carrying human TNF-β cDNA was extracted and purified using a Plasmid Midi Kit (QIAGEN) from 50 ml culture of E. coli HILBI37 (ATCC#104607) carrying the plasmid. The plasmid was digested with restriction enzyme BamHI. The linearized plasmid DNA was treated with phenol/chloroform and purified by ethanol precipitation to prepare a template for RNA probe synthesis. The template DNA (5 μg) was mixed with 0.7 mM ATP, 1.4 mM CTP, 1.1 mM GTP, 0.4 mM UTP and 0.24 mM UTP (DIG-labeled) in the presence of T7 RNA polymerase and incubated at 37° C. for 6 hours. After adding DNaseI to the reaction mixture, it was incubated for 10 minutes to degrade the template DNA. After adding a ¹⁄₁₀ volume of 5M sodium acetate and an equal volume of isopropanol to the RNA solution, it was centrifuged at 15,000 g×15 min to recover the synthesized RNA as a precipitate. The precipitate was dissolved in RNase-free sterile distilled water.

Thirdly, for IL-5, 2 μg of lyophilized human IL-5 cDNA-containing plasmid DNA, phIL-5–115.1 (ATCC#59395), was dissolved in 2 μl of sterile distilled water. 1 ng of the plasmid was introduced into competent cells of $E.\ coli$ JM109 (Takara) and the plasmid DNA was extracted and purified using a Plasmid Midi Kit (QIAGEN) from 50 ml culture of the resulting $E.\ coli$ transformants. The plasmid DNA was digested with restriction enzyme BamHI, and the isolated IL-5 cDNA fragment was linked to the BamHI restriction site of a pBluescript KS(+) vector for RNA synthesis using DNA Ligation kit version 2 (Takara). The DNA solution was introduced into competent cells of $E.\ coli$ JM19 (Takara). The recombinant plasmid DNA was extracted and purified from 100 ml culture of the resulting $E.\ coli$ transformants using a Plasmid Midi Kit (QIAGEN). The recombinant plasmid (phIL-5 #8) was digested with restriction enzyme NotI. After treating the linearized DNA with phenol/chloroform, it was purified by ethanol precipitation to prepare a template for RNA probe synthesis. This template DNA (5 μg) was mixed with 1.3 mM ATP, 0.7 mM CTP, 0.8 mM GTP, 0.8 mM UTP and 0.42 mM UTP (DIG-labeled) in the presence of T3 RNA polymerase and incubated at 37° C. for 6 hours. Adding DNaseI to the reaction mixture, it was incubated for 10 minutes to degrade the template DNA. After adding a ¹⁄₁₀ volume of 5M sodium acetate and an equal volume of isopropanol were added to this reaction solution, it was centrifuged at 15,000 g×15 min to recover the synthesized RNA as a precipitate. The precipitate was dissolved in RNase-free sterile distilled water.

Fourthly, for IL-10, pH15C, a plasmid DNA containing human IL-10 cDNA was extracted and purified using Plasmid Midi Kit (QIAGEN) from 50 ml culture of an $E.\ coli$ strain (ATCC#104607) carrying the plasmid. The plasmid was digested with restriction enzyme BamHI, and the isolated IL-10 cDNA fragment was linked to the BamHI restriction site of a pBluescript KS(+) vector for RNA synthesis using a DNA Ligation kit version 2 (Takara). The recombinant plasmid was introduced into competent cells of $E.\ coli$ JM109 (Takara). The recombinant plasmid DNA was extracted and purified from 50 ml culture of the resulting $E.\ coli$ transformants using a Plasmid Midi Kit (QIAGEN). The recombinant plasmid (phIL-10 #10) was digested with restriction enzyme SmaI. After treating the linearized DNA with phenol/chloroform, it was purified by ethanol precipitation to prepare a template for RNA probe synthesis. This template DNA (5 μg) was mixed with 1.1 mM ATP, 0.9 mM CTP, 0.9 mM GTP, 0.6 mM UTP and 0.50 mM UTP (DIG-labeled) in the presence of T7 RNA polymerase and incubated at 37° C. for 6 hours. Adding DNaseI to the reaction mixture, it was incubated for 10 minutes to degrade the template DNA. After adding a ¹⁄₁₀ volume of 5M sodium acetate and an equal volume of isopropanol to this reaction solution, it was centrifuged at 15,000 g×15 min to recover the synthesized RNA as a precipitate. The precipitate was dissolved in RNase-free sterile distilled water.

The full-length RNA probes for γ-IF, TNF-β, IL-5 and IL-10 obtained above were highly fragmented in the same manner as those for IL-2 and IL-4. 10 μg of each RNA probe was dissolved in 10 μl of the above-mentioned alkali-denaturing solution and incubated at 60° C. for 10–15 minutes. Adding 10 μl of 3M sodium acetate and 350 μl of ethanol to the denaturing solution, it was cooled at −20° C. for 30 minutes and centrifuged at 16 krpm for 20 minutes to precipitate the RNA probe. The precipitate was rinsed with 70% ethanol, dried, and dissolved in 50 μl of RNase-free sterile distilled water to prepare an alkaline denatured γ-IF, TNF-β, IL-5 or IL-10 RNA probe. Washing the cells fixed on the bottom of the chamber 3 times with PBS(-), the cells were treated with a 0.1% Triton X-100/PBS solution at room temperature for 5 minutes to permeabilize the cells. Washing 3 times with PBS(-), the permeabilized cells were treated with 0.2N HCl at room temperature for 10 minutes. After washing the cells with PBS(-), it was incubated for 5 minutes at 37° C. with 1 μg/ml Proteinase K in PBS(-). Washing the resulting cells with PBS(-), it was fixed again with 4% paraformaldehyde/PBS (pH 7.4) for 30 minutes. Washing the fixed cells twice with 2 mg/ml glycine in PBS for 15 minutes each, they were treated with 50% deionized formaldehyde/2×SSC solution (hereunder, Soln. A) for 30 minutes to prepare a hybridization solution (50% deionized formaldehyde, 5×Denhardt, 2×SSC, alkaline denatured IL-2, γ-IF, TNF-β, IL-4, IL-5, or IL-10 RNA probe (1 μg/ml)). Denaturing the solution at 90° C. for 10 minutes, it was cooled on ice. Adding 100 μl of the same solution to the cells, they were incubated overnight at 45° C.

After the hybridization, the cells were washed with Soln. A for 5 minutes at 45° C., and then washed twice with Soln. B (10 mM Tris.HCl (pH 8.5), 500 mM NaCl) for 5 minutes each. The cells were treated with 20 mg/ml RNase A/Soln. B (pretreated at 90° C. for 10 minutes) at 37° C. for 20 minutes. After washing the cells with Soln. A and Soln. C (50% deionized formaldehyde/1×SSC) for 30 minutes each at 45° C., they were washed with Soln. C at room temperature for 20 minutes. Washing the cells with Buffer 1 (100 mM maleic acid, 150 mM NaCl (pH 7.5)) (2×5 min), they were treated with Buffer 2 (1% Blocking Reagent (Boehringer Mannheim) in Buffer 1) at room temperature for 20 minutes. After washing the cells twice with Buffer 1, FITC-labeled anti-DIG antibody (Fab, diluted with Buffer 2 by 100 times, protein concentration: approximately 1 μg/ml) was added to the cells and they were incubated for at least 30 minutes. Washing the cells 3 times with PBS(-), they were observed under a fluorescence microscope to examine the ratio of IL-2, γ-IF, TNF β, IL-4, IL-5 or IL-10 mRNA carrying cells (TH1 or TH2) among the cells in the entire visual field. The cell type (TH1 or TH2) was determined for the selectively separated cells by a cell sorting function.

Figure 89:
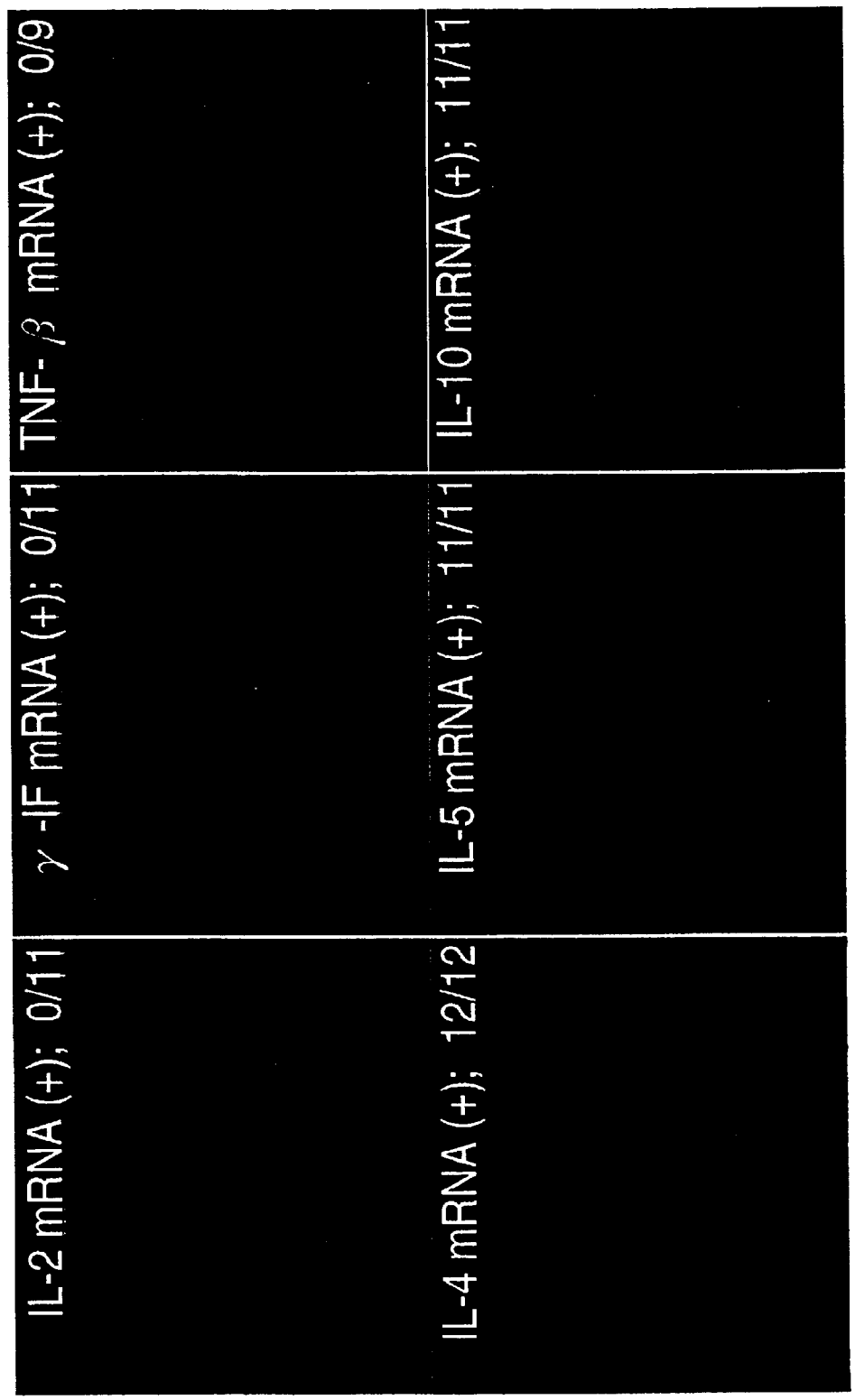
FIG. 89 is a set of fluorescence micrographs obtained when the cell group of cells selectively separated with the cell sorter in FIG. 69 was fixed to the bottom of a cover glass chamber, hybrids were formed between the IL-2, γ-IF, TNF-β, IL-4, IL-5 or IL-10 mRNA of the fixed cells and IL-2, γ-IF, TNF-β, IL-4, IL-5 or IL-10 RNA probes, respectively, and the hybrids were fluorescently detected.

The cells selectively separated by the cell sorter in (19) and (24) were positive for IL-2, γ-IF and TNF-β mRNA and negative for IL-4, IL-5 and IL-10 (FIGS. 87 and 91), indicating that all the cells examined were TH1-specific cytokine-producing cells. On the other hand, the cells selectively separated by the cell sorter in (21) and (27) were negative for IL-2, γ-IF and TNF-β mRNA and positive for IL-4, IL-5 and IL-10 (FIGS. 89 and 93), identifying all the cells examined as TH2-specific cytokine-producing cells.

(30) Selective Separation of Live TH1 and TH2 Cells Expressing Specific Genes Based on Difference in Fluorescence Intensity All the selective separation experiments of TH1 or TH2 cells based on the fluorescently labeled IL-2 or IL-4 mRNA were summarized in Table 9. In this table, their mRNAs were utilized as markers to isolate the objective TH cells throughout the experimental results from (18), (20), (23) and (26).

TABLE 9

| | | | Flow Cytometry | | |
|---|---|---|---|---|---|
| | | | Before | | After |
| | | | IL-2 or | | |
| Mixing Ratios | | FRET (D/A) | IL-4 mRNA | FRET (D/A) | IL-2 or |
| No. | Marker | Target cell type | positive cells (%) | carrying cells (%) | positive cells (%) | IL-4 mRNA carrying cells (%) |
| (18) | IL-2 mRNA | TH-1 | 12.0 | 20.8 | 100 | 100 |
| (20) | IL-4 mRNA | TH-2 | 4.9 | 7.1 | 100 | 100 |
| (23) | IL-2 mRNA | TH-1 | 4.3 | 7.9 | 100 | 100 |
| (26) | IL-4 Mrna | TH-2 | 2.4 | 2.2 | 100 | 100 |

In (18), the IL-2 expressing cells (TH1) which presented only at 12% (FIG. 60, live cell fluorescent observation results) or 20% (FIG. 86, FISH experiment results) were concentrated to 100% by the separation method utilizing the difference in fluorescence intensities as described in (19). The IL-4 expressing cells (TH2) presented only at 4.9% (FIG. 68, fluorescent observation results) or 7.1% (FIG. 88, FISH experiment results) before flow cytometry as described in (20). However, all the cells obtained by the selective separation method of (21) were IL-4 mRNA carrying cells.

Furthermore, the ratio of TH1 to TH2 cells was artificially shifted toward TH2 to mimic immune diseases with overactivation of TH2 cells in (23). Compared with (18), TH1 was notably reduced to 4.3% (FIG. 74, fluorescent observation results) or 7.9% (FIG. 90, FISH experiment results). However, TH1 cells were obtained at 100% purity by the selective separation method as shown in (24). In contrast to (23), the balance between TH1 and TH2 was artificially shifted toward TH1 in (26) to mimic immune diseases with overwhelming presence of TH1. Compared with (25), TH2 cells were reduced to 2.4% (FIG. 80, fluorescent observation results) or 2.3% (FIG. 92, FISH experiment results). However, TH2 cells were obtained at 100% purity by the selective separation method as shown in (27).

To confirm the above-mentioned results, mRNA of TH1- or TH2-specific cytokine was detected in (29). It was demonstrated that all the cells separated by the cell sorter in (19) and (24) from the cells of (18) and (23) were TH1, while all the cells selectively separated in (21) and (27) from the cells of (20) and (26) were TH2.

Throughout all these results, it was concluded that TH1 or TH2 cells are selectively separated with complete selectivity (100%) from cells containing the both cell types by the separation method utilizing mRNA of IL-2 or IL-4, a specific cytokine for TH1 or TH2 cells, respectively.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method for selectively separating live cells which have expressed mRNA encoding interleukin-2 (IL-2) comprising:
   a first step of introducing a probe capable of labeling mRNA into cells in a live cell group containing live cells which have expressed the specific mRNA;
   wherein the probe comprises a first probe having the base sequence set forth in SEQ ID NO:9 in the Sequence Listing and second probe having a base sequence set forth in SEQ ID NO:10 in the Sequence Listing each labeled with a fluorescent dye the first probe and the second probe have base sequences complementary to said mRNA and capable of hybridizing thereto adjacently, and the first probe is labeled with an energy donor fluorescent dye and the second probe is labeled with an energy acceptor fluorescent dye;
   a second step of labeling said mRNA with said probe to obtain a live cell group containing live cells having the labeled mRNA which is a hybrid of the probe and said mRNA; and
   a third step of detecting said labeled mRNA by irradiating light to the live cell group containing live cells having the hybrid and by identifying live cells which cause a change in fluorescence of said fluorescent dye based on formation of the hybrid due to fluorescence resonance energy transfer (FRET) from the energy donor fluorescent dye of the first probe to the energy acceptor fluorescent dye of the second probe, and separating the identified live cells selectively from said live cell group.

2. A method for selectively separating live cells which have expressed mRNA encoding interleukin-4 (IL-4) comprising:
   a first step of introducing a probe capable of labeling mRNA into cells in a live cell group containing live cells which have expressed the specific mRNA;
   wherein the probe comprises a first probe having the base sequence set forth in SEQ ID NO:17 in the Sequence listing and a second probe having the base sequence set forth in SEQ ID NO:18 in the Sequence Listing each labeled with a fluorescent dye; the first probe and the second probe have base sequences complementary to said mRNA and capable of hybridizing thereto adjacently, and the first probe is labeled with an energy donor fluorescent dye and the second probe is labeled with an energy acceptor fluorescent dye;

a second step of labeling said mRNA with said probe to obtain a live cell group containing live cells having the labeled mRNA which is a hybrid of the probe and said mRNA; and a third step of detecting said labeled mRNA by irradiating light to the live cell group containing live cells having the hybrid and by identifying live cells which cause a change in fluorescence of said fluorescent dye based on formation of the hybrid due to fluorescence resonance energy transfer (FRET) from the energy donor fluorescent dye of the first probe to the energy acceptor fluorescent dye of the second probe, and separating the identified live cells selectively from said live cell group.

* * * * *